(12) United States Patent
Mori et al.

(10) Patent No.: US 8,192,717 B2
(45) Date of Patent: Jun. 5, 2012

(54) COMPOSITION FOR DIAGNOSING AMYLOID-RELATED DISEASES

(75) Inventors: Hiroshi Mori, Osaka (JP); Morio Nakayama, Nagasaki (JP); Mamoru Haratake, Nagasaki (JP); Masahiro Ono, Nagasaki (JP)

(73) Assignee: Nagasaki University, Nagasaki (JP)

( * ) Notice: Subject to any disclaimer, the term of this patent is extended or adjusted under 35 U.S.C. 154(b) by 1249 days.

(21) Appl. No.: 11/666,507

(22) PCT Filed: Nov. 25, 2005

(86) PCT No.: PCT/JP2005/021642
§ 371 (c)(1),
(2), (4) Date: Oct. 2, 2007

(87) PCT Pub. No.: WO2006/057323
PCT Pub. Date: Jun. 1, 2006

(65) Prior Publication Data
US 2008/0131367 A1    Jun. 5, 2008

(30) Foreign Application Priority Data
Nov. 26, 2004   (JP) ................................. 2004-341370

(51) Int. Cl.
*A61K 51/00* (2006.01)
*A61K 49/00* (2006.01)
(52) U.S. Cl. ........................... 424/1.65; 424/9.1; 424/9.2
(58) Field of Classification Search .................... 514/27, 514/432, 456, 811, 925, 926
See application file for complete search history.

(56) References Cited

U.S. PATENT DOCUMENTS
2005/0169837 A1   8/2005   Auberson

FOREIGN PATENT DOCUMENTS

| WO | WO 00/10614 | | 3/2000 |
|---|---|---|---|
| WO | WO-03/074519 A1 | | 9/2003 |
| WO | WO-2004/069774 | * | 8/2004 |
| WO | WO-2004/069774 A2 | | 8/2004 |

OTHER PUBLICATIONS

Mariel Marder et al., 6-Bromoflavone, a High Affinity Ligand for the Central Benzodiazepine Receptors is a Member of a Family of Active Flavonoids, Biochemical and Biophysical Research Communication 223, 384-389, 1996.*
Lin, Yuh-Meei et al.; Amyloid; J. Protein Folding Disord.; No. 8, pp. 182-193 (2001).
Ono, Kenjiro et al.; Journal of Neurochemistry, vol. 87, pp. 172-181 (2003).
Extended European Search Report issued in Application No. 05809739.5 on May 17, 2011.
Mathis et al., "Imaging β-Amyloid Plaques and Neurofibrillary Tangles in the Aging Human Brain", Current Pharmaceutical Design, vol. 10, (2004) pp. 1469-1492.
Ono et al., "Radioiodinated Flavones for in Vivo Imaging of β-Amyloid Plaques in the Brain", J. Med. Chem., vol. 48 (2005) pp. 7253-7260.
Wallace et al., "On the Biogenesis of Flavone O-Glycosides and C-Glycosides in the Lemnaceae", Phytochemistry, vol. 8 (1969) pp. 93-99.

* cited by examiner

*Primary Examiner* — Michael G Hartley
*Assistant Examiner* — Jagadishwar Samala
(74) *Attorney, Agent, or Firm* — Birch, Stewart, Kolasch & Birch, LLP.

(57) ABSTRACT

A composition for diagnosing amyloid-related diseases, which comprises a flavone derivative, a chalcone derivative, a styrylchromone derivative, or a coumarin derivative, is provided. These compounds have high binding specificity to an amyloid β protein, high permeability to a blood-brain barrier, and ability to rapidly disappear from sites other than cerebral senile plaque. Accordingly, the composition of the present invention using these compounds enables the diagnosis of amyloid-related diseases with high precision.

10 Claims, 14 Drawing Sheets

R: OH, OMe, NHMe, NMe₂

A

B

COMPOSITION FOR DIAGNOSING AMYLOID-RELATED DISEASES

TECHNICAL FIELD

The present invention relates to a composition used for diagnosing amyloid-related diseases such as Alzheimer's disease, a method of screening a therapeutic or preventive agent for amyloid-related diseases using the above composition, and a method of evaluating a therapeutic or preventive agent for amyloid-related diseases using the above composition.

BACKGROUND ART

In recent years, along with rapidly aging population, an increase in dementia diseases including Alzheimer's disease (AD) as a typical example has become a serious social problem. At present, methods of clinically diagnosing AD include Hasegawa style, ADAS, and MMSE. In all of these methods, a method of quantitatively evaluating a decrease in the cognitive function of an individual, who is suspected of having AD, is generally used. Other than these methods, image diagnostic techniques (MRI, CT, etc.) are subsidiarily used. However, these diagnostic methods are insufficient for the definitive diagnosis of AD. For such definitive diagnosis, it is necessary to confirm the appearance of senile plaque and neurofibril in a brain biopsy performed in life, or in a pathological histological examination performed on the brain after death. Accordingly, it is difficult for the current diagnostic methods to diagnose AD at an early stage before the occurrence of a wide range of brain disorder. To date, there have been several reports regarding biological diagnostic markers for AD. However, such diagnostic markers that are clinically practical have not yet been developed. Under such circumstances, there is a high social need for the early diagnosis of AD, and thus it is strongly desired that such a diagnostic method be rapidly developed.

Senile plaque is a cerebral lesion that is the most characteristic of AD, and the main constituent thereof is an amyloid β protein having a β sheet structure. It is considered that imaging of such senile plaque from outside the body results in the establishment of an effective diagnostic method for AD. However, for such imaging, a probe compound that is specifically binds to such an amyloid β protein is necessary. To date, several derivatives having congo red or thioflavine T as a base structure have been reported (Patent Documents 1 and 2, and Non-Patent Document 1). However, such compounds have been considerably problematic in terms of low binding specificity to an amyloid β protein, low permeability to a blood-brain barrier, slow clearance caused by non-specific bond in brain, and the like. Therefore, the reported compounds have not yet been practically used in the diagnosis of diseases that are associated with accumulation of amyloid under the present circumstances.

[Patent Document 1] Japanese Patent Application Laid-Open No. 2004-250407
[Patent Document 2] Japanese Patent Application Laid-Open No. 2004-250411
[Non-Patent Document 1] W. E. Klunk et al., Annals of Neurology, Vol. 55, No. 3, March 2004, 306-319

DISCLOSURE OF THE INVENTION

The present invention has been made under the technical background as stated above. It is an object of the present invention to provide a compound, which has high binding specificity to an amyloid β protein, high permeability to a blood-brain barrier, and ability to rapidly disappear from sites other than cerebral senile plaque.

As a result of intensive studies directed towards achieving the aforementioned object, the present inventors have found that a flavone derivative, a chalcone derivative, a styrylchromone derivative, and a coumarin derivative, which have a structure completely differing from those of congo red or thioflavine T, have a superior property as a probe compound for imaging an amyloid β protein, thereby completing the present invention based on such findings.

That is to say, the present invention provides the following features (1) to (20):

(1) A composition for diagnosing amyloid-related diseases, which comprises a compound represented by the following general formula (I) or a pharmaceutically acceptable salt thereof:

[Chemical formula 1]

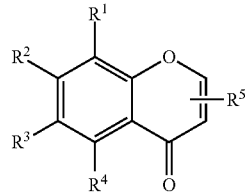

(I)

[wherein each of $R^1$, $R^2$, $R^3$, and $R^4$ independently represents a hydrogen atom, a halogen atom, a hydroxyl group, a carboxyl group, a sulfone group, a dimethylamino group, a methylamino group, an amino group, a nitro group, an alkyl group containing 1 to 4 carbon atoms, an alkoxy group containing 1 to 4 carbon atoms, a 2-fluoroethoxy group, a 3-fluoropropoxy group, a 4-fluorobutoxy group, or a 5-fluoropentoxy group; $R^5$ represents an aryl group that may be substituted with one or two or more substituents selected from the following substituent group A, an aromatic heterocyclic group that may be substituted with one or two or more substituents selected from the following substituent group A, or a group represented by the formula: —CH=CH—$R^6$ (wherein $R^6$ represents an aryl group that may be substituted with one or two or more substituents selected from the following substituent group A, or an aromatic heterocyclic group that may be substituted with one or two or more substituents selected from the following substituent group A); and the substituent group A is a group consisting of a halogen atom, a hydroxyl group, a carboxyl group, a sulfone group, a dimethylamino group, a methylamino group, an amino group, a nitro group, an alkyl group containing 1 to 4 carbon atoms, and an alkoxy group containing 1 to 4 carbon atoms].

(2) The composition for diagnosing amyloid-related diseases according to (1) above, wherein any one of $R^1$, $R^2$, $R^3$, and $R^4$ in general formula (I) is a halogen atom.

(3) The composition for diagnosing amyloid-related diseases according to (1) above, wherein any one of $R^1$, $R^2$, $R^3$, and $R^4$ in general formula (I) is an iodine atom.

(4) The composition for diagnosing amyloid-related diseases according to any one of (1) to (3) above, wherein $R^5$ in general formula (I) is a phenyl group that may be substituted with one or two or more substituents selected from the substituent group A.

(5) The composition for diagnosing amyloid-related diseases according to any one of (1) to (3) above, wherein $R^5$ in general formula (I) is a 4-dimethylaminophenyl group, a 4-methylaminophenyl group, a 4-methoxyphenyl group, or a 4-hydroxyphenyl group.

(6) The composition for diagnosing amyloid-related diseases according to any one of (1) to (3) above, wherein $R^5$ in general formula (I) is a group represented by the formula: —CH=CH—$R^6$ (wherein $R^6$ represents a phenyl group that may be substituted with one or two or more substituents selected from the substituent group A).

(7) The composition for diagnosing amyloid-related diseases according to any one of (1) to (3) above, wherein $R^5$ in general formula (I) is a 4-aminostyryl group, a 4-methylaminostyryl group, or a 4-dimethylaminostyryl group.

(8) A composition for diagnosing amyloid-related diseases, which comprises a compound represented by the following general formula (II) or a pharmaceutically acceptable salt thereof:

[Chemical formula 2]

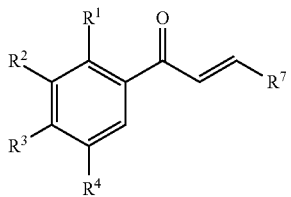

(II)

[wherein each of $R^1$, $R^2$, $R^3$, and $R^4$ independently represents a hydrogen atom, a halogen atom, a hydroxyl group, a carboxyl group, a sulfone group, a dimethylamino group, a methylamino group, an amino group, a nitro group, an alkyl group containing 1 to 4 carbon atoms, an alkoxy group containing 1 to 4 carbon atoms, a 2-fluoroethoxy group, a 3-fluoropropoxy group, a 4-fluorobutoxy group, or a 5-fluoropentoxy group; $R^7$ represents an aryl group that may be substituted with one or two or more substituents selected from the following substituent group A, or an aromatic heterocyclic group that may be substituted with one or two or more substituents selected from the following substituent group A; and the substituent group A is a group consisting of a halogen atom, a hydroxyl group, a carboxyl group, a sulfone group, a dimethylamino group, a methylamino group, an amino group, a nitro group, an alkyl group containing 1 to 4 carbon atoms, an alkoxy group containing 1 to 4 carbon atoms, a 2-fluoroethoxy group, a 3-fluoropropoxy group, a 4-fluorobutoxy group, and a 5-fluoropentoxy group].

(9) The composition for diagnosing amyloid-related diseases according to (8) above, wherein any one of $R^1$, $R^2$, $R^3$, and $R^4$ in general formula (II) is a halogen atom.

(10) The composition for diagnosing amyloid-related diseases according to (8) above, wherein any one of $R^1$, $R^2$, $R^3$, and $R^4$ in general formula (II) is an iodine atom.

(11) The composition for diagnosing amyloid-related diseases according to any one of (8) to (10) above, wherein $R^7$ in general formula (II) is a 4-hydroxy-3-methoxyphenyl group or a 4-dimethylaminophenyl group.

(12) A composition for diagnosing amyloid-related diseases, which comprises a compound represented by the following general formula (III) or a pharmaceutically acceptable salt thereof:

[Chemical formula 3]

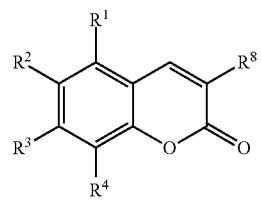

(III)

[wherein each of $R^1$, $R^2$, $R^3$, and $R^4$ independently represents a hydrogen atom, a halogen atom, a hydroxyl group, a carboxyl group, a sulfone group, a dimethylamino group, a methylamino group, an amino group, a nitro group, an alkyl group containing 1 to 4 carbon atoms, an alkoxy group containing 1 to 4 carbon atoms, a 2-fluoroethoxy group, a 3-fluoropropoxy group, a 4-fluorobutoxy group, or a 5-fluoropentoxy group; $R^8$ represents an aryl group that may be substituted with one or two or more substituents selected from the following substituent group A, or an aromatic heterocyclic group that may be substituted with one or two or more substituents selected from the following substituent group A; and the substituent group A is a group consisting of a halogen atom, a hydroxyl group, a carboxyl group, a sulfone group, a dimethylamino group, a methylamino group, an amino group, a nitro group, an alkyl group containing 1 to 4 carbon atoms, and an alkoxy group containing 1 to 4 carbon atoms].

(13) The composition for diagnosing amyloid-related diseases according to (12) above, wherein any one of $R^1$, $R^2$, $R^3$, and $R^4$ in general formula (III) is a halogen atom.

(14) The composition for diagnosing amyloid-related diseases according to (12) above, wherein any one of $R^1$, $R^2$, $R^3$, and $R^4$ in general formula (III) is an iodine atom.

(15) The composition for diagnosing amyloid-related diseases according to any one of (1) to (14) above, wherein the compound represented by general formula (I), (II), or (III) is labeled with a radionuclide.

(16) The composition for diagnosing amyloid-related diseases according to (15) above, wherein the radionuclide is a positron-emitting radionuclide.

(17) The composition for diagnosing amyloid-related diseases according to (15) above, wherein the radionuclide is a γ-ray-emitting radionuclide.

(18) The composition for diagnosing amyloid-related diseases according to any one of (1) to (17) above, wherein the amyloid-related disease is Alzheimer's disease.

(19) A method of screening a therapeutic or preventive agent used for amyloid-related diseases, which comprises the steps of: administering a test substance to a model animal with amyloid-related disease; administering to the above-described model animal the composition for diagnosing amyloid-related diseases according to any one of (1) to (18) above; and examining the distribution or amount of the compound represented by general formula (I), (II), or (III), contained in the brain of the above-described model animal.

(20) A method of evaluating a therapeutic or preventive agent used for amyloid-related diseases, which comprises the steps of: administering a therapeutic or preventive agent used for amyloid-related disease to a model animal with the above-described disease; administering to the above-described model animal the composition for diagnosing amyloid-related diseases according to any one of (1) to (18) above; and examining the distribution or amount of the compound represented by general formula (I), (II), or (III), contained in the brain of the above-described model animal.

Effects of the Invention

The compounds represented by general formula (I), (II), and (III) (hereinafter referred to as a "compound represented by general formula (I) or the like") have high binding specificity to an amyloid β protein, high permeability to a blood-brain barrier, and ability to rapidly disappear from sites other than cerebral senile plaque. Thus, these compounds are useful for the diagnosis of Alzheimer's disease.

BEST MODE FOR CARRYING OUT THE INVENTION

Figure 1:
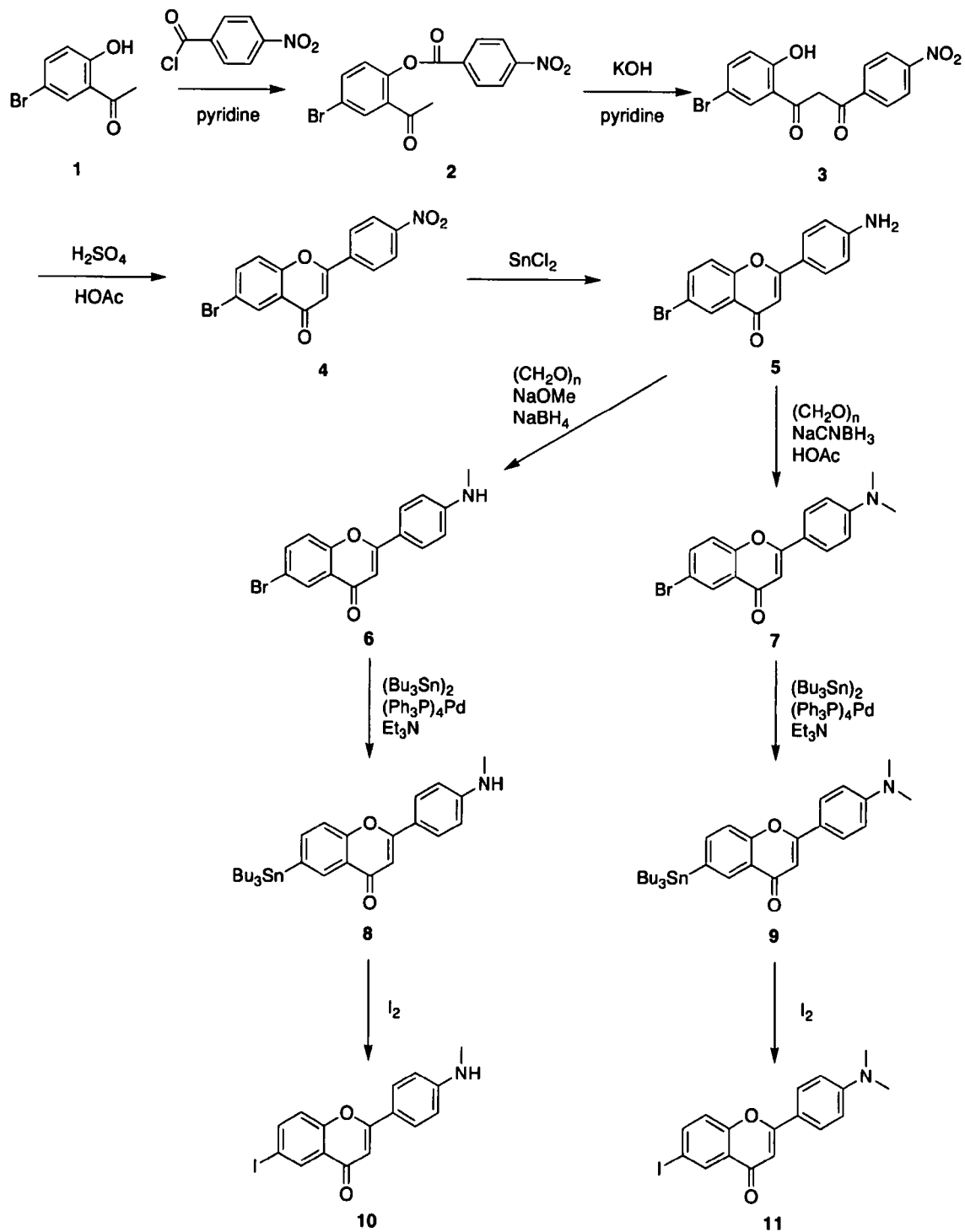
FIG. 1 is a view showing synthetic method (1) of a flavone derivative (the numbers as shown in the figure indicate compound numbers).

The present invention will be described in detail below.

Examples of the "halogen atom" used in the present invention include a fluorine atom, a chlorine atom, a bromine atom, and an iodine atom.

Examples of the "alkyl group containing 1 to 4 carbon atoms" used in the present invention include a methyl group, an ethyl group, a propyl group, an isopropyl group, a butyl group, an isobutyl group, a sec-butyl group, and a tert-butyl group.

Examples of the "alkoxy group containing 1 to 4 carbon atoms" used in the present invention include a methoxy group, an ethoxy group, a propoxy group, an isopropoxy group, a butoxy group, an isobutoxy group, a sec-butoxy group, and a tert-butoxy group.

Examples of the "aryl group" used in the present invention include a phenyl group, a 1-naphthyl group, and a 2-naphthyl group.

Examples of the "aromatic heterocyclic group" used in the present invention include a thiophen-2-yl group, a thiophen-3-yl group, a furan-2-yl group, a furan-3-yl group, a pyridin-2-yl group, a pyridin-3-yl group a pyridin-4-yl group, a pyrimidin-2-yl group, a pyrimidin-4-yl group, and a pyrimidin-5-yl group.

Examples of the "aryl group that may be substituted with a substituent selected from the substituent group A" in the present invention include a 2-dimethylaminophenyl group, a 2-methylaminophenyl group, a 2-methoxyphenyl group, a 2-hydroxyphenyl group, a 3-dimethylaminophenyl group, a 3-methylaminophenyl group, a 3-methoxyphenyl group, a 3-hydroxyphenyl group, a 4-dimethylaminophenyl group, a 4-methylaminophenyl group, a 4-methoxyphenyl group, a 4-hydroxyphenyl group, a 3-hydroxy-4-dimethylaminophenyl group, a 3-hydroxy-4-methylaminophenyl group, a 3-hydroxy-4-methoxyphenyl group, a 3,5-dihydroxy-4-dimethylaminophenyl group, a 3,5-dihydroxy-4-methylaminophenyl group, and a 3,5-dihydroxy-4-methoxyphenyl group.

Examples of the "aromatic heterocyclic group that may be substituted with a substituent selected from the substituent group A" in the present invention include a 5-dimethylaminopyridin-2-yl group, a 5-methylaminopyridin-2-yl group, a 5-methoxypyridin-2-yl group, a 6-dimethylaminopyridin-3-yl group, a 6-methylaminopyridin-3-yl group, and a 6-methoxypyridin-3-yl group.

Any one of $R^1$, $R^2$, $R^3$, and $R^4$ in general formula (I), general formula (II), and general formula (III) is preferably a halogen atom, and more preferably an iodine atom.

In general formula (I), $R^5$ is preferably a phenyl group that may be substituted with one or two or more substituents selected from the group consisting of a halogen atom, a hydroxyl group, a carboxyl group, a sulfone group, a dimethylamino group, a methylamino group, an amino group, a nitro group, an alkyl group containing 1 to 4 carbon atoms, and an alkoxy group containing 1 to 4 carbon atoms, or a group represented by the formula: —CH=CH—$R^6$ (wherein $R^6$ represents a phenyl group that may be substituted with one or two or more substituents selected from the group consisting of a halogen atom, a hydroxyl group, a carboxyl group, a sulfone group, a dimethylamino group, a methylamino group, an amino group, a nitro group, an alkyl group containing 1 to 4 carbon atoms, and an alkoxy group containing 1 to 4 carbon atoms). $R^5$ is more preferably a 4-dimethylaminophenyl group, a 4-methylaminophenyl group, a 4-methoxyphenyl group, a 4-hydroxyphenyl group, a 4-aminostyryl group, a 4-methylaminostyryl group, or a 4-dimethylaminostyryl group. As for the position of $R^5$ on chromone, $R^5$ may be either at position 2, or at position 3.

In general formula (II), $R^7$ is preferably a phenyl group that may be substituted with one or two or more substituents selected from the group consisting of a halogen atom, a hydroxyl group, a carboxyl group, a sulfone group, a dimethylamino group, a methylamino group, an amino group, a nitro group, an alkyl group containing 1 to 4 carbon atoms, and an alkoxy group containing 1 to 4 carbon atoms. $R^7$ is more preferably a 4-hydroxy-3-methoxyphenyl group or a 4-dimethylaminophenyl group.

In general formula (III), $R^8$ is preferably a phenyl group that may be substituted with one or two or more substituents selected from the group consisting of a halogen atom, a hydroxyl group, a carboxyl group, a sulfone group, a dimethylamino group, a methylamino group, an amino group, a nitro group, an alkyl group containing 1 to 4 carbon atoms, and an alkoxy group containing 1 to 4 carbon atoms. $R^8$ is more preferably a 4-methylaminophenyl group or a 4-dimethylaminophenyl group.

Among the compounds represented by general formula (I), representative compounds are shown in Tables 1 to 9.

It is to be noted that, in the following tables, "Me" indicates a methyl group, "Phe" indicates a phenyl group, "X1" indicates a 2-fluoroethoxy group, "X2" indicates a 3-fluoropropoxy group, "X3" indicates a 4-fluorobutoxy group, and "X4" indicates a 5-fluoropentoxy group.

TABLE 1

| Number | $R^1$ | $R^2$ | $R^3$ | $R^4$ | $R^5$ |
|---|---|---|---|---|---|
| I-1  | H | H | I | H  | 2-(4-NMe$_2$-Phe) |
| I-2  | H | H | I | H  | 2-(4-NHMe-Phe) |
| I-3  | H | H | I | H  | 2-(4-OMe-Phe) |
| I-4  | H | H | F | H  | 2-(4-NMe$_2$-Phe) |
| I-5  | H | H | F | H  | 2-(4-NHMe-Phe) |
| I-6  | H | H | F | H  | 2-(4-OMe-Phe) |
| I-7  | I | H | H | H  | 2-(4-NMe$_2$-Phe) |
| I-8  | I | H | H | H  | 2-(4-NHMe-Phe) |
| I-9  | I | H | H | H  | 2-(4-OMe-Phe) |
| I-10 | H | I | H | H  | 2-(4-NMe$_2$-Phe) |
| I-11 | H | I | H | H  | 2-(4-NHMe-Phe) |
| I-12 | H | I | H | H  | 2-(4-OMe-Phe) |
| I-13 | H | H | H | I  | 2-(4-NMe$_2$-Phe) |
| I-14 | H | H | H | I  | 2-(4-NHMe-Phe) |
| I-15 | H | H | H | I  | 2-(4-OMe-Phe) |
| I-16 | H | H | I | OH | 2-(4-NMe$_2$-Phe) |
| I-17 | H | H | I | OH | 2-(4-NHMe-Phe) |
| I-18 | H | H | I | OH | 2-(4-OMe-Phe) |
| I-19 | H | OH| I | OH | 2-(4-NMe$_2$-Phe) |
| I-20 | H | OH| I | OH | 2-(4-NHMe-Phe) |
| I-21 | H | OH| I | OH | 2-(4-OMe-Phe) |
| I-22 | H | H | I | H  | 3-(4-NMe$_2$-Phe) |
| I-23 | H | H | I | H  | 3-(4-NHMe-Phe) |
| I-24 | H | H | I | H  | 3-(4-OMe-Phe) |
| I-25 | H | H | I | H  | 2-(6-NMe$_2$-pyridine-3-yl) |
| I-26 | H | H | I | H  | 2-(6-NHMe-pyridine-3-yl) |
| I-27 | H | H | I | H  | 2-(6-OMe-pyridine-3-yl) |
| I-28 | H | H | I | H  | 2-CH=CH-(4-NMe$_2$-Phe) |
| I-29 | H | H | I | H  | 2-CH=CH-(4-NHMe-Phe) |
| I-30 | H | H | I | H  | 2-CH=CH-(4-OMe-Phe) |

TABLE 1-continued

| Number | $R^1$ | $R^2$ | $R^3$ | $R^4$ | $R^5$ |
|---|---|---|---|---|---|
| I-31 | H | H | I | H | 2-CH=CH-(6-NMe$_2$-pyridine-3-yl) |
| I-32 | H | H | I | H | 2-CH=CH-(6-NHMe-pyridine-3-yl) |
| I-33 | H | H | I | H | 2-CH=CH-(6-OMe-pyridine-3-yl) |
| I-34 | H | H | I | H | 2-(2-NMe$_2$-Phe) |
| I-35 | H | H | I | H | 2-(2-NHMe-Phe) |
| I-36 | H | H | I | H | 2-(2-OMe-Phe) |
| I-37 | H | H | I | H | 2-(3-NMe$_2$-Phe) |
| I-38 | H | H | I | H | 2-(3-NHMe-Phe) |
| I-39 | H | H | I | H | 2-(3-OMe-Phe) |
| I-40 | H | H | I | H | 2-(3-OH-4-NMe$_2$-Phe) |
| I-41 | H | H | I | H | 2-(3-OH-4-NHMe-Phe) |
| I-42 | H | H | I | H | 2-(3-OH-4-OMe-Phe) |
| I-43 | H | H | I | H | 2-(3,5-OH-4-NMe$_2$-Phe) |
| I-44 | H | H | I | H | 2-(3,5-OH-4-NHMe-Phe) |
| I-45 | H | H | I | H | 2-(3,5-OH-4-OMe-Phe) |

TABLE 2

| Number | $R^1$ | $R^2$ | $R^3$ | $R^4$ | $R^5$ |
|---|---|---|---|---|---|
| I-46 | H | H  | I | H  | 2-(4-OH-Phe) |
| I-47 | H | H  | F | H  | 2-(4-OH-Phe) |
| I-48 | I | H  | H | H  | 2-(4-OH-Phe) |
| I-49 | H | I  | H | H  | 2-(4-OH-Phe) |
| I-50 | H | H  | H | I  | 2-(4-OH-Phe) |
| I-51 | H | H  | I | OH | 2-(4-OH-Phe) |
| I-52 | H | OH | I | OH | 2-(4-OH-Phe) |
| I-53 | H | H  | I | H  | 3-(4-OH-Phe) |
| I-54 | H | H  | I | H  | 2-(6-OH-pyridine-3-yl) |
| I-55 | H | H  | I | H  | 2-(2-OH-Phe) |
| I-56 | H | H  | I | H  | 2-(3-OH-Phe) |
| I-57 | H | H  | I | H  | 2-(3,4-OH-Phe) |
| I-58 | H | H  | I | H  | 2-(3,4,5-OH-Phe) |
| I-59 | H | H  | I | H  | 2-CH=CH-(4-NH$_2$-Phe) |
| I-60 | H | H  | F | H  | 2-CH=CH-(4-NMe$_2$-Phe) |
| I-61 | H | H  | F | H  | 2-CH=CH-(4-NHMe-Phe) |
| I-62 | H | H  | F | H  | 2-CH=CH-(4-NH$_2$-Phe) |
| I-63 | I | H  | H | H  | 2-CH=CH-(4-NMe$_2$-Phe) |
| I-64 | I | H  | H | H  | 2-CH=CH-(4-NHMe-Phe) |
| I-65 | I | H  | H | H  | 2-CH=CH-(4-NH$_2$-Phe) |
| I-66 | H | I  | H | H  | 2-CH=CH-(4-NMe$_2$-Phe) |
| I-67 | H | I  | H | H  | 2-CH=CH-(4-NHMe-Phe) |
| I-68 | H | I  | H | H  | 2-CH=CH-(4-NH$_2$-Phe) |
| I-69 | H | H  | H | I  | 2-CH=CH-(4-NMe$_2$-Phe) |
| I-70 | H | H  | H | I  | 2-CH=CH-(4-NHMe-Phe) |
| I-71 | H | H  | H | I  | 2-CH=CH-(4-NH$_2$-Phe) |
| I-72 | H | H  | I | OH | 2-CH=CH-(4-NMe$_2$-Phe) |
| I-73 | H | H  | I | OH | 2-CH=CH-(4-NHMe-Phe) |
| I-74 | H | H  | I | OH | 2-CH=CH-(4-NH$_2$-Phe) |
| I-75 | H | OH | I | OH | 2-CH=CH-(4-NMe$_2$-Phe) |
| I-76 | H | OH | I | OH | 2-CH=CH-(4-NHMe-Phe) |
| I-77 | H | OH | I | OH | 2-CH=CH-(4-NH$_2$-Phe) |
| I-78 | H | H  | I | H  | 3-CH=CH-(4-NMe$_2$-Phe) |
| I-79 | H | H  | I | H  | 3-CH=CH-(4-NHMe-Phe) |
| I-80 | H | H  | I | H  | 3-CH=CH-(4-NH$_2$-Phe) |
| I-81 | H | H  | I | H  | 2-CH=CH-(6-NH$_2$-pyridine-3-yl) |
| I-82 | H | H  | I | H  | 2-CH=CH-(2-NMe$_2$-Phe) |
| I-83 | H | H  | I | H  | 2-CH=CH-(2-NHMe-Phe) |
| I-84 | H | H  | I | H  | 2-CH=CH-(2-NH$_2$-Phe) |
| I-85 | H | H  | I | H  | 2-CH=CH-(3-NMe$_2$-Phe) |
| I-86 | H | H  | I | H  | 2-CH=CH-(3-NHMe-Phe) |
| I-87 | H | H  | I | H  | 2-CH=CH-(3-NH$_2$-Phe) |
| I-88 | H | H  | I | H  | 2-CH=CH-(3-OH-4-NMe$_2$-Phe) |
| I-89 | H | H  | I | H  | 2-CH=CH-(3-OH-4-NHMe-Phe) |
| I-90 | H | H  | I | H  | 2-CH=CH-(3-OH-4-NH$_2$-Phe) |
| I-91 | H | H  | I | H  | 2-CH=CH-(3,5-OH-4-NMe$_2$-Phe) |
| I-92 | H | H  | I | H  | 2-CH=CH-(3,5-OH-4-NHMe-Phe) |
| I-93 | H | H  | I | H  | 2-CH=CH-(3,5-OH-4-NH$_2$-Phe) |

TABLE 3

| Number | R¹ | R² | R³ | R⁴ | R⁵ |
|---|---|---|---|---|---|
| I-94 | H | H | H | H | 2-(4-NH$_2$-Phe) |
| I-95 | H | H | H | H | 2-(4-NHMe-Phe) |
| I-96 | H | H | H | H | 2-(4-NMe$_2$-Phe) |
| I-97 | H | H | H | H | 2-(2-NH$_2$-Phe) |
| I-98 | H | H | H | H | 2-(2-NHMe-Phe) |
| I-99 | H | H | H | H | 2-(2-NMe$_2$-Phe) |
| I-100 | H | H | H | H | 2-(3-NH$_2$-Phe) |
| I-101 | H | H | H | H | 2-(3-NHMe-Phe) |
| I-102 | H | H | H | H | 2-(3-NMe$_2$-Phe) |
| I-103 | H | H | H | H | 2-(2-OH-4-NH$_2$-Phe) |
| I-104 | H | H | H | H | 2-(2-OMe-4-NH$_2$-Phe) |
| I-105 | H | H | H | H | 2-(3-OH-4-NH$_2$-Phe) |
| I-106 | H | H | H | H | 2-(3-OMe-4-NH$_2$-Phe) |
| I-107 | H | H | H | H | 2-(2-OH-4-NHMe-Phe) |
| I-108 | H | H | H | H | 2-(2-OMe-4-NHMe-Phe) |
| I-109 | H | H | H | H | 2-(3-OH-4-NHMe-Phe) |
| I-110 | H | H | H | H | 2-(3-OMe-4-NHMe-Phe) |
| I-111 | H | H | H | H | 2-(2-OH-4-NMe$_2$-Phe) |
| I-112 | H | H | H | H | 2-(2-OMe-4-NMe$_2$-Phe) |
| I-113 | H | H | H | H | 2-(3-OH-4-NMe$_2$-Phe) |
| I-114 | H | H | H | H | 2-(3-OMe-4-NMe$_2$-Phe) |
| I-115 | H | H | OH | H | 2-(4-NH$_2$-Phe) |
| I-116 | H | H | OH | H | 2-(4-NHMe-Phe) |
| I-117 | H | H | OH | H | 2-(4-NMe$_2$-Phe) |
| I-118 | H | H | OH | H | 2-(2-NH$_2$-Phe) |
| I-119 | H | H | OH | H | 2-(2-NHMe-Phe) |
| I-120 | H | H | OH | H | 2-(2-NMe$_2$-Phe) |
| I-121 | H | H | OH | H | 2-(3-NH$_2$-Phe) |
| I-122 | H | H | OH | H | 2-(3-NHMe-Phe) |
| I-123 | H | H | OH | H | 2-(3-NMe$_2$-Phe) |
| I-124 | H | H | OH | H | 2-(2-OH-4-NH$_2$-Phe) |
| I-125 | H | H | OH | H | 2-(2-OMe-4-NH$_2$-Phe) |
| I-126 | H | H | OH | H | 2-(3-OH-4-NH$_2$-Phe) |
| I-127 | H | H | OH | H | 2-(3-OMe-4-NH$_2$-Phe) |
| I-128 | H | H | OH | H | 2-(2-OH-4-NHMe-Phe) |
| I-129 | H | H | OH | H | 2-(2-OMe-4-NHMe-Phe) |
| I-130 | H | H | OH | H | 2-(3-OH-4-NHMe-Phe) |
| I-131 | H | H | OH | H | 2-(3-OMe-4-NHMe-Phe) |
| I-132 | H | H | OH | H | 2-(2-OH-4-NMe$_2$-Phe) |
| I-133 | H | H | OH | H | 2-(2-OMe-4-NMe$_2$-Phe) |
| I-134 | H | H | OH | H | 2-(3-OH-4-NMe$_2$-Phe) |
| I-135 | H | H | OH | H | 2-(3-OMe-4-NMe$_2$-Phe) |

TABLE 4

| Number | R¹ | R² | R³ | R⁴ | R⁵ |
|---|---|---|---|---|---|
| I-136 | H | H | F | H | 2-(4-NH$_2$-Phe) |
| I-137 | H | H | F | H | 2-(2-NH$_2$-Phe) |
| I-138 | H | H | F | H | 2-(2-NHMe-Phe) |
| I-139 | H | H | F | H | 2-(2-NMe$_2$-Phe) |
| I-140 | H | H | F | H | 2-(3-NH$_2$-Phe) |
| I-141 | H | H | F | H | 2-(3-NHMe-Phe) |
| I-142 | H | H | F | H | 2-(3-NMe$_2$-Phe) |
| I-143 | H | H | F | H | 2-(2-OH-4-NH$_2$-Phe) |
| I-144 | H | H | F | H | 2-(2-OMe-4-NH$_2$-Phe) |
| I-145 | H | H | F | H | 2-(3-OH-4-NH$_2$-Phe) |
| I-146 | H | H | F | H | 2-(3-OMe-4-NH$_2$-Phe) |
| I-147 | H | H | F | H | 2-(2-OH-4-NHMe-Phe) |
| I-148 | H | H | F | H | 2-(2-OMe-4-NHMe-Phe) |
| I-149 | H | H | F | H | 2-(3-OH-4-NHMe-Phe) |
| I-150 | H | H | F | H | 2-(3-OMe-4-NHMe-Phe) |
| I-151 | H | H | F | H | 2-(2-OH-4-NMe$_2$-Phe) |
| I-152 | H | H | F | H | 2-(2-OMe-4-NMe$_2$-Phe) |
| I-153 | H | H | F | H | 2-(3-OH-4-NMe$_2$-Phe) |
| I-154 | H | H | F | H | 2-(3-OMe-4-NMe$_2$-Phe) |
| I-155 | H | H | I | H | 2-(4-NH$_2$-Phe) |
| I-156 | H | H | I | H | 2-(2-NH$_2$-Phe) |
| I-157 | H | H | I | H | 2-(3-NH$_2$-Phe) |
| I-158 | H | H | I | H | 2-(2-OH-4-NH$_2$-Phe) |
| I-159 | H | H | I | H | 2-(2-OMe-4-NH$_2$-Phe) |
| I-160 | H | H | I | H | 2-(3-OH-4-NH$_2$-Phe) |
| I-161 | H | H | I | H | 2-(3-OMe-4-NH$_2$-Phe) |
| I-162 | H | H | I | H | 2-(2-OH-4-NHMe-Phe) |
| I-163 | H | H | I | H | 2-(2-OMe-4-NHMe-Phe) |
| I-164 | H | H | I | H | 2-(3-OMe-4-NHMe-Phe) |
| I-165 | H | H | I | H | 2-(2-OH-4-NMe$_2$-Phe) |
| I-166 | H | H | I | H | 2-(2-OMe-4-NMe$_2$-Phe) |
| I-167 | H | H | I | H | 2-(3-OMe-4-NMe$_2$-Phe) |

TABLE 5

| Number | R¹ | R² | R³ | R⁴ | R⁵ |
|---|---|---|---|---|---|
| I-168 | H | OH | H | H | 2-(2-NH$_2$-Phe) |
| I-169 | H | OH | H | H | 2-(3-NH$_2$-Phe) |
| I-170 | H | OH | H | H | 2-(4-NH$_2$-Phe) |
| I-171 | H | OH | H | H | 2-(2-NHMe-Phe) |
| I-172 | H | OH | H | H | 2-(3-NHMe-Phe) |
| I-174 | H | OH | H | H | 2-(4-NHMe-Phe) |
| I-175 | H | OH | H | H | 2-(2-NMe$_2$-Phe) |
| I-176 | H | OH | H | H | 2-(3-NMe$_2$-Phe) |
| I-177 | H | OH | H | H | 2-(4-NMe$_2$-Phe) |
| I-178 | H | OH | H | H | 2-(2-OH-Phe) |
| I-179 | H | OH | H | H | 2-(3-OH-Phe) |
| I-180 | H | OH | H | H | 2-(4-OH-Phe) |
| I-181 | H | OH | H | H | 2-(2-OMe-Phe) |
| I-182 | H | OH | H | H | 2-(3-OMe-Phe) |
| I-183 | H | OH | H | H | 2-(4-OMe-Phe) |
| I-184 | H | H | OH | H | 2-(2-OH-Phe) |
| I-185 | H | H | OH | H | 2-(3-OH-Phe) |
| I-186 | H | H | OH | H | 2-(4-OH-Phe) |
| I-187 | H | H | OH | H | 2-(2-OMe-Phe) |
| I-188 | H | H | OH | H | 2-(3-OMe-Phe) |
| I-189 | H | H | OH | H | 2-(4-OMe-Phe) |

TABLE 6

| Number | R¹ | R² | R³ | R⁴ | R⁵ |
|---|---|---|---|---|---|
| I-190 | H | F | H | H | 2-(2-NH$_2$-Phe) |
| I-191 | H | F | H | H | 2-(3-NH$_2$-Phe) |
| I-192 | H | F | H | H | 2-(4-NH$_2$-Phe) |
| I-193 | H | F | H | H | 2-(2-NHMe-Phe) |
| I-194 | H | F | H | H | 2-(3-NHMe-Phe) |
| I-195 | H | F | H | H | 2-(4-NHMe-Phe) |
| I-196 | H | F | H | H | 2-(2-NMe$_2$-Phe) |
| I-197 | H | F | H | H | 2-(3-NMe$_2$-Phe) |
| I-198 | H | F | H | H | 2-(4-NMe$_2$-Phe) |
| I-199 | H | F | H | H | 2-(2-OH-Phe) |
| I-200 | H | F | H | H | 2-(3-OH-Phe) |
| I-201 | H | F | H | H | 2-(4-OH-Phe) |
| I-202 | H | F | H | H | 2-(2-OMe-Phe) |
| I-203 | H | F | H | H | 2-(3-OMe-Phe) |
| I-204 | H | F | H | H | 2-(4-OMe-Phe) |
| I-205 | H | H | F | H | 2-(3-NMe$_2$-Phe) |
| I-206 | H | H | F | H | 2-(2-OH-Phe) |
| I-207 | H | H | F | H | 2-(3-OH-Phe) |
| I-208 | H | H | F | H | 2-(2-OMe-Phe) |
| I-209 | H | H | F | H | 2-(3-OMe-Phe) |
| I-210 | H | I | H | H | 2-(2-NH$_2$-Phe) |
| I-211 | H | I | H | H | 2-(3-NH$_2$-Phe) |
| I-212 | H | I | H | H | 2-(4-NH$_2$-Phe) |
| I-213 | H | I | H | H | 2-(2-NHMe-Phe) |
| I-214 | H | I | H | H | 2-(3-NHMe-Phe) |
| I-215 | H | I | H | H | 2-(2-NMe$_2$-Phe) |
| I-216 | H | I | H | H | 2-(3-NMe$_2$-Phe) |
| I-217 | H | I | H | H | 2-(2-OH-Phe) |
| I-218 | H | I | H | H | 2-(3-OH-Phe) |
| I-219 | H | I | H | H | 2-(4-OH-Phe) |
| I-220 | H | I | H | H | 2-(2-OMe-Phe) |
| I-221 | H | I | H | H | 2-(3-OMe-Phe) |

TABLE 7

| Number | R¹ | R² | R³ | R⁴ | R⁵ |
|---|---|---|---|---|---|
| I-222 | X1 | H | H | H | 2-(4-$NH_2$-Phe) |
| I-223 | X1 | H | H | H | 2-(4-NHMe-Phe) |
| I-224 | X1 | H | H | H | 2-(4-$NMe_2$-Phe) |
| I-225 | X1 | H | H | H | 2-(4-OMe-Phe) |
| I-226 | X1 | H | H | H | 2-(4-OH-Phe) |
| I-227 | X1 | H | H | H | 2-(3-$NH_2$-Phe) |
| I-228 | X1 | H | H | H | 2-(3-NHMe-Phe) |
| I-229 | X1 | H | H | H | 2-(3-$NMe_2$-Phe) |
| I-230 | X1 | H | H | H | 2-(3-OMe-Phe) |
| I-231 | X1 | H | H | H | 2-(3-OH-Phe) |
| I-232 | X2 | H | H | H | 2-(4-$NH_2$-Phe) |
| I-233 | X2 | H | H | H | 2-(4-NHMe-Phe) |
| I-234 | X2 | H | H | H | 2-(4-$NMe_2$-Phe) |
| I-235 | X2 | H | H | H | 2-(4-OMe-Phe) |
| I-236 | X2 | H | H | H | 2-(4-OH-Phe) |
| I-237 | X2 | H | H | H | 2-(3-$NH_2$-Phe) |
| I-238 | X2 | H | H | H | 2-(3-NHMe-Phe) |
| I-239 | X2 | H | H | H | 2-(3-$NMe_2$-Phe) |
| I-240 | X2 | H | H | H | 2-(3-OMe-Phe) |
| I-241 | X2 | H | H | H | 2-(3-OH-Phe) |
| I-242 | X3 | H | H | H | 2-(4-$NH_2$-Phe) |
| I-243 | X3 | H | H | H | 2-(4-NHMe-Phe) |
| I-244 | X3 | H | H | H | 2-(4-$NMe_2$-Phe) |
| I-245 | X3 | H | H | H | 2-(4-OMe-Phe) |
| I-246 | X3 | H | H | H | 2-(4-OH-Phe) |
| I-247 | X3 | H | H | H | 2-(3-$NH_2$-Phe) |
| I-248 | X3 | H | H | H | 2-(3-NHMe-Phe) |
| I-249 | X3 | H | H | H | 2-(3-$NMe_2$-Phe) |
| I-250 | X3 | H | H | H | 2-(3-OMe-Phe) |
| I-251 | X3 | H | H | H | 2-(3-OH-Phe) |
| I-252 | X4 | H | H | H | 2-(4-$NH_2$-Phe) |
| I-253 | X4 | H | H | H | 2-(4-NHMe-Phe) |
| I-254 | X4 | H | H | H | 2-(4-$NMe_2$-Phe) |
| I-255 | X4 | H | H | H | 2-(4-OMe-Phe) |
| I-256 | X4 | H | H | H | 2-(4-OH-Phe) |
| I-257 | X4 | H | H | H | 2-(3-$NH_2$-Phe) |
| I-258 | X4 | H | H | H | 2-(3-NHMe-Phe) |
| I-259 | X4 | H | H | H | 2-(3-$NMe_2$-Phe) |
| I-260 | X4 | H | H | H | 2-(3-OMe-Phe) |
| I-261 | X4 | H | H | H | 2-(3-OH-Phe) |

TABLE 8

| Number | R¹ | R² | R³ | R⁴ | R⁵ |
|---|---|---|---|---|---|
| I-262 | H | X1 | H | H | 2-(4-$NH_2$-Phe) |
| I-263 | H | X1 | H | H | 2-(4-NHMe-Phe) |
| I-264 | H | X1 | H | H | 2-(4-$NMe_2$-Phe) |
| I-265 | H | X1 | H | H | 2-(4-OMe-Phe) |
| I-266 | H | X1 | H | H | 2-(4-OH-Phe) |
| I-267 | H | X1 | H | H | 2-(3-$NH_2$-Phe) |
| I-268 | H | X1 | H | H | 2-(3-NHMe-Phe) |
| I-269 | H | X1 | H | H | 2-(3-$NMe_2$-Phe) |
| I-270 | H | X1 | H | H | 2-(3-OMe-Phe) |
| I-271 | H | X1 | H | H | 2-(3-OH-Phe) |
| I-272 | H | X2 | H | H | 2-(4-$NH_2$-Phe) |
| I-273 | H | X2 | H | H | 2-(4-NHMe-Phe) |
| I-274 | H | X2 | H | H | 2-(4-$NMe_2$-Phe) |
| I-275 | H | X2 | H | H | 2-(4-OMe-Phe) |
| I-276 | H | X2 | H | H | 2-(4-OH-Phe) |
| I-277 | H | X2 | H | H | 2-(3-$NH_2$-Phe) |
| I-278 | H | X2 | H | H | 2-(3-NHMe-Phe) |
| I-279 | H | X2 | H | H | 2-(3-$NMe_2$-Phe) |
| I-280 | H | X2 | H | H | 2-(3-OMe-Phe) |
| I-281 | H | X2 | H | H | 2-(3-OH-Phe) |
| I-282 | H | X3 | H | H | 2-(4-$NH_2$-Phe) |
| I-283 | H | X3 | H | H | 2-(4-NHMe-Phe) |
| I-284 | H | X3 | H | H | 2-(4-$NMe_2$-Phe) |
| I-285 | H | X3 | H | H | 2-(4-OMe-Phe) |
| I-286 | H | X3 | H | H | 2-(4-OH-Phe) |
| I-287 | H | X3 | H | H | 2-(3-$NH_2$-Phe) |
| I-288 | H | X3 | H | H | 2-(3-NHMe-Phe) |
| I-289 | H | X3 | H | H | 2-(3-$NMe_2$-Phe) |
| I-290 | H | X3 | H | H | 2-(3-OMe-Phe) |
| I-291 | H | X3 | H | H | 2-(3-OH-Phe) |
| I-292 | H | X4 | H | H | 2-(4-$NH_2$-Phe) |
| I-293 | H | X4 | H | H | 2-(4-NHMe-Phe) |
| I-294 | H | X4 | H | H | 2-(4-$NMe_2$-Phe) |
| I-295 | H | X4 | H | H | 2-(4-OMe-Phe) |
| I-296 | H | X4 | H | H | 2-(4-OH-Phe) |
| I-297 | H | X4 | H | H | 2-(3-$NH_2$-Phe) |
| I-298 | H | X4 | H | H | 2-(3-NHMe-Phe) |
| I-299 | H | X4 | H | H | 2-(3-$NMe_2$-Phe) |
| I-300 | H | X4 | H | H | 2-(3-OMe-Phe) |
| I-301 | H | X4 | H | H | 2-(3-OH-Phe) |

TABLE 9

| Number | R¹ | R² | R³ | R⁴ | R⁵ |
|---|---|---|---|---|---|
| I-302 | H | H | X1 | H | 2-(4-$NH_2$-Phe) |
| I-303 | H | H | X1 | H | 2-(4-NHMe-Phe) |
| I-304 | H | H | X1 | H | 2-(4-$NMe_2$-Phe) |
| I-305 | H | H | X1 | H | 2-(4-OMe-Phe) |
| I-306 | H | H | X1 | H | 2-(4-OH-Phe) |
| I-307 | H | H | X1 | H | 2-(3-$NH_2$-Phe) |
| I-308 | H | H | X1 | H | 2-(3-NHMe-Phe) |
| I-309 | H | H | X1 | H | 2-(3-$NMe_2$-Phe) |
| I-310 | H | H | X1 | H | 2-(3-OMe-Phe) |
| I-311 | H | H | X1 | H | 2-(3-OH-Phe) |
| I-312 | H | H | X2 | H | 2-(4-$NH_2$-Phe) |
| I-313 | H | H | X2 | H | 2-(4-NHMe-Phe) |
| I-314 | H | H | X2 | H | 2-(4-$NMe_2$-Phe) |
| I-315 | H | H | X2 | H | 2-(4-OMe-Phe) |
| I-316 | H | H | X2 | H | 2-(4-OH-Phe) |
| I-317 | H | H | X2 | H | 2-(3-$NH_2$-Phe) |
| I-318 | H | H | X2 | H | 2-(3-NHMe-Phe) |
| I-319 | H | H | X2 | H | 2-(3-$NMe_2$-Phe) |
| I-320 | H | H | X2 | H | 2-(3-OMe-Phe) |
| I-321 | H | H | X2 | H | 2-(3-OH-Phe) |
| I-322 | H | H | X3 | H | 2-(4-$NH_2$-Phe) |
| I-323 | H | H | X3 | H | 2-(4-NHMe-Phe) |
| I-324 | H | H | X3 | H | 2-(4-$NMe_2$-Phe) |
| I-325 | H | H | X3 | H | 2-(4-OMe-Phe) |
| I-326 | H | H | X3 | H | 2-(4-OH-Phe) |
| I-327 | H | H | X3 | H | 2-(3-$NH_2$-Phe) |
| I-328 | H | H | X3 | H | 2-(3-NHMe-Phe) |
| I-329 | H | H | X3 | H | 2-(3-$NMe_2$-Phe) |
| I-330 | H | H | X3 | H | 2-(3-OMe-Phe) |
| I-331 | H | H | X3 | H | 2-(3-OH-Phe) |
| I-332 | H | H | X4 | H | 2-(4-$NH_2$-Phe) |
| I-333 | H | H | X4 | H | 2-(4-NHMe-Phe) |
| I-334 | H | H | X4 | H | 2-(4-$NMe_2$-Phe) |
| I-335 | H | H | X4 | H | 2-(4-OMe-Phe) |
| I-336 | H | H | X4 | H | 2-(4-OH-Phe) |
| I-337 | H | H | X4 | H | 2-(3-$NH_2$-Phe) |
| I-338 | H | H | X4 | H | 2-(3-NHMe-Phe) |
| I-339 | H | H | X4 | H | 2-(3-$NMe_2$-Phe) |
| I-340 | H | H | X4 | H | 2-(3-OMe-Phe) |
| I-341 | H | H | X4 | H | 2-(3-OH-Phe) |

Among the aforementioned compounds, preferred compounds may include compound I-1 (compound 11), compound I-2 (compound 10), compound I-3 (compound 19), compound I-28 (compound 47), compound I-29 (compound 48), compound I-46 (compound 20), and compound I-59 (compound 46).

Representative compounds among the compounds represented by general formula (II) are shown in Tables 10 to 20.

TABLE 10

| Number | R¹ | R² | R³ | R⁴ | R⁷ |
|---|---|---|---|---|---|
| II-1 | H | H | I | H | 3-OMe-4-OH-Phe |
| II-2 | H | H | I | H | 4-$NMe_2$-Phe |
| II-3 | H | H | F | H | 3-OMe-4-OH-Phe |

TABLE 10-continued

| Number | R¹ | R² | R³ | R⁴ | R⁷ |
|---|---|---|---|---|---|
| II-4 | H | H | F | H | 4-NMe$_2$-Phe |
| II-5 | I | H | H | H | 3-OMe-4-OH-Phe |
| II-6 | I | H | H | H | 4-NMe$_2$-Phe |
| II-7 | H | I | H | H | 3-OMe-4-OH-Phe |
| II-8 | H | I | H | H | 4-NMe$_2$-Phe |
| II-9 | H | H | H | I | 3-OMe-4-OH-Phe |
| II-10 | H | H | H | I | 4-NMe$_2$-Phe |
| II-11 | H | H | I | OH | 3-OMe-4-OH-Phe |
| II-12 | H | H | I | OH | 4-NMe$_2$-Phe |
| II-13 | H | OH | I | OH | 3-OMe-4-OH-Phe |
| II-14 | H | OH | I | OH | 4-NMe$_2$-Phe |
| II-15 | H | H | I | H | 5-OMe-6-OH-pyridine-3-yl |
| II-16 | H | H | I | H | 6-NMe$_2$-pyridine-3-yl |
| II-17 | H | H | I | H | 4-OMe-2-OH-Phe |
| II-18 | H | H | I | H | 2-NMe$_2$-Phe |
| II-19 | H | H | I | H | 5-OMe-3-OH-Phe |
| II-20 | H | H | I | H | 3-NMe$_2$-Phe |
| II-21 | H | H | I | H | 3-OH-4-NMe$_2$-Phe |
| II-22 | H | H | I | H | 3-OMe-2,4-OH-Phe |
| II-23 | H | H | I | H | 3,5-OH-4-NMe$_2$-Phe |
| II-24 | H | H | H | H | 4-NH$_2$-Phe |
| II-25 | H | H | H | H | 4-NHMe-Phe |
| II-26 | H | H | H | H | 4-NMe$_2$-Phe |
| II-27 | H | H | H | H | 2-NH$_2$-Phe |
| II-28 | H | H | H | H | 2-NHMe-Phe |
| II-29 | H | H | H | H | 2-NMe$_2$-Phe |
| II-30 | H | H | H | H | 3-NH$_2$-Phe |
| II-31 | H | H | H | H | 3-NHMe-Phe |
| II-32 | H | H | H | H | 3-NMe$_2$-Phe |
| II-33 | H | H | H | H | 2-OH-4-NH$_2$-Phe |
| II-34 | H | H | H | H | 2-OMe-4-NH$_2$-Phe |
| II-35 | H | H | H | H | 3-OH-4-NH$_2$-Phe |
| II-36 | H | H | H | H | 3-OMe-4-NH$_2$-Phe |
| II-37 | H | H | H | H | 2-OH-4-NHMe-Phe |
| II-38 | H | H | H | H | 2-OMe-4-NHMe-Phe |
| II-39 | H | H | H | H | 3-OH-4-NHMe-Phe |
| II-40 | H | H | H | H | 3-OMe-4-NHMe-Phe |
| II-41 | H | H | H | H | 2-OH-4-NMe$_2$-Phe |
| II-42 | H | H | H | H | 2-OMe-4-NMe$_2$-Phe |
| II-43 | H | H | H | H | 3-OH-4-NMe$_2$-Phe |
| II-44 | H | H | H | H | 3-OMe-4-NMe$_2$-Phe |

TABLE 11

| Number | R¹ | R² | R³ | R⁴ | R⁷ |
|---|---|---|---|---|---|
| II-45 | H | H | OH | H | 4-NH$_2$-Phe |
| II-46 | H | H | OH | H | 4-NHMe-Phe |
| II-47 | H | H | OH | H | 4-NMe$_2$-Phe |
| II-48 | H | H | OH | H | 2-NH$_2$-Phe |
| II-49 | H | H | OH | H | 2-NHMe-Phe |
| II-50 | H | H | OH | H | 2-NMe$_2$-Phe |
| II-51 | H | H | OH | H | 3-NH$_2$-Phe |
| II-52 | H | H | OH | H | 3-NHMe-Phe |
| II-53 | H | H | OH | H | 3-NMe$_2$-Phe |
| II-54 | H | H | OH | H | 2-OH-4-NH$_2$-Phe |
| II-55 | H | H | OH | H | 2-OMe-4-NH$_2$-Phe |
| II-56 | H | H | OH | H | 3-OH-4-NH$_2$-Phe |
| II-57 | H | H | OH | H | 3-OMe-4-NH$_2$-Phe |
| II-58 | H | H | OH | H | 2-OH-4-NHMe-Phe |
| II-59 | H | H | OH | H | 2-OMe-4-NHMe-Phe |
| II-60 | H | H | OH | H | 3-OH-4-NHMe-Phe |
| II-61 | H | H | OH | H | 3-OMe-4-NHMe-Phe |
| II-62 | H | H | OH | H | 2-OH-4-NMe$_2$-Phe |
| II-63 | H | H | OH | H | 2-OMe-4-NMe$_2$-Phe |
| II-64 | H | H | OH | H | 3-OH-4-NMe$_2$-Phe |
| II-65 | H | H | OH | H | 3-OMe-4-NMe$_2$-Phe |
| II-66 | H | H | F | H | 4-NH$_2$-Phe |
| II-67 | H | H | F | H | 4-NHMe-Phe |
| II-68 | H | H | F | H | 2-NH$_2$-Phe |
| II-69 | H | H | F | H | 2-NHMe-Phe |
| II-70 | H | H | F | H | 2-NMe$_2$-Phe |
| II-71 | H | H | F | H | 3-NH$_2$-Phe |
| II-72 | H | H | F | H | 3-NHMe-Phe |
| II-73 | H | H | F | H | 3-NMe$_2$-Phe |

TABLE 11-continued

| Number | R¹ | R² | R³ | R⁴ | R⁷ |
|---|---|---|---|---|---|
| II-74 | H | H | F | H | 2-OH-4-NH$_2$-Phe |
| II-75 | H | H | F | H | 2-OMe-4-NH$_2$-Phe |
| II-76 | H | H | F | H | 3-OH-4-NH$_2$-Phe |
| II-77 | H | H | F | H | 3-OMe-4-NH$_2$-Phe |
| II-78 | H | H | F | H | 2-OH-4-NHMe-Phe |
| II-79 | H | H | F | H | 2-OMe-4-NHMe-Phe |
| II-80 | H | H | F | H | 3-OH-4-NHMe-Phe |
| II-81 | H | H | F | H | 3-OMe-4-NHMe-Phe |
| II-82 | H | H | F | H | 2-OH-4-NMe$_2$-Phe |
| II-83 | H | H | F | H | 2-OMe-4-NMe$_2$-Phe |
| II-84 | H | H | F | H | 3-OH-4-NMe$_2$-Phe |
| II-85 | H | H | F | H | 3-OMe-4-NMe$_2$-Phe |

TABLE 12

| Number | R¹ | R² | R³ | R⁴ | R⁷ |
|---|---|---|---|---|---|
| II-86 | H | H | I | H | 4-NH$_2$-Phe |
| II-87 | H | H | I | H | 4-NHMe-Phe |
| II-88 | H | H | I | H | 2-NH$_2$-Phe |
| II-89 | H | H | I | H | 2-NHMe-Phe |
| II-90 | H | H | I | H | 3-NH$_2$-Phe |
| II-91 | H | H | I | H | 3-NHMe-Phe |
| II-92 | H | H | I | H | 2-OH-4-NH$_2$-Phe |
| II-93 | H | H | I | H | 2-OMe-4-NH$_2$-Phe |
| II-94 | H | H | I | H | 3-OH-4-NH$_2$-Phe |
| II-95 | H | H | I | H | 3-OMe-4-NH$_2$-Phe |
| II-96 | H | H | I | H | 2-OH-4-NHMe-Phe |
| II-97 | H | H | I | H | 2-OMe-4-NHMe-Phe |
| II-98 | H | H | I | H | 3-OH-4-NHMe-Phe |
| II-99 | H | H | I | H | 3-OMe-4-NHMe-Phe |
| II-100 | H | H | I | H | 2-OH-4-NMe$_2$-Phe |
| II-101 | H | H | I | H | 2-OMe-4-NMe$_2$-Phe |
| II-102 | H | H | I | H | 3-OMe-4-NMe$_2$-Phe |

TABLE 13

| Number | R¹ | R² | R³ | R⁴ | R⁷ |
|---|---|---|---|---|---|
| II-103 | H | OH | H | H | 2-NH$_2$-Phe |
| II-104 | H | OH | H | H | 3-NH$_2$-Phe |
| II-105 | H | OH | H | H | 4-NH$_2$-Phe |
| II-106 | H | OH | H | H | 2-NHMe-Phe |
| II-107 | H | OH | H | H | 3-NHMe-Phe |
| II-108 | H | OH | H | H | 4-NHMe-Phe |
| II-109 | H | OH | H | H | 2-NMe$_2$-Phe |
| II-110 | H | OH | H | H | 3-NMe$_2$-Phe |
| II-111 | H | OH | H | H | 4-NMe$_2$-Phe |
| II-112 | H | OH | H | H | 2-OH-Phe |
| II-113 | H | OH | H | H | 3-OH-Phe |
| II-114 | H | OH | H | H | 4-OH-Phe |
| II-115 | H | OH | H | H | 2-OMe-Phe |
| II-116 | H | OH | H | H | 3-OMe-Phe |
| II-117 | H | OH | H | H | 4-OMe-Phe |
| II-118 | H | H | OH | H | 2-OH-Phe |
| II-119 | H | H | OH | H | 3-OH-Phe |
| II-120 | H | H | OH | H | 4-OH-Phe |
| II-121 | H | H | OH | H | 2-OMe-Phe |
| II-122 | H | H | OH | H | 3-OMe-Phe |
| II-123 | H | H | OH | H | 4-OMe-Phe |
| II-124 | H | F | H | H | 2-NH$_2$-Phe |
| II-125 | H | F | H | H | 3-NH$_2$-Phe |
| II-126 | H | F | H | H | 4-NH$_2$-Phe |
| II-127 | H | F | H | H | 2-NHMe-Phe |
| II-128 | H | F | H | H | 3-NHMe-Phe |
| II-129 | H | F | H | H | 4-NHMe-Phe |
| II-130 | H | F | H | H | 2-NMe$_2$-Phe |
| II-131 | H | F | H | H | 3-NMe$_2$-Phe |
| II-132 | H | F | H | H | 4-NMe$_2$-Phe |
| II-133 | H | F | H | H | 2-OH-Phe |
| II-134 | H | F | H | H | 3-OH-Phe |
| II-135 | H | F | H | H | 4-OH-Phe |
| II-136 | H | F | H | H | 2-OMe-Phe |

TABLE 13-continued

| Number | R¹ | R² | R³ | R⁴ | R⁷ |
|---|---|---|---|---|---|
| II-137 | H | F | H | H | 3-OMe-Phe |
| II-138 | H | F | H | H | 4-OMe-Phe |

TABLE 14

| Number | R¹ | R² | R³ | R⁴ | R⁷ |
|---|---|---|---|---|---|
| II-139 | H | H | F | H | 2-OH-Phe |
| II-140 | H | H | F | H | 3-OH-Phe |
| II-141 | H | H | F | H | 4-OH-Phe |
| II-142 | H | H | F | H | 2-OMe-Phe |
| II-143 | H | H | F | H | 3-OMe-Phe |
| II-144 | H | H | F | H | 4-OMe-Phe |
| II-145 | H | I | H | H | 2-NH₂-Phe |
| II-146 | H | I | H | H | 3-NH₂-Phe |
| II-147 | H | I | H | H | 4-NH₂-Phe |
| II-148 | H | I | H | H | 2-NHMe-Phe |
| II-149 | H | I | H | H | 3-NHMe-Phe |
| II-150 | H | I | H | H | 4-NHMe-Phe |
| II-151 | H | I | H | H | 2-NMe₂-Phe |
| II-152 | H | I | H | H | 3-NMe₂-Phe |
| II-153 | H | I | H | H | 2-OH-Phe |
| II-154 | H | I | H | H | 3-OH-Phe |
| II-155 | H | I | H | H | 4-OH-Phe |
| II-156 | H | I | H | H | 2-OMe-Phe |
| II-157 | H | I | H | H | 3-OMe-Phe |
| II-158 | H | I | H | H | 4-OMe-Phe |
| II-159 | H | H | I | H | 2-OH-Phe |
| II-160 | H | H | I | H | 3-OH-Phe |
| II-161 | H | H | I | H | 4-OH-Phe |
| II-162 | H | H | I | H | 2-OMe-Phe |
| II-163 | H | H | I | H | 3-OMe-Phe |
| II-164 | H | H | I | H | 4-OMe-Phe |

TABLE 15

| Number | R¹ | R² | R³ | R⁴ | R⁷ |
|---|---|---|---|---|---|
| II-165 | H | X1 | H | H | 2-(4-NH₂-Phe) |
| II-166 | H | X1 | H | H | 2-(4-NHMe-Phe) |
| II-167 | H | X1 | H | H | 2-(4-NMe₂-Phe) |
| II-168 | H | X1 | H | H | 2-(4-OMe-Phe) |
| II-169 | H | X1 | H | H | 2-(4-OH-Phe) |
| II-170 | H | X1 | H | H | 2-(3-NH₂-Phe) |
| II-171 | H | X1 | H | H | 2-(3-NHMe-Phe) |
| II-172 | H | X1 | H | H | 2-(3-NMe₂-Phe) |
| II-173 | H | X1 | H | H | 2-(3-OMe-Phe) |
| II-174 | H | X1 | H | H | 2-(3-OH-Phe) |
| II-175 | H | X2 | H | H | 2-(4-NH₂-Phe) |
| II-176 | H | X2 | H | H | 2-(4-NHMe-Phe) |
| II-177 | H | X2 | H | H | 2-(4-NMe₂-Phe) |
| II-178 | H | X2 | H | H | 2-(4-OMe-Phe) |
| II-179 | H | X2 | H | H | 2-(4-OH-Phe) |
| II-180 | H | X2 | H | H | 2-(3-NH₂-Phe) |
| II-181 | H | X2 | H | H | 2-(3-NHMe-Phe) |
| II-182 | H | X2 | H | H | 2-(3-NMe₂-Phe) |
| II-183 | H | X2 | H | H | 2-(3-OMe-Phe) |
| II-184 | H | X2 | H | H | 2-(3-OH-Phe) |
| II-185 | H | X3 | H | H | 2-(4-NH₂-Phe) |
| II-186 | H | X3 | H | H | 2-(4-NHMe-Phe) |
| II-187 | H | X3 | H | H | 2-(4-NMe₂-Phe) |
| II-188 | H | X3 | H | H | 2-(4-OMe-Phe) |
| II-189 | H | X3 | H | H | 2-(4-OH-Phe) |
| II-190 | H | X3 | H | H | 2-(3-NH₂-Phe) |
| II-191 | H | X3 | H | H | 2-(3-NHMe-Phe) |
| II-192 | H | X3 | H | H | 2-(3-NMe₂-Phe) |
| II-193 | H | X3 | H | H | 2-(3-OMe-Phe) |
| II-194 | H | X3 | H | H | 2-(3-OH-Phe) |
| II-195 | H | X4 | H | H | 2-(4-NH₂-Phe) |
| II-196 | H | X4 | H | H | 2-(4-NHMe-Phe) |
| II-197 | H | X4 | H | H | 2-(4-NMe₂-Phe) |
| II-198 | H | X4 | H | H | 2-(4-OMe-Phe) |
| II-199 | H | X4 | H | H | 2-(4-OH-Phe) |

TABLE 15-continued

| Number | R¹ | R² | R³ | R⁴ | R⁷ |
|---|---|---|---|---|---|
| II-200 | H | X4 | H | H | 2-(3-NH₂-Phe) |
| II-201 | H | X4 | H | H | 2-(3-NHMe-Phe) |
| II-202 | H | X4 | H | H | 2-(3-NMe₂-Phe) |
| II-203 | H | X4 | H | H | 2-(3-OMe-Phe) |
| II-204 | H | X4 | H | H | 2-(3-OH-Phe) |

TABLE 16

| Number | R¹ | R² | R³ | R⁴ | R⁷ |
|---|---|---|---|---|---|
| II-205 | H | H | X1 | H | 2-(4-NH₂-Phe) |
| II-206 | H | H | X1 | H | 2-(4-NHMe-Phe) |
| II-207 | H | H | X1 | H | 2-(4-NMe₂-Phe) |
| II-208 | H | H | X1 | H | 2-(4-OMe-Phe) |
| II-209 | H | H | X1 | H | 2-(4-OH-Phe) |
| II-210 | H | H | X1 | H | 2-(3-NH₂-Phe) |
| II-211 | H | H | X1 | H | 2-(3-NHMe-Phe) |
| II-212 | H | H | X1 | H | 2-(3-NMe₂-Phe) |
| II-213 | H | H | X1 | H | 2-(3-OMe-Phe) |
| II-214 | H | H | X1 | H | 2-(3-OH-Phe) |
| II-215 | H | H | X2 | H | 2-(4-NH₂-Phe) |
| II-216 | H | H | X2 | H | 2-(4-NHMe-Phe) |
| II-217 | H | H | X2 | H | 2-(4-NMe₂-Phe) |
| II-218 | H | H | X2 | H | 2-(4-OMe-Phe) |
| II-219 | H | H | X2 | H | 2-(4-OH-Phe) |
| II-220 | H | H | X2 | H | 2-(3-NH₂-Phe) |
| II-221 | H | H | X2 | H | 2-(3-NHMe-Phe) |
| II-222 | H | H | X2 | H | 2-(3-NMe₂-Phe) |
| II-223 | H | H | X2 | H | 2-(3-OMe-Phe) |
| II-224 | H | H | X2 | H | 2-(3-OH-Phe) |
| II-225 | H | H | X3 | H | 2-(4-NH₂-Phe) |
| II-226 | H | H | X3 | H | 2-(4-NHMe-Phe) |
| II-227 | H | H | X3 | H | 2-(4-NMe₂-Phe) |
| II-228 | H | H | X3 | H | 2-(4-OMe-Phe) |
| II-229 | H | H | X3 | H | 2-(4-OH-Phe) |
| II-230 | H | H | X3 | H | 2-(3-NH₂-Phe) |
| II-231 | H | H | X3 | H | 2-(3-NHMe-Phe) |
| II-232 | H | H | X3 | H | 2-(3-NMe₂-Phe) |
| II-233 | H | H | X3 | H | 2-(3-OMe-Phe) |
| II-234 | H | H | X3 | H | 2-(3-OH-Phe) |
| II-235 | H | H | X4 | H | 2-(4-NH₂-Phe) |
| II-236 | H | H | X4 | H | 2-(4-NHMe-Phe) |
| II-237 | H | H | X4 | H | 2-(4-NMe₂-Phe) |
| II-238 | H | H | X4 | H | 2-(4-OMe-Phe) |
| II-239 | H | H | X4 | H | 2-(4-OH-Phe) |
| II-240 | H | H | X4 | H | 2-(3-NH₂-Phe) |
| II-241 | H | H | X4 | H | 2-(3-NHMe-Phe) |
| II-242 | H | H | X4 | H | 2-(3-NMe₂-Phe) |
| II-243 | H | H | X4 | H | 2-(3-OMe-Phe) |
| II-244 | H | H | X4 | H | 2-(3-OH-Phe) |

TABLE 17

| Number | R¹ | R² | R³ | R⁴ | R⁷ |
|---|---|---|---|---|---|
| II-245 | H | NH₂ | H | H | 4-I-Phe |
| II-246 | H | NH₂ | H | H | 4-F-Phe |
| II-247 | H | NH₂ | H | H | 4-OH-Phe |
| II-248 | H | NH₂ | H | H | 4-X1-Phe |
| II-249 | H | NH₂ | H | H | 4-X2-Phe |
| II-250 | H | NH₂ | H | H | 4-X3-Phe |
| II-251 | H | NH₂ | H | H | 4-X4-Phe |
| II-252 | H | NH₂ | H | H | 3-I-Phe |
| II-253 | H | NH₂ | H | H | 3-F-Phe |
| II-254 | H | NH₂ | H | H | 3-OH-Phe |
| II-255 | H | NH₂ | H | H | 3-X1-Phe |
| II-256 | H | NH₂ | H | H | 3-X2-Phe |
| II-257 | H | NH₂ | H | H | 3-X3-Phe |
| II-258 | H | NH₂ | H | H | 3-X4-Phe |
| II-259 | H | NHMe | H | H | 4-I-Phe |
| II-260 | H | NHMe | H | H | 4-F-Phe |
| II-261 | H | NHMe | H | H | 4-OH-Phe |
| II-262 | H | NHMe | H | H | 4-X1-Phe |

TABLE 17-continued

| Number | $R^1$ | $R^2$ | $R^3$ | $R^4$ | $R^7$ |
|---|---|---|---|---|---|
| II-263 | H | NHMe | H | H | 4-X2-Phe |
| II-264 | H | NHMe | H | H | 4-X3-Phe |
| II-265 | H | NHMe | H | H | 4-X4-Phe |
| II-266 | H | NHMe | H | H | 3-I-Phe |
| II-267 | H | NHMe | H | H | 3-F-Phe |
| II-268 | H | NHMe | H | H | 3-OH-Phe |
| II-269 | H | NHMe | H | H | 3-X1-Phe |
| II-270 | H | NHMe | H | H | 3-X2-Phe |
| II-271 | H | NHMe | H | H | 3-X3-Phe |
| II-272 | H | NHMe | H | H | 3-X4-Phe |
| II-273 | H | $NMe_2$ | H | H | 4-I-Phe |
| II-274 | H | $NMe_2$ | H | H | 4-F-Phe |
| II-275 | H | $NMe_2$ | H | H | 4-OH-Phe |
| II-276 | H | $NMe_2$ | H | H | 4-X1-Phe |
| II-277 | H | $NMe_2$ | H | H | 4-X2-Phe |
| II-278 | H | $NMe_2$ | H | H | 4-X3-Phe |
| II-279 | H | $NMe_2$ | H | H | 4-X4-Phe |
| II-280 | H | $NMe_2$ | H | H | 3-I-Phe |
| II-281 | H | $NMe_2$ | H | H | 3-F-Phe |
| II-282 | H | $NMe_2$ | H | H | 3-OH-Phe |
| II-283 | H | $NMe_2$ | H | H | 3-X1-Phe |
| II-284 | H | $NMe_2$ | H | H | 3-X2-Phe |
| II-285 | H | $NMe_2$ | H | H | 3-X3-Phe |
| II-286 | H | $NMe_2$ | H | H | 3-X4-Phe |

TABLE 18

| Number | $R^1$ | $R^2$ | $R^3$ | $R^4$ | $R^7$ |
|---|---|---|---|---|---|
| II-287 | H | OMe | H | H | 4-I-Phe |
| II-288 | H | OMe | H | H | 4-F-Phe |
| II-289 | H | OMe | H | H | 4-OH-Phe |
| II-290 | H | OMe | H | H | 4-X1-Phe |
| II-291 | H | OMe | H | H | 4-X2-Phe |
| II-292 | H | OMe | H | H | 4-X3-Phe |
| II-293 | H | OMe | H | H | 4-X4-Phe |
| II-294 | H | OMe | H | H | 3-I-Phe |
| II-295 | H | OMe | H | H | 3-F-Phe |
| II-296 | H | OMe | H | H | 3-OH-Phe |
| II-297 | H | OMe | H | H | 3-X1-Phe |
| II-298 | H | OMe | H | H | 3-X2-Phe |
| II-299 | H | OMe | H | H | 3-X3-Phe |
| II-300 | H | OMe | H | H | 3-X4-Phe |
| II-301 | H | OH | H | H | 4-I-Phe |
| II-302 | H | OH | H | H | 4-F-Phe |
| II-303 | H | OH | H | H | 4-OH-Phe |
| II-304 | H | OH | H | H | 4-X1-Phe |
| II-305 | H | OH | H | H | 4-X2-Phe |
| II-306 | H | OH | H | H | 4-X3-Phe |
| II-307 | H | OH | H | H | 4-X4-Phe |
| II-308 | H | OH | H | H | 3-I-Phe |
| II-309 | H | OH | H | H | 3-F-Phe |
| II-310 | H | OH | H | H | 3-OH-Phe |
| II-311 | H | OH | H | H | 3-X1-Phe |
| II-312 | H | OH | H | H | 3-X2-Phe |
| II-313 | H | OH | H | H | 3-X3-Phe |
| II-314 | H | OH | H | H | 3-X4-Phe |

TABLE 19

| Number | $R^1$ | $R^2$ | $R^3$ | $R^4$ | $R^7$ |
|---|---|---|---|---|---|
| II-315 | H | H | $NH_2$ | H | 4-I-Phe |
| II-316 | H | H | $NH_2$ | H | 4-F-Phe |
| II-317 | H | H | $NH_2$ | H | 4-OH-Phe |
| II-318 | H | H | $NH_2$ | H | 4-X1-Phe |
| II-319 | H | H | $NH_2$ | H | 4-X2-Phe |
| II-320 | H | H | $NH_2$ | H | 4-X3-Phe |
| II-321 | H | H | $NH_2$ | H | 4-X4-Phe |
| II-322 | H | H | $NH_2$ | H | 3-I-Phe |
| II-323 | H | H | $NH_2$ | H | 3-F-Phe |
| II-324 | H | H | $NH_2$ | H | 3-OH-Phe |
| II-325 | H | H | $NH_2$ | H | 3-X1-Phe |
| II-326 | H | H | $NH_2$ | H | 3-X2-Phe |
| II-327 | H | H | $NH_2$ | H | 3-X3-Phe |
| II-328 | H | H | $NH_2$ | H | 3-X4-Phe |
| II-329 | H | H | NHMe | H | 4-I-Phe |
| II-330 | H | H | NHMe | H | 4-F-Phe |
| II-331 | H | H | NHMe | H | 4-OH-Phe |
| II-332 | H | H | NHMe | H | 4-X1-Phe |
| II-333 | H | H | NHMe | H | 4-X2-Phe |
| II-334 | H | H | NHMe | H | 4-X3-Phe |
| II-335 | H | H | NHMe | H | 4-X4-Phe |
| II-336 | H | H | NHMe | H | 3-I-Phe |
| II-337 | H | H | NHMe | H | 3-F-Phe |
| II-338 | H | H | NHMe | H | 3-OH-Phe |
| II-339 | H | H | NHMe | H | 3-X1-Phe |
| II-340 | H | H | NHMe | H | 3-X2-Phe |
| II-341 | H | H | NHMe | H | 3-X3-Phe |
| II-342 | H | H | NHMe | H | 3-X4-Phe |
| II-343 | H | H | $NMe_2$ | H | 4-I-Phe |
| II-344 | H | H | $NMe_2$ | H | 4-F-Phe |
| II-345 | H | H | $NMe_2$ | H | 4-OH-Phe |
| II-346 | H | H | $NMe_2$ | H | 4-X1-Phe |
| II-347 | H | H | $NMe_2$ | H | 4-X2-Phe |
| II-348 | H | H | $NMe_2$ | H | 4-X3-Phe |
| II-349 | H | H | $NMe_2$ | H | 4-X4-Phe |
| II-350 | H | H | $NMe_2$ | H | 3-I-Phe |
| II-351 | H | H | $NMe_2$ | H | 3-F-Phe |
| II-352 | H | H | $NMe_2$ | H | 3-OH-Phe |
| II-353 | H | H | $NMe_2$ | H | 3-X1-Phe |
| II-354 | H | H | $NMe_2$ | H | 3-X2-Phe |
| II-355 | H | H | $NMe_2$ | H | 3-X3-Phe |
| II-356 | H | H | $NMe_2$ | H | 3-X4-Phe |

TABLE 20

| Number | $R^1$ | $R^2$ | $R^3$ | $R^4$ | $R^7$ |
|---|---|---|---|---|---|
| II-357 | H | H | OMe | H | 4-I-Phe |
| II-358 | H | H | OMe | H | 4-F-Phe |
| II-359 | H | H | OMe | H | 4-OH-Phe |
| II-360 | H | H | OMe | H | 4-X1-Phe |
| II-361 | H | H | OMe | H | 4-X2-Phe |
| II-362 | H | H | OMe | H | 4-X3-Phe |
| II-363 | H | H | OMe | H | 4-X4-Phe |
| II-364 | H | H | OMe | H | 3-I-Phe |
| II-365 | H | H | OMe | H | 3-F-Phe |
| II-366 | H | H | OMe | H | 3-OH-Phe |
| II-367 | H | H | OMe | H | 3-X1-Phe |
| II-368 | H | H | OMe | H | 3-X2-Phe |
| II-369 | H | H | OMe | H | 3-X3-Phe |
| II-370 | H | H | OMe | H | 3-X4-Phe |
| II-371 | H | H | OH | H | 4-I-Phe |
| II-372 | H | H | OH | H | 4-F-Phe |
| II-373 | H | H | OH | H | 4-OH-Phe |
| II-374 | H | H | OH | H | 4-X1-Phe |
| II-375 | H | H | OH | H | 4-X2-Phe |
| II-376 | H | H | OH | H | 4-X3-Phe |
| II-377 | H | H | OH | H | 4-X4-Phe |
| II-378 | H | H | OH | H | 3-I-Phe |
| II-379 | H | H | OH | H | 3-F-Phe |
| II-380 | H | H | OH | H | 3-OH-Phe |
| II-381 | H | H | OH | H | 3-X1-Phe |
| II-382 | H | H | OH | H | 3-X2-Phe |
| II-383 | H | H | OH | H | 3-X3-Phe |
| II-384 | H | H | OH | H | 3-X4-Phe |

Among the aforementioned compounds, preferred compounds may include compound II-7 (compound 31) and compound II-2 (compound 36).

Representative compounds among the compounds represented by general formula (III) are shown in Tables 21 to 28.

TABLE 21

| Number | R¹ | R² | R³ | R⁴ | R⁸ |
|---|---|---|---|---|---|
| III-1 | H | H | I | H | 4-NH$_2$-Phe |
| III-2 | H | H | I | H | 4-NHMe-Phe |
| III-3 | H | H | I | H | 4-NMe$_2$-Phe |
| III-4 | H | H | F | H | 4-NH$_2$-Phe |
| III-5 | H | H | F | H | 4-NHMe-Phe |
| III-6 | H | H | F | H | 4-NMe$_2$-Phe |
| III-7 | I | H | H | H | 4-NH$_2$-Phe |
| III-8 | I | H | H | H | 4-NHMe-Phe |
| III-9 | I | H | H | H | 4-NMe$_2$-Phe |
| III-10 | H | I | H | H | 4-NH$_2$-Phe |
| III-11 | H | I | H | H | 4-NHMe-Phe |
| III-12 | H | I | H | H | 4-NMe$_2$-Phe |
| III-13 | H | H | H | I | 4-NH$_2$-Phe |
| III-14 | H | H | H | I | 4-NHMe-Phe |
| III-15 | H | H | H | I | 4-NMe$_2$-Phe |
| III-16 | H | H | I | OH | 4-NH$_2$-Phe |
| III-17 | H | H | I | OH | 4-NHMe-Phe |
| III-18 | H | H | I | OH | 4-NMe$_2$-Phe |
| III-19 | H | OH | I | OH | 4-NH$_2$-Phe |
| III-20 | H | OH | I | OH | 4-NHMe-Phe |
| III-21 | H | OH | I | OH | 4-NMe$_2$-Phe |
| III-22 | H | H | I | H | 6-NH$_2$-pyridine-3-yl |
| III-23 | H | H | I | H | 6-NHMe-pyridine-3-yl |
| III-24 | H | H | I | H | 6-NMe$_2$-pyridine-3-yl |
| III-25 | H | H | I | H | 2-NH$_2$-Phe |
| III-26 | H | H | I | H | 2-NHMe-Phe |
| III-27 | H | H | I | H | 2-NMe$_2$-Phe |
| III-28 | H | H | I | H | 3-NH$_2$-Phe |
| III-29 | H | H | I | H | 3-NHMe-Phe |
| III-30 | H | H | I | H | 3-NMe$_2$-Phe |
| III-31 | H | H | I | H | 3-OH-4-NH$_2$-Phe |
| III-32 | H | H | I | H | 3-OH-4-NHMe-Phe |
| III-33 | H | H | I | H | 3-OH-4-NMe$_2$-Phe |
| III-34 | H | H | I | H | 3,5-OH-4-NH$_2$-Phe |
| III-35 | H | H | I | H | 3,5-OH-4-NHMe-Phe |
| III-36 | H | H | I | H | 3,5-OH-4-NMe$_2$-Phe |
| III-37 | H | H | H | H | 4-NH$_2$-Phe |
| III-38 | H | H | H | H | 4-NHMe-Phe |
| III-39 | H | H | H | H | 4-NMe$_2$-Phe |
| III-40 | H | H | H | H | 2-NH$_2$-Phe |
| III-41 | H | H | H | H | 2-NHMe-Phe |
| III-42 | H | H | H | H | 2-NMe$_2$-Phe |
| III-43 | H | H | H | H | 3-NH$_2$-Phe |
| III-44 | H | H | H | H | 3-NHMe-Phe |
| III-45 | H | H | H | H | 3-NMe$_2$-Phe |
| III-46 | H | H | H | H | 2-OH-4-NH$_2$-Phe |
| III-47 | H | H | H | H | 2-OMe-4-NH$_2$-Phe |
| III-48 | H | H | H | H | 3-OH-4-NH$_2$-Phe |
| III-49 | H | H | H | H | 3-OMe-4-NH$_2$-Phe |
| III-50 | H | H | H | H | 2-OH-4-NHMe-Phe |
| III-51 | H | H | H | H | 2-OMe-4-NHMe-Phe |
| III-52 | H | H | H | H | 3-OH-4-NHMe-Phe |
| III-53 | H | H | H | H | 3-OMe-4-NHMe-Phe |
| III-54 | H | H | H | H | 2-OH-4-NMe$_2$-Phe |
| III-55 | H | H | H | H | 2-OMe-4-NMe$_2$-Phe |
| III-56 | H | H | H | H | 3-OH-4-NMe$_2$-Phe |
| III-57 | H | H | H | H | 3-OMe-4-NMe$_2$-Phe |

TABLE 22

| Number | R¹ | R² | R³ | R⁴ | R⁸ |
|---|---|---|---|---|---|
| III-58 | H | H | OH | H | 4-NH$_2$-Phe |
| III-59 | H | H | OH | H | 4-NHMe-Phe |
| III-60 | H | H | OH | H | 4-NMe$_2$-Phe |
| III-61 | H | H | OH | H | 2-NH$_2$-Phe |
| III-62 | H | H | OH | H | 2-NHMe-Phe |
| III-63 | H | H | OH | H | 2-NMe$_2$-Phe |
| III-64 | H | H | OH | H | 3-NH$_2$-Phe |
| III-65 | H | H | OH | H | 3-NHMe-Phe |
| III-66 | H | H | OH | H | 3-NMe$_2$-Phe |
| III-67 | H | H | OH | H | 2-OH-4-NH$_2$-Phe |
| III-68 | H | H | OH | H | 2-OMe-4-NH$_2$-Phe |
| III-69 | H | H | OH | H | 3-OH-4-NH$_2$-Phe |
| III-70 | H | H | OH | H | 3-OMe-4-NH$_2$-Phe |
| III-71 | H | H | OH | H | 2-OH-4-NHMe-Phe |
| III-72 | H | H | OH | H | 2-OMe-4-NHMe-Phe |
| III-73 | H | H | OH | H | 3-OH-4-NHMe-Phe |
| III-74 | H | H | OH | H | 3-OMe-4-NHMe-Phe |
| III-75 | H | H | OH | H | 2-OH-4-NMe$_2$-Phe |
| III-76 | H | H | OH | H | 2-OMe-4-NMe$_2$-Phe |
| III-77 | H | H | OH | H | 3-OH-4-NMe$_2$-Phe |
| III-78 | H | H | OH | H | 3-OMe-4-NMe$_2$-Phe |
| III-79 | H | H | F | H | 2-NH$_2$-Phe |
| III-80 | H | H | F | H | 2-NHMe-Phe |
| III-81 | H | H | F | H | 2-NMe$_2$-Phe |
| III-82 | H | H | F | H | 3-NH$_2$-Phe |
| III-83 | H | H | F | H | 3-NHMe-Phe |
| III-84 | H | H | F | H | 3-NMe$_2$-Phe |
| III-85 | H | H | F | H | 2-OH-4-NH$_2$-Phe |
| III-86 | H | H | F | H | 2-OMe-4-NH$_2$-Phe |
| III-87 | H | H | F | H | 3-OH-4-NH$_2$-Phe |
| III-88 | H | H | F | H | 3-OMe-4-NH$_2$-Phe |
| III-89 | H | H | F | H | 2-OH-4-NHMe-Phe |
| III-90 | H | H | F | H | 2-OMe-4-NHMe-Phe |
| III-91 | H | H | F | H | 3-OH-4-NHMe-Phe |
| III-92 | H | H | F | H | 3-OMe-4-NHMe-Phe |
| III-93 | H | H | F | H | 2-OH-4-NMe$_2$-Phe |
| III-94 | H | H | F | H | 2-OMe-4-NMe$_2$-Phe |
| III-95 | H | H | F | H | 3-OH-4-NMe$_2$-Phe |
| III-96 | H | H | F | H | 3-OMe-4-NMe$_2$-Phe |

TABLE 23

| Number | R¹ | R² | R³ | R⁴ | R⁸ |
|---|---|---|---|---|---|
| III-97 | H | H | I | H | 2-OH-4-NH$_2$-Phe |
| III-98 | H | H | I | H | 2-OMe-4-NH$_2$-Phe |
| III-99 | H | H | I | H | 3-OMe-4-NH$_2$-Phe |
| III-100 | H | H | I | H | 2-OH-4-NHMe-Phe |
| III-101 | H | H | I | H | 2-OMe-4-NHMe-Phe |
| III-102 | H | H | I | H | 3-OMe-4-NHMe-Phe |
| III-103 | H | H | I | H | 2-OH-4-NMe$_2$-Phe |
| III-104 | H | H | I | H | 2-OMe-4-NMe$_2$-Phe |
| III-105 | H | H | I | H | 3-OMe-4-NMe$_2$-Phe |

TABLE 24

| Number | R¹ | R² | R³ | R⁴ | R⁸ |
|---|---|---|---|---|---|
| III-106 | H | OH | H | H | 2-NH$_2$-Phe |
| III-107 | H | OH | H | H | 3-NH$_2$-Phe |
| III-108 | H | OH | H | H | 4-NH$_2$-Phe |
| III-109 | H | OH | H | H | 2-NHMe-Phe |
| III-110 | H | OH | H | H | 3-NHMe-Phe |
| III-111 | H | OH | H | H | 4-NHMe-Phe |
| III-112 | H | OH | H | H | 2-NMe$_2$-Phe |
| III-113 | H | OH | H | H | 3-NMe$_2$-Phe |
| III-114 | H | OH | H | H | 4-NMe$_2$-Phe |
| III-115 | H | OH | H | H | 2-OH-Phe |
| III-116 | H | OH | H | H | 3-OH-Phe |
| III-117 | H | OH | H | H | 4-OH-Phe |
| III-118 | H | OH | H | H | 2-OMe-Phe |
| III-119 | H | OH | H | H | 3-OMe-Phe |
| III-120 | H | OH | H | H | 4-OMe-Phe |
| III-121 | H | H | OH | H | 2-OH-Phe |
| III-122 | H | H | OH | H | 3-OH-Phe |
| III-123 | H | H | OH | H | 4-OH-Phe |
| III-124 | H | H | OH | H | 2-OMe-Phe |
| III-125 | H | H | OH | H | 3-OMe-Phe |
| III-126 | H | H | OH | H | 4-OMe-Phe |
| III-127 | H | F | H | H | 2-NH$_2$-Phe |
| III-128 | H | F | H | H | 3-NH$_2$-Phe |
| III-129 | H | F | H | H | 4-NH$_2$-Phe |
| III-130 | H | F | H | H | 2-NHMe-Phe |
| III-131 | H | F | H | H | 3-NHMe-Phe |
| III-132 | H | F | H | H | 4-NHMe-Phe |
| III-133 | H | F | H | H | 2-NMe$_2$-Phe |

TABLE 24-continued

| Number | R¹ | R² | R³ | R⁴ | R⁸ |
|---|---|---|---|---|---|
| III-134 | H | F | H | H | 3-NMe$_2$-Phe |
| III-135 | H | F | H | H | 4-NMe$_2$-Phe |
| III-136 | H | F | H | H | 2-OH-Phe |
| III-137 | H | F | H | H | 3-OH-Phe |
| III-138 | H | F | H | H | 4-OH-Phe |
| III-139 | H | F | H | H | 2-OMe-Phe |
| III-140 | H | F | H | H | 3-OMe-Phe |
| III-141 | H | F | H | H | 4-OMe-Phe |

TABLE 25

| Number | R¹ | R² | R³ | R⁴ | R⁸ |
|---|---|---|---|---|---|
| III-142 | H | H | F | H | 2-NH$_2$-Phe |
| III-143 | H | H | F | H | 3-NH$_2$-Phe |
| III-144 | H | H | F | H | 2-OH-Phe |
| III-145 | H | H | F | H | 3-OH-Phe |
| III-146 | H | H | F | H | 4-OH-Phe |
| III-147 | H | H | F | H | 2-OMe-Phe |
| III-148 | H | H | F | H | 3-OMe-Phe |
| III-149 | H | H | F | H | 4-OMe-Phe |
| III-150 | H | I | H | H | 2-NH$_2$-Phe |
| III-151 | H | I | H | H | 3-NH$_2$-Phe |
| III-152 | H | I | H | H | 2-NHMe-Phe |
| III-153 | H | I | H | H | 3-NHMe-Phe |
| III-154 | H | I | H | H | 2-NMe$_2$-Phe |
| III-155 | H | I | H | H | 3-NMe$_2$-Phe |
| III-156 | H | I | H | H | 2-OH-Phe |
| III-157 | H | I | H | H | 3-OH-Phe |
| III-158 | H | I | H | H | 4-OH-Phe |
| III-159 | H | I | H | H | 2-OMe-Phe |
| III-160 | H | I | H | H | 3-OMe-Phe |
| III-161 | H | I | H | H | 4-OMe-Phe |
| III-162 | H | H | I | H | 2-OH-Phe |
| III-163 | H | H | I | H | 3-OH-Phe |
| III-164 | H | H | I | H | 4-OH-Phe |
| III-165 | H | H | I | H | 2-OMe-Phe |
| III-166 | H | H | I | H | 3-OMe-Phe |
| III-167 | H | H | I | H | 4-OMe-Phe |

TABLE 26

| Number | R¹ | R² | R³ | R⁴ | R⁸ |
|---|---|---|---|---|---|
| III-168 | X1 | H | H | H | 4-NH$_2$-Phe |
| III-169 | X1 | H | H | H | 4-NHMe-Phe |
| III-170 | X1 | H | H | H | 4-NMe$_2$-Phe |
| III-171 | X1 | H | H | H | 4-OMe-Phe |
| III-172 | X1 | H | H | H | 4-OH-Phe |
| III-173 | X1 | H | H | H | 3-NH$_2$-Phe |
| III-174 | X1 | H | H | H | 3-NHMe-Phe |
| III-175 | X1 | H | H | H | 3-NMe$_2$-Phe |
| III-176 | X1 | H | H | H | 3-OMe-Phe |
| III-177 | X1 | H | H | H | 3-OH-Phe |
| III-178 | X2 | H | H | H | 4-NH$_2$-Phe |
| III-179 | X2 | H | H | H | 4-NHMe-Phe |
| III-180 | X2 | H | H | H | 4-NMe$_2$-Phe |
| III-181 | X2 | H | H | H | 4-OMe-Phe |
| III-182 | X2 | H | H | H | 4-OH-Phe |
| III-183 | X2 | H | H | H | 3-NH$_2$-Phe |
| III-184 | X2 | H | H | H | 3-NHMe-Phe |
| III-185 | X2 | H | H | H | 3-NMe$_2$-Phe |
| III-186 | X2 | H | H | H | 3-OMe-Phe |
| III-187 | X2 | H | H | H | 3-OH-Phe |
| III-188 | X3 | H | H | H | 4-NH$_2$-Phe |
| III-189 | X3 | H | H | H | 4-NHMe-Phe |
| III-190 | X3 | H | H | H | 4-NMe$_2$-Phe |
| III-191 | X3 | H | H | H | 4-OMe-Phe |
| III-192 | X3 | H | H | H | 4-OH-Phe |
| III-193 | X3 | H | H | H | 3-NH$_2$-Phe |
| III-194 | X3 | H | H | H | 3-NHMe-Phe |
| III-195 | X3 | H | H | H | 3-NMe$_2$-Phe |
| III-196 | X3 | H | H | H | 3-OMe-Phe |

TABLE 26-continued

| Number | R¹ | R² | R³ | R⁴ | R⁸ |
|---|---|---|---|---|---|
| III-197 | X3 | H | H | H | 3-OH-Phe |
| III-198 | X4 | H | H | H | 4-NH$_2$-Phe |
| III-199 | X4 | H | H | H | 4-NHMe-Phe |
| III-200 | X4 | H | H | H | 4-NMe$_2$-Phe |
| III-201 | X4 | H | H | H | 4-OMe-Phe |
| III-202 | X4 | H | H | H | 4-OH-Phe |
| III-203 | X4 | H | H | H | 3-NH$_2$-Phe |
| III-204 | X4 | H | H | H | 3-NHMe-Phe |
| III-205 | X4 | H | H | H | 3-NMe$_2$-Phe |
| III-206 | X4 | H | H | H | 3-OMe-Phe |
| III-207 | X4 | H | H | H | 3-OH-Phe |

TABLE 27

| Number | R¹ | R² | R³ | R⁴ | R⁸ |
|---|---|---|---|---|---|
| III-208 | H | X1 | H | H | 4-NH$_2$-Phe |
| III-209 | H | X1 | H | H | 4-NHMe-Phe |
| III-210 | H | X1 | H | H | 4-NMe$_2$-Phe |
| III-211 | H | X1 | H | H | 4-OMe-Phe |
| III-212 | H | X1 | H | H | 4-OH-Phe |
| III-213 | H | X1 | H | H | 3-NH$_2$-Phe |
| III-214 | H | X1 | H | H | 3-NHMe-Phe |
| III-215 | H | X1 | H | H | 3-NMe$_2$-Phe |
| III-216 | H | X1 | H | H | 3-OMe-Phe |
| III-217 | H | X1 | H | H | 3-OH-Phe |
| III-218 | H | X2 | H | H | 4-NH$_2$-Phe |
| III-219 | H | X2 | H | H | 4-NHMe-Phe |
| III-220 | H | X2 | H | H | 4-NMe$_2$-Phe |
| III-221 | H | X2 | H | H | 4-OMe-Phe |
| III-222 | H | X2 | H | H | 4-OH-Phe |
| III-223 | H | X2 | H | H | 3-NH$_2$-Phe |
| III-224 | H | X2 | H | H | 3-NHMe-Phe |
| III-225 | H | X2 | H | H | 3-NMe$_2$-Phe |
| III-226 | H | X2 | H | H | 3-OMe-Phe |
| III-227 | H | X2 | H | H | 3-OH-Phe |
| III-228 | H | X3 | H | H | 4-NH$_2$-Phe |
| III-229 | H | X3 | H | H | 4-NHMe-Phe |
| III-230 | H | X3 | H | H | 4-NMe$_2$-Phe |
| III-231 | H | X3 | H | H | 4-OMe-Phe |
| III-232 | H | X3 | H | H | 4-OH-Phe |
| III-233 | H | X3 | H | H | 3-NH$_2$-Phe |
| III-234 | H | X3 | H | H | 3-NHMe-Phe |
| III-235 | H | X3 | H | H | 3-NMe$_2$-Phe |
| III-236 | H | X3 | H | H | 3-OMe-Phe |
| III-237 | H | X3 | H | H | 3-OH-Phe |
| III-238 | H | X4 | H | H | 4-NH$_2$-Phe |
| III-239 | H | X4 | H | H | 4-NHMe-Phe |
| III-240 | H | X4 | H | H | 4-NMe$_2$-Phe |
| III-241 | H | X4 | H | H | 4-OMe-Phe |
| III-242 | H | X4 | H | H | 4-OH-Phe |
| III-243 | H | X4 | H | H | 3-NH$_2$-Phe |
| III-244 | H | X4 | H | H | 3-NHMe-Phe |
| III-245 | H | X4 | H | H | 3-NMe$_2$-Phe |
| III-246 | H | X4 | H | H | 3-OMe-Phe |
| III-247 | H | X4 | H | H | 3-OH-Phe |

TABLE 28

| Number | R¹ | R² | R³ | R⁴ | R⁸ |
|---|---|---|---|---|---|
| III-248 | H | H | X1 | H | 4-NH$_2$-Phe |
| III-249 | H | H | X1 | H | 4-NHMe-Phe |
| III-250 | H | H | X1 | H | 4-NMe$_2$-Phe |
| III-251 | H | H | X1 | H | 4-OMe-Phe |
| III-252 | H | H | X1 | H | 4-OH-Phe |
| III-253 | H | H | X1 | H | 3-NH$_2$-Phe |
| III-254 | H | H | X1 | H | 3-NHMe-Phe |
| III-255 | H | H | X1 | H | 3-NMe$_2$-Phe |
| III-256 | H | H | X1 | H | 3-OMe-Phe |
| III-257 | H | H | X1 | H | 3-OH-Phe |
| III-258 | H | H | X2 | H | 4-NH$_2$-Phe |
| III-259 | H | H | X2 | H | 4-NHMe-Phe |

TABLE 28-continued

| Number | R¹ | R² | R³ | R⁴ | R⁸ |
|---|---|---|---|---|---|
| III-260 | H | H | X2 | H | 4-NMe₂-Phe |
| III-261 | H | H | X2 | H | 4-OMe-Phe |
| III-262 | H | H | X2 | H | 4-OH-Phe |
| III-263 | H | H | X2 | H | 3-NH₂-Phe |
| III-264 | H | H | X2 | H | 3-NHMe-Phe |
| III-265 | H | H | X2 | H | 3-NMe₂-Phe |
| III-266 | H | H | X2 | H | 3-OMe-Phe |
| III-267 | H | H | X2 | H | 3-OH-Phe |
| III-268 | H | H | X3 | H | 4-NH₂-Phe |
| III-269 | H | H | X3 | H | 4-NHMe-Phe |
| III-270 | H | H | X3 | H | 4-NMe₂-Phe |
| III-271 | H | H | X3 | H | 4-OMe-Phe |
| III-272 | H | H | X3 | H | 4-OH-Phe |
| III-273 | H | H | X3 | H | 3-NH₂-Phe |
| III-274 | H | H | X3 | H | 3-NHMe-Phe |
| III-275 | H | H | X3 | H | 3-NMe₂-Phe |
| III-276 | H | H | X3 | H | 3-OMe-Phe |
| III-277 | H | H | X3 | H | 3-OH-Phe |
| III-278 | H | H | X4 | H | 4-NH₂-Phe |
| III-279 | H | H | X4 | H | 4-NHMe-Phe |
| III-280 | H | H | X4 | H | 4-NMe₂-Phe |
| III-281 | H | H | X4 | H | 4-OMe-Phe |
| III-282 | H | H | X4 | H | 4-OH-Phe |
| III-283 | H | H | X4 | H | 3-NH₂-Phe |
| III-284 | H | H | X4 | H | 3-NHMe-Phe |
| III-285 | H | H | X4 | H | 3-NMe₂-Phe |
| III-286 | H | H | X4 | H | 3-OMe-Phe |
| III-287 | H | H | X4 | H | 3-OH-Phe |

Among the aforementioned compounds, preferred compounds may include compound III-1 (compound 65), compound III-2 (compound 66), and compound III-3 (compound 67).

The compound represented by general formula (I) or the like can be synthesized according to the descriptions of examples as given later, and the descriptions such as Marder M et al, Biochemical and Biophysical Research Communications, 223, 384-389, 1996, Marder M et al, Bioorganic & Medicinal Chemistry Letters, 7, 2003-2008, 1997, etc.

The compound represented by general formula (I) or the like is preferably labeled with a labeling substance. As such a labeling substance, a fluorescent substance, an affinity substance, and the like may be used, but a radionuclide is preferably used. The type of a radionuclide used in labeling is not particularly limited, and it can be determined as appropriate, depending on intended use. When the compound represented by general formula (I) or the like is used in diagnosis according to single photon emission computed tomography (SPECT) for example, examples of a radionuclide that can be used may include γ-ray-emitting radionuclides such as $^{99m}$Tc, $^{111}$In, $^{67}$Ga, $^{201}$Tl, $^{123}$I, or $^{133}$Xe (preferably $^{99m}$Tc and $^{123}$I). In addition, when the compound represented by general formula (I) or the like is used in diagnosis according to Positron Emission Tomography (PET) for example, examples of a radionuclide that can be used may include positron-emitting radionuclides such as $^{11}$C, $^{13}$N, $^{15}$O, $^{18}$F, $^{62}$Cu, $^{68}$Ga, or $^{76}$Br (preferably $^{11}$C, $^{13}$N, $^{15}$O, and $^{18}$F). Moreover, when the compound represented by general formula (I) or the like is administered to animals other than human, radionuclides having a longer half-life, such as $^{125}$I, may also be used. Such a radionuclide may be contained in the molecules of the compound represented by general formula (I) or the like, or may also bind to the compound represented by general formula (I) or the like.

It is also possible to use a pharmaceutically acceptable salt, instead of the compound represented by general formula (I) or the like. Examples of such a pharmaceutically acceptable salt may include alkaline metal salt (sodium salt, potassium salt, and lithium salt), alkaline-earth metal salt (calcium salt and magnesium salt), sulfate, hydrochloride, nitrate, and phosphate.

The composition of the present invention is used in the diagnosis of amyloid-related diseases. The term "amyloid-related diseases" is used herein to mean diseases caused by accumulation of an amyloid β protein. It mainly means Alzheimer's disease, but such amyloid-related diseases also include Down's syndrome and hereditary cerebral hemorrhage with amyloidosis-Dutch type (HCHWA-D). In addition, precursory symptoms that are not generally considered as "diseases" are also included in the "amyloid-related diseases" of the present invention. An example of such a precursory symptom of disease is mild degree of cognitive impairment (MC1) observed before the occurrence of Alzheimer's disease.

The diagnosis of such amyloid-related diseases using the composition of the present invention is generally carried out by administering the composition of the present invention to a subject to be diagnosed, an experimental animal, etc., then photographing the image of the brain, and then making a diagnosis based on the state (amount, distribution, etc.) of the compound represented by general formula (I) or the like in the obtained image. A method of administering the composition of the present invention is not particularly limited, and it can be determined as appropriate, depending on the type of the compound, the type of a labeling substance, and the like. In general, the composition of the present invention is administered into skin, abdominal cavity, vein, artery, or spinal cord fluid, via injection or drip infusion. The dosage of the composition of the present invention is not particularly limited, and it can be determined as appropriate, depending on the type of the compound, the type of a labeling substance, and the like. In the case of an adult, the compound represented by general formula (I) or the like is administered preferably at a dosage of $10^{-10}$ to $10^{-3}$ mg per day, and more preferably $10^{-8}$ to $10^{-5}$ mg per day.

As stated above, since the composition of the present invention is generally administered via injection or drip infusion, it may contain components, which are generally contained in such a parenteral solution or drop. Examples of such components may include liquid carriers (e.g. potassium phosphate buffer, normal saline solution, Ringer's solution, distilled water, polyethylene glycol, vegetable oil, ethanol, glycerin, dimethyl sulfoxide, propylene glycol, etc.), antibacterial agents, local anesthetics (e.g. procaine hydrochloride, dibucaine hydrochloride, etc.), buffer solutions (e.g. Tris-HCl buffer, HEPES buffer, etc.), and osmo-regulators (e.g. glucose, sorbitol, sodium chloride, etc.)

The composition of the present invention that is used for diagnosing amyloid-related diseases can also be used for the screening of a therapeutic or preventive agent for such amyloid-related diseases. For example, a test substance is administered to a model animal affected with a certain "disease" such as Alzheimer's disease, and the composition of the present invention used for diagnosing amyloid-related diseases is then administered to the above-described model animal. Thereafter, the distribution or amount of the compound represented by general formula (I) or the like contained in the brain of the above-described model animal is examined. As a result, if a significant difference (e.g. reduction in the distribution site, reduction in the amount, etc.) is detected between the above model animal and a control animal (a model animal to which a test substance has not been administered), the test substance can be a candidate to a therapeutic agent used for amyloid-related diseases. Moreover, a test substance is administered to a model animal affected with a certain "precursory symptom of disease" such as mild degree of cognitive impairment, and the composition of the present invention used for diagnosing amyloid-related diseases is then administered to the above-described model animal. Thereafter, the distribution or amount of the compound represented by general formula (I) or the like contained in the brain of the above-described model animal is examined. As a result, if a significant difference (e.g. reduction or decelerated expansion in the distribution site, decrease or decelerated increase in the amount, etc.) is detected between the above model animal and a control animal, the test substance can be a candidate to a preventive agent used for amyloid-related diseases.

Furthermore, the composition of the present invention used for diagnosing amyloid-related diseases can also be used for evaluation of a therapeutic or preventive agent for amyloid-related diseases, the effects of which have already been confirmed. That is to say, the above-described therapeutic or preventive agent for amyloid-related diseases is administered to a model animal affected with the amyloid-related disease, and the composition of the present invention used for diagnosing amyloid-related diseases is then administered to the above-described model animal. Thereafter, the distribution or amount of the compound represented by general formula (I) or the like contained in the brain of the above-described model animal is examined. From the obtained results, the above-described therapeutic or preventive agent is evaluated (specifically, an effective dosage, an effective administration method, and the like, are analyzed).

EXAMPLES

The present invention will be described more in detail in the following examples.
[Experimental Method]
Reagents/Apparatuses IODINE-125 (74 MBq) manufactured by Amersham Biosciences was used as radioiodine-125 ($^{125}$I). Reversed-phase HPLC was carried out at a flow rate of 1.0 ml/min, employing Cosmosil 5$C_{18}$-AR column (4.6×150 mm) manufactured by Nacalai Tesque, Inc., using an elution solvent consisting of extra pure water (A) and acetonitrile (B) (A:B=40:60). $^1$H-NMR was measured employing Varian Gemini 300 using tetramethylsilane as an internal standard substance. Mass spectrometry was measured using. JEOL IMS-DX300. The amyloid β protein (Human, 1-40) [HCl form] and the amyloid β protein (Human, 1-42) [TFA form] were purchased from Peptide Institute, Inc. As other reagents, reagent chemicals were used.

(1) Synthesis of Flavone Derivative

Synthesis of 4-nitrobenzoic acid 2-acetyl-4-bromophenyl ester

5'-bromo-2'-hydroxyacetophenone (compound 1) (863 mg, 4.65 mmol) was added to a pyridine solution (20 ml) that contained 4-nitrobenzoyl chloride (1.00 g, 4.65 mmol) in an ice bath. The obtained mixture was reacted at room temperature for 30 minutes, and the reaction solution was then poured into 1 N hydrochloric acid under cooling on ice. The obtained mixture was intensively stirred. The obtained precipitate was collected by filtration, and the filtrate was then washed with purified water, so as to obtain a product of interest, 4-nitrobenzoic acid 2-acetyl-4-bromophenyl ester (compound 2). Yield: 1.57 g (yield constant: 92.7%) $^1$H NMR (300 MHz, CDCl$_3$) δ 8.37 (s, 4H), 8.00 (s, 1H), 7.76-7.72 (m, 1H), 7.16 (d, J=8.7 Hz, 1H), 2.55 (s, 3H). MS m/z 365 (MH$^+$).

Synthesis of 1-(5-bromo-2-hydroxyphenyl)-3-(4-nitrophenyl)propan-1,3-dione

Compound 2 (2.31 g, 6.34 mmol) was dissolved in pyridine (40 ml), and the obtained solution was heated up to 50° C. Thereafter, crushed potassium hydroxide (530 mg, 9.45 mmol) was added to the above solution, and the obtained mixture was then stirred for 15 minutes. Thereafter, the resultant was cooled on ice, and a 10% acetic acid solution was then added thereto. The obtained light yellow precipitate was collected by filtration, so as to obtain a product of interest, 1-(5-bromo-2-hydroxyphenyl)-3-(4-nitrophenyl)propan-1,3-dione (compound 3). Yield: 2.01 g (yield constant: 87.1%) $^1$H NMR (300 MHz, CDCl$_3$) δ11.85 (s, 1H), 8.36 (d, J=9.0 Hz, 2H), 8.13 (d, J=9.0 Hz, 2H), 7.88 (s, 1H), 7.57 (d, J=9.0 Hz, 1H), 6.95 (d, J=9.0 Hz, 1H), 6.83 (s, 2H). MS m/z 365 (MH$^+$).

Synthesis of 6-bromo-4'-nitroflavone

A mixed solution consisting of compound 3 (2.00 g, 5.49 mmol), concentrated sulfuric acid (0.5 ml), and acetic acid (40 ml) was heated to reflux for 1 hour. The temperature of the resultant was returned to room temperature, and ice pieces were then added to the reaction solution. The precipitated crystal was collected by filtration, so as to obtain a product of interest, 6-bromo-4'-nitroflavone (compound 4). Yield: 1.79 g (yield constant: 94.2%) MS m/z 347 (MH$^+$).

Synthesis of 6-bromo-4'-aminoflavone

Tin(II) chloride (275 mg, 1.45 mmol) was slowly added to an ethanol solution (7 ml) that contained compound 4 (100 mg, 0.289 mmol), while stirring. The obtained mixture was heated to reflux for 1 hour. After completion of the reaction, a 1 N sodium hydroxide aqueous solution (50 ml) was added to the reaction solution, and the obtained mixture was then extracted with 50 ml (25 ml×2) of ethyl acetate. The extract was dried over anhydrous sodium sulfate, and the solvent was then distilled away under reduced pressure, so as to obtain a product of interest, 6-bromo-4'-aminoflavone (compound 5) in the form of a yellow crystal. Yield: 77 mg (yield constant: 84.3%) $^1$H NMR (300 MHz, CDCl$_3$) δ8.36 (s, 1H), 7.72-7.76 (m, 3H), 7.44 (d, J=9.0 Hz, 1H), 6.72 (d, J=8.7 Hz, 2H), 6.70 (s, 1H), 4.15 (s, 2H). MS m/z 317 (MH$^+$).

Synthesis of 6-bromo-4'-methylaminoflavone

A sodium methylate-methanol solution (0.27 ml) was slowly added dropwise to a methanol solution (15 ml) that contained compound 5 (300 mg, 0.949 mmol) and paraformaldehyde (154 mg, 5.13 mmol), while stirring. The obtained mixture was heated to reflux for 1 hour. Thereafter, sodium borohydride (180 mg, 4.75 mmol) that was in the form of a solid was added to the reaction solution by slow degrees, and the obtained mixture was further heated to reflux for 2 hours. Thereafter, the reaction solvent was distilled away under reduced pressure, and the residue was then subjected to silica gel column chromatography using ethyl acetate/hexane (3/5) as an elution solvent, so as to obtain a product of interest, 6-bromo-4'-methylaminoflavone (compound 6). Yield: 121 mg (yield constant: 38.6%) $^1$H NMR (300 MHz, CDCl$_3$)

δ8.31 (s, 1H), 7.69-7.75 (m, 3H), 7.39 (d, J=8.7 Hz, 1H), 6.62-6.66 (m, 3H), 4.18 (s, 1H). 2.91 (s, 3H).

Synthesis of 6-bromo-4'-dimethylaminoflavone

Sodium cyanoborohydride (74.5 mg, 1.19 mmol) was slowly added dropwise to an acetic acid solution (10 ml) that contained compound 5 (75 mg, 0.237 mmol) and paraformaldehyde (71.1 mg, 2.37 mmol), while stirring. The obtained mixture was stirred at room temperature for 3 hours. After completion of the reaction, 50 ml of a 1 N sodium hydroxide aqueous solution was added to the reaction solution, and the obtained mixture was then extracted with 50 ml (25 ml×2) of chloroform. The extract was dried over anhydrous sodium sulfate, and the solvent was then distilled away under reduced pressure, so as to obtain a product of interest, 6-bromo-4'-dimethylaminoflavone (compound 7) in the form of a yellow crystal. Yield: 70 mg (yield constant: 85.7%) $^1$H NMR (300 MHz, CDCl$_3$) δ8.34 (s, 1H), 7.72-7.82 (m, 3H), 7.43 (d, J=9.0 Hz, 1H), 6.70-6.77 (m, 3H), 3.08 (s, 6H). MS m/z 345 (M$^+$).

Synthesis of 6-(tributylstannyl)-4'-methylaminoflavone

Bis(tributyltin) (0.55 ml), tetrakistriphenylphosphine palladium (41 mg, 0.035 mmol), and triethylamine (7 ml) were added to a dioxane solution (21 ml) that contained compound 6 (286 mg, 0.866 mmol), and the obtained mixture was then heated at 90° C. for 6 hours. Thereafter, the reaction solvent was distilled away under reduced pressure, and the residue was then subjected to silica gel column chromatography using ethyl acetate/hexane (1/4) as an elution solvent, so as to obtain a product of interest, 6-(tributylstannyl)-4'-methylaminoflavone (compound 8). Yield: 174 mg (yield constant: 37.2%) $^1$H NMR (300 MHz, CDCl$_3$) δ8.30 (s, 1H), 7.65-7.78 (m, 3H), 7.46 (d, J=9.0 Hz, 1H), 4.14 (s, 1H), 2.92 (s, 3H), 0.86-1.35 (m, 27H). MS m/z 541 (MH$^+$).

Synthesis of 6-(tributylstannyl)-4'-dimethylaminoflavone

Bis(tributyltin) (0.5 ml), tetrakistriphenylphosphine palladium (45 mg), and triethylamine (6 ml) were added to a dioxane solution (20 ml) that contained compound 7 (200 mg, 0.58 mmol), and the obtained mixture was then heated at 90° C. for 6 hours. Thereafter, the reaction solvent was distilled away under reduced pressure, and the residue was then subjected to silica gel column chromatography using ethyl acetate/hexane (1/2) as an elution solvent, so as to obtain a product of interest, 6-(tributylstannyl)-4'-dimethylaminoflavone (compound 9). Yield: 54 mg (yield constant: 16.8%) $^1$H NMR (300 MHz, CDCl$_3$) δ8.30 (s, 1H), 7.82 (d, J=9.0 Hz, 2H), 7.71-7.75 (m, 1H), 7.49 (d, J=9.0 Hz, 1H), 6.72-6.77 (m, 3H), 0.86-1.56 (m, 27H). MS m/z 555 (MH$^+$).

Synthesis of 6-iodo-4'-methylaminoflavone

A chloroform solution of iodine (1.5 ml, 1 M) was added to a chloroform solution (20 ml) that contained compound 8 (100 mg, 0.185 mmol) at room temperature. The obtained mixture was reacted at room temperature for 10 minutes, and a saturated sodium bisulfite aqueous solution (15 ml) was then added thereto, so as to terminate the reaction. The chloroform layer was separated, and it was then dried over sodium sulfate. Thereafter, the solvent was distilled away under reduced pressure, and the residue was then subjected to silica gel column chromatography using ethyl acetate/hexane (1/2) as an elution solvent, so as to obtain a product of interest, 6-iodo-4'-methylaminoflavone (compound 10). Yield: 20 mg (yield constant: 28.7%) $^1$H NMR (300 MHz, CDCl$_3$) δ8.53 (s, 1H), 7.90 (d, J=9.0 Hz, 1H), 7.75 (d, J=8.4 Hz, 2H), 7.28 (d, J=10.8 Hz, 1H), 6.64-6.69 (m, 3H), 4.15 (s, 1H), 2.93 (s, 3H). MS m/z 377 (M$^+$).

Synthesis of 6-iodo-4'-dimethylaminoflavone

A chloroform solution of iodine (1 ml, 1 M) was added to a chloroform solution (5 ml) that contained compound 9 (30 mg, 0.054 mmol) at room temperature. The obtained mixture was reacted at room temperature for 30 minutes, and a saturated sodium bisulfite aqueous solution (5 ml) was then added thereto, so as to terminate the reaction. The chloroform layer was separated, and it was then dried over sodium sulfate. Thereafter, the solvent was distilled away under reduced pressure, and the residue was then subjected to silica gel column chromatography using ethyl acetate/hexane (1/9) as an elution solvent, so as to obtain a product of interest, 6-iodo-4'-dimethylaminoflavone (compound 11). Yield: 10 mg (yield constant: 47.3%) $^1$H NMR (300 MHz, CDCl$_3$) δ8.54 (s, 1H), 7.92 (d, J=9.0 Hz, 1H), 7.81 (d, J=9.0 Hz, 2H), 7.29 (d, J=9.0 Hz, 1H), 6.71-6.80 (m, 3H), 3.09 (s, 6H). MS m/z 392 (MH$^+$).

Synthesis of 4-methoxybenzoic acid 2-acetyl-4-bromophenyl ester

5'-bromo-2'-hydroxyacetophenone (compound 12) (1.80 g, 10.6 mmol) was added to a pyridine solution (40 ml) that contained 4-methoxybenzoyl chloride (2.01 g, 9.35 mmol) in an ice bath. The obtained mixture was reacted at room temperature for 30 minutes, and the reaction solution was then poured into 1 N hydrochloric acid under cooling on ice. The obtained mixture was intensively stirred. The obtained precipitate was collected by filtration, and the filtrate was then washed with purified water, so as to obtain a product of interest, 4-methoxybenzoic acid 2-acetyl-4-bromophenyl ester (compound 13). Yield: 3.15 g (yield constant: 96.5%) $^1$H NMR (300 MHz, CDCl$_3$) δ 7.72 (d, J=7.5 Hz, 1H), 8.06 (d, J=7.2 Hz, 1H), 8.86 (s, 1H), 10.13 (s, 1H).

Synthesis of 1-(5-bromo-2-hydroxyphenyl)-3-(4-methoxyphenyl)propan-1,3-dione

Compound 13 (1.63 g, 4.67 mmol) was dissolved in pyridine (50 ml), and the obtained solution was heated up to 50° C. Thereafter, crushed potassium hydroxide (524 mg, 9.33 mmol) was added to the above solution, and the obtained mixture was then stirred for 15 minutes. Thereafter, the resultant was cooled on ice, and a 10% acetic acid solution was then added thereto. The obtained light yellow precipitate was collected by filtration, so as to obtain a product of interest, 1-(5-bromo-2-hydroxyphenyl)-3-(4-methoxyphenyl)propan-1,3-dione (compound 14). Yield: 1.42 g (yield constant: 85.2%) $^1$H NMR (300 MHz, CDCl$_3$) δ12.01 (s, 1H), 7.94 (d, J=9.3 Hz, 2H), 7.83 (s, 1H), 7.53 (d, J=9.0 Hz, 1H), 7.00 (d, J=9.3 Hz, 2H), 6.90 (d, J=8.7 Hz, 1H), 6.68 (s, 2H). 3.90 (s, 3H).

Synthesis of 6-bromo-4'-methoxyflavone

A mixed solution consisting of compound 14 (2.67 g, 7.65 mmol), concentrated sulfuric acid (0.78 ml), and acetic acid (40 ml) was heated to reflux for 1 hour. The temperature of the resultant was returned to room temperature, and ice pieces were then added to the reaction solution. The precipitated crystal was collected by filtration, so as to obtain a product of interest, 6-bromo-4'-methoxyflavone (compound 15). Yield: 2.01 g (yield constant: 79.4%) $^1$H NMR (300 MHz, CDCl$_3$) δ8.35 (s, 1H), 7.87 (d, J=9.0 Hz, 2H), 7.77 (d, J=9.0 Hz, 1H), 7.45 (d, J=9.3 Hz, 1H), 7.03 (d, J=9.0 Hz, 2H), 6.75 (s, 1H), 3.90 (s, 3H).

Synthesis of 6-bromo-4'-hydroxyflavone

A dichloromethane solution (12 ml) that contained boron tribromide was slowly added to a dichloromethane solution (215 ml) that contained compound 15 (400 mg, 1.21 mmol) while stirring under cooling on ice, and the obtained mixture was then reacted. After completion of the reaction, purified water (100 ml) was added to the reaction solution, and the dichloromethane layer was extracted. The extract was dried over anhydrous sodium sulfate, and the solvent was then distilled away under reduced pressure. The residue was subjected to silica gel column chromatography using ethyl acetate/hexane (2/5) as an elution solvent, so as to obtain a product of interest, 6-bromo-4'-hydroxyflavone (compound 16). Yield: 50 mg (yield constant: 13.1%) $^1$H NMR (300 MHz, CDCl$_3$) δ10.38 (s, 1H), 8.09 (s, 1H), 7.97-8.00 (m, 3H), 7.76 (d, J=9.0 Hz, 1H), 6.93-6.96 (m, 3H).

Synthesis of 6-(tributyl stannyl)-4'-methoxyflavone

Bis(tributyltin) (0.95 ml), tetrakistriphenylphosphine palladium (72 mg, 0.0623 mmol), and triethylamine (12 ml) were added to a dioxane solution (36 ml) that contained compound 15 (500 mg, 1.51 mmol), and the obtained mixture was then heated at 90° C. for 10 hours. Thereafter, the reaction solvent was distilled away under reduced pressure, and the residue was then subjected to silica gel column chromatography using ethyl acetate/hexane (1/10) as an elution solvent, so as to obtain a product of interest, 6-(tributyl)-4'-methoxyflavone (compound 17). Yield: 562 mg (yield constant: 68.8%) $^1$H NMR (300 MHz, CDCl$_3$) δ8.31 (s, 1H), 7.88-7.92 (m, 2H), 7.68-7.75 (m, 1H), 7.56 (s, 1H), 7.02-7.05 (m, 2H), 6.77 (s, 1H), 3.90 (s, 3H), 0.86-1.57 (m, 27H). MS m/z 542 (MH$^+$).

Synthesis of 6-(tributylstannyl)-4'-hydroxyflavone

Bis(tributyltin) (0.1 ml), tetrakistriphenylphosphine palladium (7.5 mg), and triethylamine (1.5 ml) were added to a dioxane solution (4.5 ml) that contained compound 16 (50 mg, 0.158 mmol), and the obtained mixture was then heated at 90° C. for 17 hours. Thereafter, the reaction solvent was distilled away under reduced pressure, and the residue was then subjected to silica gel column chromatography using ethyl acetate/hexane (1/5) as an elution solvent, so as to obtain a product of interest, 6-(tributylstannyl)-4'-hydroxyflavone (compound 18). Yield: 36 mg (yield constant: 43.3%) $^1$H NMR (300 MHz, CDCl$_3$) δ8.31 (s, 1H), 7.85 (d, J=8.4 Hz, 2H), 7.50-7.55 (m, 1H), 7.00 (d, J=8.4 Hz, 2H), 6.77 (s, 1H), 6.31 (s, 1H), 0.86-1.59 (m, 27H). MS m/z 527 (M$^+$).

Synthesis of 6-iodo-4'-methoxyflavone

A chloroform solution of iodine (5 ml, 1 M) was added to a chloroform solution (87 ml) that contained compound 17 (450 mg, 0.831 mmol) at room temperature. The obtained mixture was reacted at room temperature for 30 minutes, and a saturated sodium bisulfite aqueous solution (30 ml) was then added thereto, so as to terminate the reaction. The chloroform layer was separated, and it was then dried over sodium sulfate. Thereafter, the solvent was distilled away under reduced pressure, and the residue was then subjected to silica gel column chromatography using ethyl acetate/hexane (1/7) as an elution solvent, so as to obtain a product of interest, 6-iodo-4'-methoxyflavone (compound 19). Yield: 227 mg (yield constant: 72.2%) $^1$H NMR (300 MHz, CDCl$_3$) δ8.55 (s, 1H), 7.86-7.93 (m, 3H), 7.32 (d, J=8.7 Hz, 1H), 7.03 (d, J=8.7 Hz, 2H), 6.75 (s, 1H), 3.90 (s, 3H). MS m/z 378 (M$^+$).

Synthesis of 6-bromo-4'-hydroxyflavone

A dichloromethane solution (4.9 ml) that contained boron tribromide was slowly added to a dichloromethane solution (85 ml) that contained compound 19 (185 mg, 0.489 mmol) while stirring under cooling on ice, and the reaction was then carried out for 30 hours. After completion of the reaction, purified water (80 ml) was added to the reaction solution, and the dichloromethane layer was extracted. The extract was dried over anhydrous sodium sulfate, and the solvent was then distilled away under reduced pressure. The residue was subjected to silica gel column chromatography using ethyl acetate/hexane (1/4) as an elution solvent, so as to obtain a product of interest, 6-bromo-4'-hydroxyflavone (compound 20). Yield: 79 mg (yield constant: 44.3%) $^1$H NMR (300 MHz, DMSO$_6$) 610.37 (s, 1H), 8.27 (s, 1H), 8.28-8.30 (m, 1H), 7.98 (d, J=8.4 Hz, 2H), 7.61 (d, J=8.7 Hz, 1H), 6.93-6.95 (m, 3H). MS m/z 364 (M$^+$).

Synthesis of 4-nitrobenzoic acid 2-acetyl-4-methoxyphenyl ester

5'-methoxy-2'-hydroxyacetophenone (1.5 g, 9.03 mmol) was added to a pyridine solution (20 ml) that contained 4-nitrobenzoyl chloride (1.72 g, 9.26 mmol) in an ice bath. The obtained mixture was reacted at room temperature for 30 minutes, and the reaction solution was then poured into 1 N hydrochloric acid under cooling on ice. The obtained mixture was intensively stirred. The obtained precipitate was collected by filtration, and the filtrate was then washed with purified water, so as to obtain a product of interest, 4-nitrobenzoic acid 2-acetyl-4-methoxyphenyl ester (compound 21). Yield: 2.49 g (yield constant: 87.4%)

Synthesis of 1-(5-methoxy-2-hydroxyphenyl)-3-(4-nitrophenyl)propan-1,3-dione

Compound 21 (3.01 g, 9.55 mmol) was dissolved in pyridine (50 ml), and the obtained solution was heated up to 50° C. Thereafter, crushed potassium hydroxide (2.53 g, 45.1 mmol) was added to the above solution, and the obtained mixture was then stirred for 15 minutes. Thereafter, the resultant was cooled on ice, and a 10% acetic acid solution was then added thereto. The obtained light yellow precipitate was collected by filtration, so as to obtain a product of interest, 1-(5-methoxy-2-hydroxyphenyl)-3-(4-nitrophenyl)propan-1,3-dione (compound 22). Yield: 2.93 g (yield constant: 97.4%)

Synthesis of 6-methoxy-4'-nitroflavone

A mixed solution consisting of compound 22 (2.92 g, 9.26 mmol), concentrated sulfuric acid (1 ml), and acetic acid (50 ml) was heated to reflux for 1 hour. The temperature of the resultant was returned to room temperature, and ice pieces were then added to the reaction solution. The precipitated crystal was collected by filtration, so as to obtain a product of interest, 6-methoxy-4'-nitroflavone (compound 23). Yield: 2.31 g (yield constant: 84.1%)

Synthesis of 6-methoxy-4'-aminoflavone

Tin(II) chloride (3.32 g, 17.5 mmol) was slowly added to an ethanol solution (30 ml) that contained compound 23 (520 mg, 1.75 mmol), while stirring. The obtained mixture was heated to reflux for 1 hour. After completion of the reaction, a 1 N sodium hydroxide aqueous solution (150 ml) was added to the reaction solution, and the obtained mixture was then extracted with 50 ml of ethyl acetate (150 ml). The extract was dried over anhydrous sodium sulfate, and the solvent was then distilled away under reduced pressure, so as to obtain a product of interest, 6-methoxy-4'-aminoflavone (compound 24) in the form of a yellow crystal. Yield: 360 mg (yield constant: 74.8%) $^1$H NMR (300 MHz, DMSO-$d_6$) $\delta$7.91 (d, J=8.7 Hz, 2H), 7.69-7.70 (m, 1H), 7.38-7.42 (m, 2H), 6.93 (d, J=9.0 Hz, 2H), 6.82 (s, 1H), 3.86 (s, 2H).

Synthesis of 6-methoxy-4'-dimethylaminoflavone

Sodium cyanoborohydride (891 mg, 14.1 mmol) was slowly added to an acetic acid solution (30 ml) that contained compound 24 (630 mg, 2.36 mmol) and paraformaldehyde (707 mg, 23.6 mmol), while stirring. The obtained mixture was stirred at room temperature for 3 hours. After completion of the reaction, 50 ml of a 1 N sodium hydroxide aqueous solution was added to the reaction solution, and the obtained mixture was then extracted with 50 ml (25 ml×2) of chloroform. The extract was dried over anhydrous sodium sulfate, and the solvent was then distilled away under reduced pressure, so as to obtain a product of interest, 6-methoxy-4'-dimethylaminoflavone (compound 25) in the form of a yellow crystal. Yield: 450 mg (yield constant: 64.6%) $^1$H NMR (300 MHz, CDCl$_3$) $\delta$8.31 (s, 1H), 7.69-7.75 (m, 3H), 7.39 (d, J=8.7 Hz, 1H), 6.62-6.66 (m, 3H), 4.18 (s, 1H). 2.91 (s, 3H).

Synthesis of 6-methoxy-4'-methylaminoflavone

A sodium methylate-methanol solution (0.27 ml) was slowly added dropwise to a methanol solution (15 ml) that contained compound 24 (270 mg, 1.01 mmol) and paraformaldehyde (152 mg, 5.05 mmol), while stirring. The obtained mixture was heated to reflux for 1 hour. Thereafter, sodium borohydride (306 mg, 8.08 mmol) that was in the form of a solid was added to the reaction solution by slow degrees, and the obtained mixture was further heated to reflux for 2 hours. Thereafter, the reaction solvent was distilled away under reduced pressure, and the residue was then subjected to silica gel column chromatography using ethyl acetate/hexane (1/1) as an elution solvent, so as to obtain a product of interest, 6-bromo-4'-methylaminoflavone (compound 26). Yield: 120 mg (yield constant: 42.2%) $^1$H NMR (300 MHz, CDCl$_3$) $\delta$7.78 (d, J=8.7 Hz, 2H), 7.59 (m, 1H), 7.47 (d, J=9.0 Hz, 1H), 7.22-7.26 (m, 1H), 6.65-6.69 (m, 3H), 3.91 (s, 3H), 2.93 (s, 3H).

Synthesis of 6-hydroxy-4'-dimethylaminoflavone

A dichloromethane solution (5 ml) that contained boron tribromide was slowly added to a dichloromethane solution (50 ml) that contained compound 25 (200 mg, 0.68 mmol) while stirring under cooling on ice, and the obtained mixture was then reacted. After completion of the reaction, purified water (100 ml) was added to the reaction solution, and the dichloromethane layer was extracted. The extract was dried over anhydrous sodium sulfate, and the solvent was then distilled away under reduced pressure. The residue was subjected to silica gel column chromatography using chloroform/methanol (20/1) as an elution solvent, so as to obtain a product of interest, 6-hydroxy-4'-dimethylaminoflavone (compound 27). Yield: 25 mg (yield constant: 13.1%) $^1$H NMR (300 MHz, DMSO-$d_6$) $\delta$ 9.94 (s, 1H), 7.90 (d, J=9.0 Hz, 2H), 7.30 (m, 1H), 7.19-7.22 (m, 1H), 6.82 (d, J=9.0 Hz, 2H), 6.73 (s, 1H), 3.03 (s, 6H).

Synthesis of 6-hydroxy-4'-methylaminoflavone

A dichloromethane solution (5 ml) that contained boron tribromide was slowly added to a dichloromethane solution (20 ml) that contained compound 26 (270 mg, 0.96 mmol) while stirring under cooling on ice, and the obtained mixture was then reacted. After completion of the reaction, purified water (100 ml) was added to the reaction solution, and the dichloromethane layer was extracted. The extract was dried over anhydrous sodium sulfate, and the solvent was then distilled away under reduced pressure. The residue was subjected to silica gel column chromatography using chloroform/methanol (20/1) as an elution solvent, so as to obtain a product of interest, 6-hydroxy-4'-methylaminoflavone (compound 28). Yield: 15 mg (yield constant: 5.8%) $^1$H NMR (300 MHz, DMSO-$d_6$) $\delta$9.92 (s, 1H), 7.83 (d, J=9.0 Hz, 2H), 7.58 (d, J=8.7 Hz, 1H), 7.30 (m, 1H), 7.18-7.22 (m, 1H), 6.64-6.67 (m, 3H), 2.76 (s, 3H).

(2) Synthesis of Chalcone Derivative

Synthesis of (E)-1-(3-bromophenyl)-3-(4-hydroxy-3-methoxyphenyl)propan-2-en-1-one 1.99 g (10 mmol) of 3-bromoacetophenone was dissolved in ethanol (10 ml), and a 10% potassium hydroxide aqueous solution (30 ml) was then added thereto under cooling on ice. The obtained mixture was stirred for 15 minutes, and 1.52 g (10 mmol) of o-vanillin that was in the form of a solid was added thereto. The obtained mixture was further stirred for 15 minutes under cooling on ice. Thereafter, the temperature of the reaction solution was returned to room temperature, and it was then stirred for 4 hours. The precipitated crystal was subjected to suction filtration, and the filtrate was then distilled away under reduced pressure. The resultant was subjected to silica gel column chromatography using ethyl acetate/hexane (1/4) as an elution solvent, so as to obtain compound 29 as a product of interest. Yield: 470 mg (yield constant: 14.1%). $^1$H NMR (300 MHz, CDCl$_3$) $\delta$8.14 (s, 1H), 8.04 (d, J=15.9 Hz, 1H), 7.90-7.98 (m, 1H), 7.66-7.71 (m, 2H), 7.32-7.40 (m, 1H), 7.15-7.20 (m, 1H), 6.89-6.91 (m, 2H), 6.31 (s, 1H), 3.94 (s, 3H).

Synthesis of (E)-1-(3-(tributylstannyl)phenyl)-3-(4-hydroxy-3-mehtoxyphenyl)propan-2-en-1-one Bis(tributyltin) (1 ml), tetrakistriphenylphosphine palladium (75 mg), and triethylamine (5 ml) were added to a dioxane solution (10 ml) that contained compound 29 (370 mg, 1.11 mmol), and the obtained mixture was then heated to reflux for 12 hours. Thereafter, the reaction solvent was distilled away under reduced pressure, and the residue was then subjected to silica gel column chromatography using ethyl acetate/hexane (1/9) as an elution solvent, so as to obtain compound 30 as a product of interest. Yield: 161 mg (yield constant: 26.7%) $^1$H NMR (300 MHz, CDCl$_3$) $\delta$8.10 (s, 1H), 8.03 (d, J=15.9 Hz, 1H), 7.90-7.95 (m, 1H), 7.73 (d, J=15.9

Hz, 1H), 7.62-7.68 (m, 1H), 7.41-7.49 (m, 1H), 7.15-7.20 (m, 1H), 6.87-6.89 (m, 2H), 6.24 (s, 1H), 3.94 (s, 3H), 0.86-1.65 (m, 27H).

Synthesis of (E)-3-(4-hydroxy-3-methoxyphenyl)-1-(3-iodophenyl)propan-2-en-1-one A chloroform solution of iodine (2 ml, 1.1 M solution) was added to a chloroform solution (15 ml) that contained compound 30 (150 mg, 0.28 mmol) at room temperature. The obtained mixture was reacted at room temperature for 30 minutes, and a saturated sodium bisulfite aqueous solution (20 ml) was then added thereto, so as to terminate the reaction. The chloroform layer was separated, and it was then dried over sodium sulfate. Thereafter, the solvent was distilled away under reduced pressure, and the residue was then subjected to silica gel column chromatography using ethyl acetate/hexane (1/5) as an elution solvent, so as to obtain compound 31 as a product of interest. Yield: 47 mg (yield constant: 44.8%)

Synthesis of (E)-1-(4-bromophenyl)-3-(4-nitrophenyl)propan-2-en-1-one 1.99 g (10 mmol) of 4-bromoacetophenone was dissolved in ethanol (10 ml), and a 10% potassium hydroxide aqueous solution (30 ml) was added to the solution under cooling on ice. The obtained mixture was stirred for 15 minutes, and 1.51 g (10 mmol) of 4-nitrobenzaldehyde that was in the form of a solid was then added thereto. The obtained mixture was further stirred for 15 minutes under cooling on ice. The temperature of the reaction solution was returned to room temperature, and it was then stirred for 4 hours. Thereafter, ethyl acetate (50 ml) was added to the resultant. The precipitated crystal was subjected to suction filtration, and the filtrate was then fully washed with ethyl acetate, so as to obtain compound 32 as a product of interest. Yield: 1.27 g (yield constant: 38.2%).

Synthesis of (E)-3-(4-aminophenyl)-1-(4-bromophenyl)propan-2-en-1-one

Tin(II) chloride (5.0 g, 26.4 mmol) was slowly added to an ethanol solution (15 ml) that contained compound 32 (1.0 g, 3.01 mmol), while stirring. The obtained mixture was heated to reflux for 2 hours. After completion of the reaction, a 1 N sodium hydroxide aqueous solution (150 ml) was added to the reaction solution, and the obtained mixture was then extracted with 50 ml (150 ml) of ethyl acetate. The extract was dried over anhydrous sodium sulfate, and the solvent was then distilled away under reduced pressure. The residue was subjected to silica gel column chromatography using ethyl acetate/hexane (1/3) as an elution solvent, so as to obtain compound 33 as a product of interest. Yield: 556 mg (yield constant: 61.1%)

Synthesis of (E)-1-(4-bromophenyl)-3-(4-(dimethylamino)phenyl)propan-2-en-1-one Sodium cyanoborohydride (250 mg, 3.98 mmol) was slowly added to an acetic acid solution (15 ml) that contained compound 33 (250 mg, 0.83 mmol) and paraformaldehyde (400 mg, 13.4 mmol), while stirring. The obtained mixture was stirred at room temperature for 3 hours. After completion of the reaction, 50 ml of a 1 N sodium hydroxide aqueous solution was added to the reaction solution, and the obtained mixture was then extracted with 50 ml (25 ml×2) of chloroform. The extract was dried over anhydrous sodium sulfate, and the solvent was then distilled away under reduced pressure. The residue was subjected to silica gel column chromatography using ethyl acetate/hexane (1/12) as an elution solvent, so as to obtain compound 34 as a product of interest. Yield: 236 mg (yield constant: 86.1%)

Synthesis of (E)-1-(4-(tributylstannyl)phenyl)-3-(4-(dimethylamino)phenyl)propan-2-en-1-one Bis(tributyltin) (1 ml), tetrakistriphenylphosphine palladium (84 mg), and triethylamine (5, ml) were added to a dioxane solution (10 ml) that contained compound 34 (220 mg, 0.67 mmol), and the obtained mixture was then heated to reflux for 2 hours. Thereafter, the reaction solvent was distilled away under reduced pressure, and the residue was then subjected to silica gel column chromatography using ethyl acetate/hexane (1/18) as an elution solvent, so as to obtain compound 35 as a product of interest. Yield: 43 mg (yield constant: 11.9%) $^1$H NMR (300 MHz, CDCl$_3$) δ7.91 (d, J=9.0 Hz, 2H), 7.80 (d, J=15.9 Hz, 1H), 7.51-7.65 (m, 3H), 7.35 (d, J=15.9 Hz, 1H), 6.69 (d, J=9.0 Hz, 2H), 3.05 (s, 6H), 0.88-1.59 (m, 27H).

Synthesis of (E)-3-(4-(dimethylamino)phenyl)-1-(4-iodophenyl)propan-2-en-1-one A chloroform solution of iodine (2 ml, 1.1 mM solution) was added to a chloroform solution (5 ml) that contained compound 35 (4 mg, 0.07 mmol) at room temperature. The obtained mixture was reacted at room temperature for 30 minutes, and a saturated sodium bisulfite aqueous solution (20 ml) was then added thereto, so as to terminate the reaction. The chloroform layer was separated, and it was then dried over sodium sulfate. Thereafter, the solvent was distilled away under reduced pressure, and the residue was then subjected to silica gel column chromatography using ethyl acetate/hexane (1/9) as an elution solvent, so as to obtain compound 36 as a product of interest. Yield: 13 mg (yield constant: 46.6%) $^1$H NMR (300 MHz, CDCl$_3$) δ7.82-7.88 (m, 3H), 7.71-7.78 (m, 2H), 7.53 (d, J=9.0 Hz, 2H), 7.20-7.30 (m, 2H), 6.68 (d, J=9.0 Hz, 2H), 3.05 (s, 6H).

(3) Synthesis of Styrylchromone Derivative

Synthesis of (E)-2-acetyl-4-bromophenyl 3-(4-nitrophenyl)acrylate 5-bromo-2-hydroxyacetophenone (500 mg, 2.58 mmol) was added to a pyridine solution (10 ml) that contained 4-nitrocinnamate chloride (545 mg, 2.58 mmol). The obtained mixture was reacted at room temperature for 60 minutes, and the reaction solution was then poured into 1 N hydrochloric acid under cooling on ice. The obtained mixture was intensively stirred. The obtained precipitate was collected by filtration, and the filtrate was then washed with purified water, so as to obtain compound 37 as a product of interest. Yield: 1.073 g (yield constant: 99.2%) $^1$H NMR (300 MHz, CDCl$_3$) δ 8.29 (d, J=9.0 Hz, 1H), 7.95 (d, J=2.4 Hz, 1H), 7.77-7.62 (m, 4H), 7.10 (d, J=8.4 Hz, 2H), 6.80 (d, J=16.2 Hz, 1H).

Synthesis of 1-(5-bromo-2-hydroxyphenyl)-5-(4-nitrophenyl)pento-4-en-1,3-dione Compound 37 (500 mg, 1.28 mmol) was dissolved in pyridine (12 ml), and the obtained solution was heated up to 50° C. Thereafter, crushed potassium hydroxide (0.22 g, 3.84 mmol) was added to the above solution, and the obtained mixture was then stirred for 30 minutes. Thereafter, the resultant was cooled on ice, and a 10% acetic acid solution was then added thereto. The obtained light yellow precipitate was collected by filtration, so as to obtain compound 38 as a product of interest. Yield: 410 mg (yield constant: 82.0%)

Synthesis of 6-bromo-4'-nitrostyrylchromone

A mixed solution consisting of compound 38 (860 mg, 2.20 mmol), concentrated sulfuric acid (1.2 ml), and acetic acid (15 ml) was heated to reflux for 1 hour. The temperature of the reaction solution was returned to room temperature, and ice pieces were then added thereto. The precipitated crystal was collected by filtration, so as to obtain compound 39 as a product of interest. Yield: 790 mg (yield constant: 94.0%)

Synthesis of 6-bromo-4'-aminostyrylchromone

Tin(II) chloride (1.287 g, 4.74 mmol) was slowly added to an ethanol solution (30 ml) that contained compound 39 (361 mg, 0.97 mmol), while stirring. The obtained mixture was heated to reflux for 2 hours. After completion of the reaction, a 1 N sodium hydroxide aqueous solution (100 ml) was added to the reaction solution, and the obtained mixture was then extracted with 100 ml of ethyl acetate. The extract was dried over anhydrous sodium sulfate, and the solvent was then distilled away under reduced pressure, so as to obtain compound 40 as a product of interest. Yield: 210 mg (yield constant: 63.3%) $^1$H NMR (300 MHz, CDCl$_3$) δ 8.30 (d, J=2.4 Hz), 7.71 (dd, 1H), 7.47-7.38 (m, 4H), 6.68 (d, J=8.4 Hz, 2H), 6.55 (d, J=15.9 Hz, 1H), 6.25 (s, 1H), 3.99 (s, 2H).

Synthesis of 6-bromo-4'-methylaminostyrylchromone

A sodium methylate-methanol solution (0.45 ml) was slowly added dropwise to a methanol solution (15 ml) that contained compound 40 (710 mg, 2.07 mmol) and paraformaldehyde (231 mg, 7.70 mmol), while stirring. The obtained mixture was heated to reflux for 1 hour. Thereafter, sodium borohydride (270 mg, 7.13 mmol) that was in the form of a solid was added to the reaction solution by slow degrees, and the obtained mixture was further heated to reflux for 2 hours. Thereafter, the reaction solvent was distilled away under reduced pressure, and the residue was then subjected to silica gel column chromatography using chloroform as an elution solvent, so as to obtain compound 41 as a product of interest. Yield: 690 mg (yield constant: 96%) $^1$H-NMR (300 MHz, CDCl$_3$) δ 8.30 (d, J=2.4 Hz, 1H), 7.71 (dd, 1H), 7.45-7.29 (m, 4H), 6.61-6.56 (m, 3H), 6.25 (s, 1H), 4.18 (s, 1H), 2.89 (s, 3H). MS m/z 355.

Synthesis of 6-bromo-4'-dimethylaminostyrylchromone

Sodium cyanoborohydride (214 mg, 3.40 mmol) was slowly added to an acetic acid solution (10 ml) that contained compound 40 (194 mg, 0.567 mmol) and paraformaldehyde (170 mg, 5.67 mmol), while stirring. The obtained mixture was stirred at room temperature for 3 hours. After completion of the reaction, 50 ml of a 1 N sodium hydroxide aqueous solution was added to the reaction solution, and the obtained mixture was then extracted with 50 ml of chloroform. The extract was dried over anhydrous sodium sulfate, and the solvent was then distilled away under reduced pressure, so as to obtain compound 42. Yield: 0.15 g (yield constant: 71.5%)

$^1$H NMR (300 MHz, CDCl$_3$) δ 8.31 (d, J=2.4 Hz, 1H), 7.71 (dd, 1H), 7.56-7.46 (m, 3H), 7.39 (d, J=8.7 Hz, 1H), 6.72 (d, J=2.7 Hz, 2H), 6.57 (d, J=15.9 Hz, 1H), 6.24 (s, 1H), 3.04 (s, 6H). MS m/z 371.

Synthesis of 6-(tributylstannyl)-4'-aminostyrylchromone

Bis(tributyltin) (0.5 ml), tetrakistriphenylphosphine palladium (40 mg, 0.034 mmol), and triethylamine (8 ml) were added to a dioxane solution (12 ml) that contained compound 40 (242 mg, 0.707 mmol), and the obtained mixture was then heated at 90° C. for 6 hours. Thereafter, the reaction solvent was distilled away under reduced pressure, and the residue was then subjected to silica gel column chromatography using ethyl acetate/hexane (2/3) as an elution solvent, so as to obtain compound 43 as a product of interest. Yield: 220 mg (yield constant: 56.3%) $^1$H NMR (300 MHz, CDCl$_3$) δ8.28 (s, 1H), 7.74 (d, J=8.1 Hz, 1H), 7.54-7.48 (m, 3H), 7.42 (d, J=9.0 Hz, 1H), 6.68 (d, J=8.4 Hz, 2H), 6.57 (d, J=15.9 Hz, 1H), 6.27 (s, 1H), 4.07 (s, 2H), 0.86-1.54 (m, 27H). MS m/z 496.

Synthesis of 6-(tributylstannyl)-4'-methylaminostyrylchromone

Bis(tributyltin) (0.6 ml), tetrakistriphenylphosphine palladium (41 mg, 0.035 mmol), and triethylamine (7 ml) were added to a dioxane solution (10 ml) that contained compound 41 (300 mg, 0.84 mmol), and the obtained mixture was then heated at 90° C. for 6 hours. Thereafter, the reaction solvent was distilled away under reduced pressure, and the residue was then subjected to silica gel column chromatography using ethyl acetate/hexane (1/4) as an elution solvent, so as to obtain compound 44 as a product of interest. Yield: 204 mg (yield constant: 42.8%) $^1$HNMR (300 MHz, CDCl$_3$) δ8.28 (s, 1H), 7.74 (d, 1H), 7.54-7.43 (m, 4H), 6.62-6.57 (m, 3H), 6.26 (s, 1H), 4.11 (s, 1H), 2.89 (s, 3H), 0.86-1.52 (m, 27H). MS m/z 567.

Synthesis of 6-(tributylstannyl)-4'-dimethylaminostyrylchromone

Bis(tributyltin) (0.3 ml), tetrakistriphenylphosphine palladium (20 mg, 0.017 mmol), and triethylamine (5 ml) were added to a dioxane solution (10 ml) that contained compound 42 (150 mg, 0.405 mmol), and the obtained mixture was then heated at 90° C. for 6 hours. Thereafter, the reaction solvent was distilled away under reduced pressure, and the residue was then subjected to silica gel column chromatography using ethyl acetate/hexane (1/4) as an elution solvent, so as to obtain compound 45 as a product of interest. Yield: 220 mg (yield constant: 37.4%) $^1$H NMR (300 MHz, CDCl$_3$) δ8.23 (s, 1H), 7.74 (dd, 1H), 7.59-7.47 (m, 3H), 7.42 (d, 1H), 6.71 (d, J=8.9 Hz, 2H), 6.56 (d, J=15.8 Hz, 1H), 6.27 (s, 1H), 3.04 (s, 6H), 0.86-1.74 (m, 27H). MS m/z 580.

Synthesis of 6-iodo-4'-aminostyrylchromone

Compound 43 (220 mg, 0.398 mmol) was dissolved in 5 ml of chloroform, and a chloroform solution of iodine (3 ml, 0.25 M) was added to the solution at room temperature, while stirring. The obtained mixture was reacted at room temperature for 10 minutes, and a saturated sodium bisulfite aqueous solution (15 ml) was then added thereto, so as to terminate the reaction. The chloroform layer was separated, and it was then dried over sodium sulfate. Thereafter, the solvent was distilled away under reduced pressure, and the residue was then subjected to silica gel column chromatography using ethyl acetate/hexane (1/2) as an elution solvent, so as to obtain compound 46 as a product of interest. Yield: 60 mg (yield constant: 38.8%) $^1$H NMR (300 MHz, CDCl$_3$) δ8.50 (d, J=9.0 Hz, 1H), 7.89 (dd, 1H), 7.53-7.39 (m, 3H), 7.27 (d, J=8.7 Hz, 1H), 6.69 (d, J=8.4 Hz, 2H), 6.56 (d, J=15.9 Hz, 1H), 3.99 (s, 2H). MS m/z 389.

Synthesis of 6-iodo-4'-methylaminostyrylchromone

Compound 44 (200 mg, 0.353 mmol) was dissolved in 7 ml of chloroform, and a chloroform solution of iodine (4 ml, 0.25 M) was added to the solution at room temperature, while stirring. The obtained mixture was reacted at room temperature for 10 minutes, and a saturated sodium bisulfite aqueous solution (15 ml) was then added thereto, so as to terminate the reaction. The chloroform layer was separated, and it was then dried over sodium sulfate. Thereafter, the solvent was distilled away under reduced pressure, and the residue was then subjected to silica gel column chromatography using ethyl acetate/hexane (1/3) as an elution solvent, so as to obtain compound 47 as a product of interest. Yield: 32 mg (yield constant: 22.4%) $^1$H NMR (300 MHz, CDCl$_3$) δ8.50 (d, J=2.1 Hz, 1H), 7.94 (dd, 1H), 7.59-7.42 (m, 3H), 7.28 (d, J=8.2 Hz, 1H), 6.61 (d, J=8.7 Hz, 2H), 6.54 (d, J=15.6 Hz, 1H), 6.25 (s, 1H), 4.21 (s, 1H), 2.94 (s, 3H). MS m/z 403.

Synthesis of 6-iodo-4'-dimethylaminostyrylchromone

Compound 45 (35 mg, 0.06 mmol) was dissolved in 6 ml of chloroform, and a chloroform solution of iodine (4 ml, 0.15 M) was added to the solution at room temperature, while stirring. The obtained mixture was reacted at room temperature for 10 minutes, and a saturated sodium bisulfite aqueous solution (10 ml) was then added thereto, so as to terminate the reaction. The chloroform layer was separated, and it was then dried over sodium sulfate. Thereafter, the solvent was distilled away under reduced pressure, and the residue was then subjected to silica gel column chromatography using ethyl acetate/hexane (1/4) as an elution solvent, so as to obtain compound 48 as a product of interest. Yield: 18 mg (yield constant: 71.8%) $^1$HNMR (300 MHz, CDCl$_3$) δ 8.45 (d, 1H), 7.94 (dd, 1H), 7.59-7.44 (m, 3H), 7.23 (d, 1H), 6.65 (d, J=8.7 Hz, 2H), 6.65 (d, 1H), 6.25 (s, 1H), 3.04 (s, 6H). MS m/z 417.

Synthesis of (E)-2-acetyl-4-methoxyphenyl 3-(4-nitrophenyl)acrylate 5-methoxy-2-hydroxyacetophenone (500 mg, 3.01 mmol) was added to a pyridine solution (10 ml) that contained 4-nitrocinnamate chloride (800 mg, 0.44 mmol). The obtained mixture was reacted at room temperature for 60 minutes, and the reaction solution was then poured into 1 N hydrochloric acid under cooling on ice. The obtained mixture was intensively stirred. The obtained precipitate was collected by filtration, and the filtrate was then washed with purified water, so as to obtain acetophenone 49 as a product of interest. $^1$H NMR (300 MHz, CDCl$_3$) δ8.28 (d, J=8.7 Hz, 1H), 7.93 (s, 1H), 7.88-7.76 (m, 4H), 7.30 (d, 2H), 6.79 (d, J=15.9 Hz, 1H), 3.87 (s, 3H), 2.56 (s, 3H).

Synthesis of 1-(5-methoxy-2-hydroxyphenyl)-5-(4-nitrophenyl)pento-4-en-1,3-dione Compound 49 (126 mg, 3.19 mmol) was dissolved in pyridine (20 ml), and the obtained solution was heated up to 50°

C. Thereafter, crushed potassium hydroxide (0.4 g, 1.11 mmol) was added to the above solution, and the obtained mixture was then stirred for 30 minutes. Thereafter, the resultant was cooled on ice, and a 10% acetic acid solution was then added thereto. The obtained light yellow precipitate was collected by filtration, so as to obtain compound 50 as a product of interest. Yield: 902 mg (yield constant: 72.0%) $^1$H NMR (300 MHz, CDCl$_3$) δ8.27 (d, J=9.0 Hz, 2H), 7.72-7.69 (m, 4H), 7.14-7.12 (m, 3H), 6.97 (s, 1H), 6.77 (d, 1H), 3.83 (s, 3H).

Synthesis of 6-methoxy-4-nitrostyrylchromone

A mixed solution consisting of compound 50 (900 mg, 2.64 mmol), concentrated sulfuric acid (1.0 ml), and acetic acid (30 ml) was heated to reflux for 1 hour. The temperature of the reaction solution was returned to room temperature, and ice pieces were then added thereto. The precipitated crystal was collected by filtration, so as to obtain compound 51 as a product of interest. Yield: 810 mg (yield constant: 90.0%)

Synthesis of 6-methoxy-4-aminostyrylchromone

Tin(II) chloride (2.5 g, 1.32 mmol) was slowly added to an ethanol solution (25 ml) that contained compound 51 (830 mg, 2.57 mmol), while stirring. The obtained mixture was heated to reflux for 2 hours. After completion of the reaction, a 1 N sodium hydroxide aqueous solution (50 ml) was added to the reaction solution, and the obtained mixture was then extracted with 50 ml of chloroform. The extract was dried over anhydrous sodium sulfate, and the solvent was then distilled away under reduced pressure, so as to obtain compound 52 as a product of interest. Yield: 510 mg (yield constant: 61.4%)

Synthesis of 6-methoxy-4-methylaminostyrylchromone

A sodium methylate-methanol solution (0.46 ml) was slowly added dropwise to a methanol solution (15 ml) that contained compound 52 (500 mg, 1.7 mmol) and paraformaldehyde (262 mg, 8.72 mmol), while stirring. The obtained mixture was heated to reflux for 1 hour. Thereafter, sodium borohydride (310 mg, 8.18 mmol) that was in the form of a solid was added to the reaction solution by slow degrees, and the obtained mixture was further heated to reflux for 2 hours. Thereafter, the reaction solvent was distilled away under reduced pressure, and the residue was then subjected to silica gel column chromatography using chloroform as an elution solvent, so as to obtain compound 53 as a product of interest. Yield: 179 mg (yield constant: 34.4%)

Synthesis of 6-methoxy-4-dimethylaminostyrylchromone

Sodium cyanoborohydride (314 mg, 5.02 mmol) was slowly added to an acetic acid solution (15 ml) that contained compound 52 (270 mg, 0.92 mmol) and paraformaldehyde (300 mg, 9.99 mmol), while stirring. The obtained mixture was stirred at room temperature for 3 hours. After completion of the reaction, 50 ml of a 1 N sodium hydroxide aqueous solution was added to the reaction solution, and the obtained mixture was then extracted with 50 ml of chloroform. The extract was dried over anhydrous sodium sulfate, and the solvent was then distilled away under reduced pressure, so as to obtain compound 54. Yield: 0.20 g (yield constant: 70.9%) $^1$H NMR (300 MHz, CDCl$_3$) δ7.56 (d, J=5.1 Hz, 1H), 7.54 (s, 1H), 7.48-7.42 (m, 3H), 7.25 (d, 1H), 6.74 (d, J=9.0 Hz, 2H), 6.54 (d, J=15.9 Hz, 1H), 6.24 (s, 1H), 3.89 (s, 3H), 3.02 (s, 6H).

Synthesis of 6-hydroxy-4-aminostyrylchromone

Compound 52 (270 mg, 0.92 mmol) was dissolved in 40 ml of dichloromethane, and 4.6 ml of a dichloromethane solution of boron tribromide was slowly added to the solution under cooling on ice. The obtained mixture was reacted on ice. Thereafter, the reaction solution was added in small portions to ice water, so as to separate the dichloromethane layer from the water layer, followed by extraction, thereby obtaining compound 55 as a product of interest. Yield: 112 mg (yield constant: 40.9%) $^1$H NMR (300 MHz, CDCl$_3$) δ9.29 (s, 1H), 7.55-7.42 (m, 3H), 7.39-7.28 (m, 3H), 6.78 (d, J=15.9 Hz, 1H), 6.68 (d, 1H), 6.24, (s, 1H), 5.91 (s, 2H).

Synthesis of 6-hydroxy-4-methylaminostyrylchromone

Compound 53 (179 mg, 0.58 mmol) was dissolved in 25 ml of dichloromethane, and 2.9 ml of a dichloromethane solution of boron tribromide was slowly added to the solution under cooling on ice. The obtained mixture was reacted on ice. Thereafter, the reaction solution was added in small portions to ice water, so as to separate the dichloromethane layer from the water layer, followed by extraction, thereby obtaining compound 56 as a product of interest. Yield: 12 mg (yield constant: 7.1%) $^1$H NMR (300 MHz, CDCl$_3$) δ9.92 (s, 1H), 7.55-7.49 (m, 3H), 7.28 (d, 2H), 7.19 (dd, 1H), 6.81 (d, J=15.9 Hz, 1H), 6.59 (d, J=8.7 Hz, 2H), 6.25 (s, 1H), 3.23 (s, 1H), 2.52 (s, 3H).

Synthesis of 6-hydroxy-4-dimethylaminostyrylchromone

Compound 54 (160 mg, 0.522 mmol) was dissolved in 25 ml of dichloromethane, and 2.9 ml of a dichloromethane solution of boron tribromide was slowly added to the solution under cooling on ice. The obtained mixture was reacted on ice. Thereafter, the reaction solution was added in small portions to ice water, so as to separate the dichloromethane layer from the water layer, followed by extraction, thereby obtaining compound 57 as a product of interest. Yield: 80 mg (yield constant: 52.4%) $^1$H NMR (300 MHz, CDCl$_3$) δ 7.56-7.52 (m, 3H), 7.27-7.22 (m, 3H), 6.87 (d, J=17.7 Hz, 1H), 6.75 (d, J=9.0 Hz, 2H), 6.26 (s, 1H), 2.99 (s, 6H).

(4) Synthesis of Coumarin Derivative

Synthesis of 6-bromo-3-(4-nitrophenyl)coumarin 5-bromosalicylaldehyde (300 mg, 1.5 mmol), p-nitrophenylacetic acid (280 mg, 1.6 mmol), and 2-chloro-1-methylpyridinium iodide (770 mg, 3.0 mmol) were dissolved in acetonitrile (15 ml). Triethylamine (0.5 ml) was added to the solution, and the obtained mixture was then heated to reflux for 3 hours. Thereafter, the reaction solvent was distilled away under reduced pressure, and diluted hydrochloric acid was added to the residue that was in a semisolid state, followed by suction filtration. The precipitate was collected by filtration, so as to obtain compound 58 as a product of interest. Yield: 300 mg (yield constant: 57.8%).

Synthesis of 6-bromo-3-(4-aminophenyl)coumarin

Compound 58 (150 mg, 0.43 mmol) was dissolved in ethanol (25 ml), and tin(II) chloride (380 mg, 2 mmol) was then added to the solution. The obtained mixture was heated to reflux for 2 hours. Thereafter, the reaction solvent was distilled away under reduced pressure, and a 0.1 N sodium hydroxide aqueous solution was added. The obtained mixture was extracted with ethyl acetate. The ethyl acetate phase was recovered, and ethyl acetate was then distilled away under reduced pressure, so as to obtain compound 59 as a product of interest. Yield: 100 mg (yield constant: 74%) $^1$H NMR (300 MHz, CDCl$_3$) δ 7.63 (m, 2H), 7.55 (m, 3H), 7.25 (d, J=7.2 Hz, 1H), 6.74 (d, J=8.7 Hz, 2H), 3.88 (s, 2H).

Synthesis of 6-bromo-3-(4-methylaminophenyl)coumarin

Compound 59 (150 mg, 0.47 mmol) was dissolved in methanol (4.4 ml). Paraformaldehyde (77 mg, 2.66 mmol) and a sodium methylate-methanol solution (0.15 ml) were added to the solution. The obtained mixture was then heated to reflux. 0.5 hours later, sodium borohydride (95 mg, 2.5 mmol) was added to the reaction solution by slow degrees, and the obtained mixture was further heated to reflux for 2 hours. Thereafter, the reaction solvent was distilled away under reduced pressure, and the residue was then subjected to silica gel column chromatography using ethyl acetate/hexane (1/2) as an elution solvent, so as to obtain compound 60 as a product of interest. Yield: 32 mg (yield constant: 21%) $^1$H NMR (300 MHz, CDCl$_3$) δ 7.62 (s, 1H), 7.59 (d, J=6.9 Hz, 2H), 7.52 (d, J=8.7 Hz, 2H), 7.24 (d, J=10.5 Hz, 1H), 6.65 (d, J=8.4 Hz, 2H), 3.91 (s, 1H), 2.88 (s, 3H).

Synthesis of 6-bromo-3-(4-dimethylaminophenyl)coumarin

Compound 60 (160 mg, 0.5 mmol) was dissolved in acetic acid (6.5 ml). Paraformaldehyde (157 mg, 5.4 mmol) was added to the solution, and the obtained mixture was then heated to reflux. 0.5 hours later, the reaction solution was cooled to ordinary temperature, and sodium cyanoborohydride (190 mg, 3.0 mmol) was added thereto. The obtained mixture was stirred at room temperature for 4 hours. Thereafter, the reaction solvent was distilled away under reduced pressure, and the residue was then subjected to silica gel column chromatography using chloroform as an elution solvent, so as to obtain compound 61 as a product of interest. Yield: 100 mg (yield constant: 58%) $^1$H NMR (300 MHz, CDCl$_3$) δ 7.66 (s, 1H), 7.62 (d, J=6.0 Hz, 2H), 7.23 (d, J=9.2 Hz, 1H), 6.76 (d, J=8.4 Hz, 2H), 3.01 (s, 3H).

Synthesis of 6-(tributylstannyl)-3-(4-aminophenyl)coumarin

Compound 59 (150 mg, 0.47 mmol) was dissolved in 1,4-dioxane (15 ml). Bis(tributyltin) (0.5 ml), tetrakistriphenylphosphine palladium (30 mg, 0.026 mmol), and triethylamine (7 ml) were added to the solution. The obtained mixture was then heated to reflux. Thereafter, the reaction solvent was distilled away under reduced pressure, and the residue was then subjected to silica gel column chromatography using ethyl acetate/hexane (1/1) as an elution solvent, so as to obtain compound 62 as a product of interest. Yield: 100 mg (yield constant: 40%) $^1$H NMR (300 MHz, CDCl$_3$) δ 7.73 (s, 1H), 7.57 (m, 4H), 7.32 (d, 1H), 6.7 (d, J=8.4 Hz, 2H), 3.84 (s, 2H), 1.64 (m, 6H), 1.34 (m, 6H), 1.12 (m, 6H), 0.92 (m, 9H).

Synthesis of 6-(tributylstannyl)-3-(4-methylaminophenyl)coumarin

Compound 60 (230 mg, 0.43 mmol) was dissolved in 1,4-dioxane (23 ml). Bis(tributyltin) (0.7 ml), tetrakistriphenylphosphine palladium (46 mg), and triethylamine (11 ml) were added to the solution. The obtained mixture was then heated to reflux. Thereafter, the reaction solvent was distilled away under reduced pressure, and the residue was then subjected to silica gel column chromatography using ethyl acetate/hexane (1/4) as an elution solvent, so as to obtain compound 63 as a product of interest. Yield: 50 mg (yield constant: 20%) $^1$H NMR (300 MHz, CDCl$_3$) δ 7.73 (s, 1H), 7.62 (d, J=8.7 Hz, 2H), 7.54 (d, J=8.1 Hz, 2H), 7.32 (d, J=8.7 Hz, 1H), 6.66 (d, J=8.7 Hz, 2H), 3.94 (s, 1H), 2.87 (s, 3H), 0.90-1.54 (m, 27H). MSm/z 541

Synthesis of 6-(tributylstannyl)-3-(4-dimethylaminophenyl)coumarin

Compound 61 (150 mg, 0.44 mmol) was dissolved in 1,4-dioxane (15 ml). Bis(tributyltin) (0.5 ml), tetrakistriphenylphosphine palladium (30 mg), and triethylamine (7 ml) were added to the solution, and the obtained mixture was then heated to reflux. 5 hours later, the reaction solvent was distilled away under reduced pressure, and the residue was then subjected to silica gel column chromatography using ethyl acetate/hexane (1/5) as an elution solvent, so as to obtain compound 64 as a product of interest. Yield: 63 mg (yield constant: 26%) $^1$H NMR (300 MHz, CDCl$_3$) δ 7.73 (s, 1H), 7.67 (d, J=8.7 Hz, 2H), 7.55 (d, 2H), 7.28 (d, 1H), 6.77 (d, J=9.0 Hz, 2H), 3.01 (s, 6H), 0.90-1.60 (m, 27H). MSm/z 555

Synthesis of 6-iodo-3-(4-aminophenyl)coumarin

Compound 62 (50 mg, 0.095 mmol) was dissolved in chloroform (5 ml), and a chloroform solution of iodine (3 ml, 1 M) was then added to the solution. The obtained mixture was reacted at room temperature for 10 minutes, and a saturated sodium bisulfite aqueous solution (10 ml) was then added thereto, so as to terminate the reaction. The chloroform phase was recovered, and chloroform was then distilled away under reduced pressure. Thereafter, the residue was subjected to silica gel column chromatography using ethyl acetate/hexane (1/1) as an elution solvent, so as to obtain compound 65 as a product of interest. Yield: 30 mg (yield constant: 87%)

Synthesis of 6-iodo-3-(4-methylaminophenyl)coumarin

Compound 63 (40 mg, 0.074 mmol) was dissolved in chloroform (5 ml), and a chloroform solution of iodine (3 ml, 1 M) was then added to the solution. The obtained mixture was reacted at room temperature for 10 minutes, and a saturated sodium bisulfite aqueous solution (10 ml) was then added thereto, so as to terminate the reaction. The chloroform phase was recovered, and chloroform was then distilled away under reduced pressure. Thereafter, the residue was subjected to silica gel column chromatography using ethyl acetate/hexane (1/2) as an elution solvent, so as to obtain compound 66 as a product of interest. Yield: 20 mg (yield constant: 72%). MSm/z 377

Synthesis of 6-iodo-3-(4-dimethylaminophenyl)coumarin

Compound 64 (30 mg, 0.054 mmol) was dissolved in chloroform (5 ml), and a chloroform solution of iodine (3 ml, 1 M) was then added to the solution. The obtained mixture was reacted at room temperature for 10 minutes, and a saturated sodium bisulfite aqueous solution (10 ml) was then added thereto, so as to terminate the reaction. The chloroform phase was recovered, and chloroform was then distilled away under reduced pressure. Thereafter, the residue was subjected to silica gel column chromatography using ethyl acetate/hexane (1/4) as an elution solvent, so as to obtain compound 67 as a product of interest. Yield: 20 mg (yield constant: 95%). MSm/z 391.

(5) Iodine Labeling Experiment

50 µl of an ethanol solution that contained a tributyl tin precursor (1 mg/ml), 50 µl of 1 N hydrochloric acid, and Na[251]I (1-5 µCi) were placed in a glass vial. Finally, 50 µl of a hydrogen peroxide solution (3% W/V) was added thereto. The obtained mixture was left at room temperature for 10 minutes. Thereafter, 100 µl of a saturated sodium bisulfite aqueous solution was added to the reaction solution, so as to terminate the reaction. The reaction solution was neutralized in a saturated sodium bicarbonate aqueous solution, and it was then extracted with ethyl acetate (1 ml×2). Thereafter, the extract was passed through a Pasteur pipette that contained sodium sulfate for dehydration, and ethyl acetate was then evaporated with nitrogen. Thereafter, the residue was dissolved in ethanol, followed by purification by reversed-phase HPLC (water:acetonitrile=40:60). Using a nonradioactive compound as an authentic sample, the absorbance at 254 nm was analyzed by HPLC. A product of interest corresponding thereto was fractionated, and acetonitrile was then distilled away. Radioactivity was measured, and the specific activity of the product of interest was then calculated based on the specific activity of $^{125}$I (2200 Ci/mmol).

(6) Experiment Regarding In Vitro Bond of Flavone Derivative Using Aβ(1-40) Aggregates and Aβ(1-42) Aggregates Aβ aggregates was dissolved in a buffer (pH 7.4) that contained 10 mM sodium phosphate and 1 mM EDTA, resulting in a concentration of 0.5 mg/ml. Thereafter, the obtained solution was incubated at 37° C. for 36 to 42 hours. A binding experiment was carried out using 12×75 mm borosilicate glass tubes. 900 µl of a 10% ethanol solution, 50 µl (57 nM) of Aβ(1-40) aggregates solution, and 50 µl of [$^{125}$I] compound 10, [$^{125}$I] compound 11, [$^{125}$I] compound 19, [$^{125}$I] compound 20, [$^{125}$I] compound 31, [$^{125}$I] compound 36, [$^{125}$I] compound 46, [$^{125}$I] compound 47 or [$^{125}$I] compound 48, each of which had various concentrations, were mixed. The obtained mixture was left at room temperature for 3 hours. Non-specific bond was calculated using nonradioactive compound 11 (1 µM). Flavone, chalcone, styrylchromone, and coumarin derivatives, which had bound to Aβ aggregates, were separated from those, which had not bound to Aβ aggregates, employing the Brandel M-24R cell harvester, using Whatman GF/B filters. The radioactivity of a substance remaining in the filter used in filtration was measured with a γ counter. With regard to [$^{125}$I] compound 11, the Kd value thereof was calculated by the Scatchard analysis. In addition, using [$^{125}$I] compound 11 as a radioactive ligand, an inhibition experiment was carried out by the following method using the Aβ(1-40) aggregates and the Aβ(1-42) aggregates. 850 µl of a 10% ethanol solution, 50 µl (57 nM) of Aβ(1-40) aggregates solution, 50 µl (57 nM) of Aβ(1-42) aggregates solution, and 50 µl of compound 10, compound 11, compound 19, or compound 20, each of which had various concentrations, were mixed. The obtained mixture was left at room temperature for 3 hours. Non-specific bond was calculated using nonradioactive compound 11 (1 µM). The 50% inhibitory concentration was calculated using GraphPad Prism (GraphPad Software), and the inhibition constant (Ki value) was calculated according to the formula of Cheng-Prusoff, Ki=IC50/(1+[L]/Kd). In this formula, [L] represents the concentration of [$^{125}$I] compound 11, and Kd represents the dissociation constant of [$^{125}$I] compound 11 to the Aβ(1-40) aggregates and the Aβ(1-42) aggregates.

(7) Experiment Regarding Radioactivity Distribution in Mouse Body

Radioiodine labeled forms (compounds 10, 11, 19, 20, 31, 46, 47, and 48) were diluted with a normal saline solution containing 5% to 10% ethanol. Thereafter, 100 μl (0.5 to 1 μCi) of each labeled form was intravenously administered to each group consisting of three to five 5-week-old ddY male mice (25 to 30 g). 2, 10, 30, and 60 minutes after the intravenous administration, such mice were decapitated, and blood was collected. Thereafter, organs were excised, and the weight and radioactivity thereof were then measured.

(8) Binding Experiment Using Brain Tissues of Patient with Alzheimer's Disease

Tissues at the temporal lobe site of the brain of a patient with Alzheimer's disease were fixed with formalin, and were then embedded in paraffin. A section with a thickness of 5 μm was prepared from the paraffin block, and the paraffin was then removed by an ordinary treatment with xylene and ethanol (Lippa, C. F., Nee, L. E., Mori, H & George-Hyslop, P. (1998) The Lancet 352:1117-1118). As the final stage, neutralization was carried out with a phosphate buffer. Thereafter, compounds 10, 11, 19, and 20 were reacted in a concentration of 100 nM at room temperature for 10 minutes. Thereafter, the reaction product was washed with a phosphate buffer three times, and then with 50% ethanol three time, so as to terminate the reaction. Thereafter, the resultant was dehydrated by treatments with alcohol and xylene, followed by embedding with Entellan(R) new. The bond of the above compound was confirmed by image observation with a CCD camera (M-3204C) included with a fluorescence microscope (Olympus BX50).

[Experimental Results]
(1) Synthesis of Compounds

Figure 2:
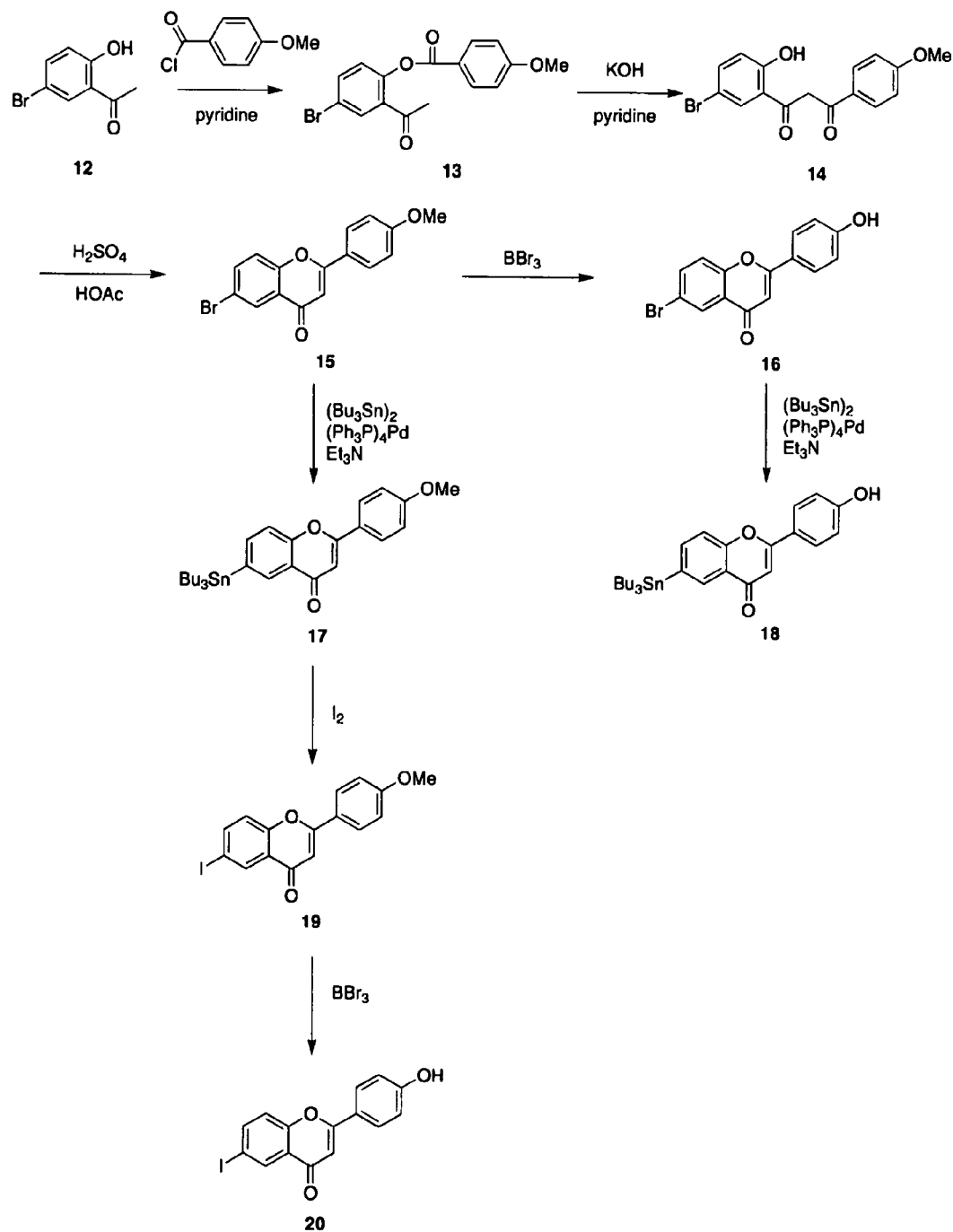
FIG. 2 is a view showing synthetic method (2) of a flavone derivative (the numbers as shown in the figure indicate compound numbers).
Figure 3:
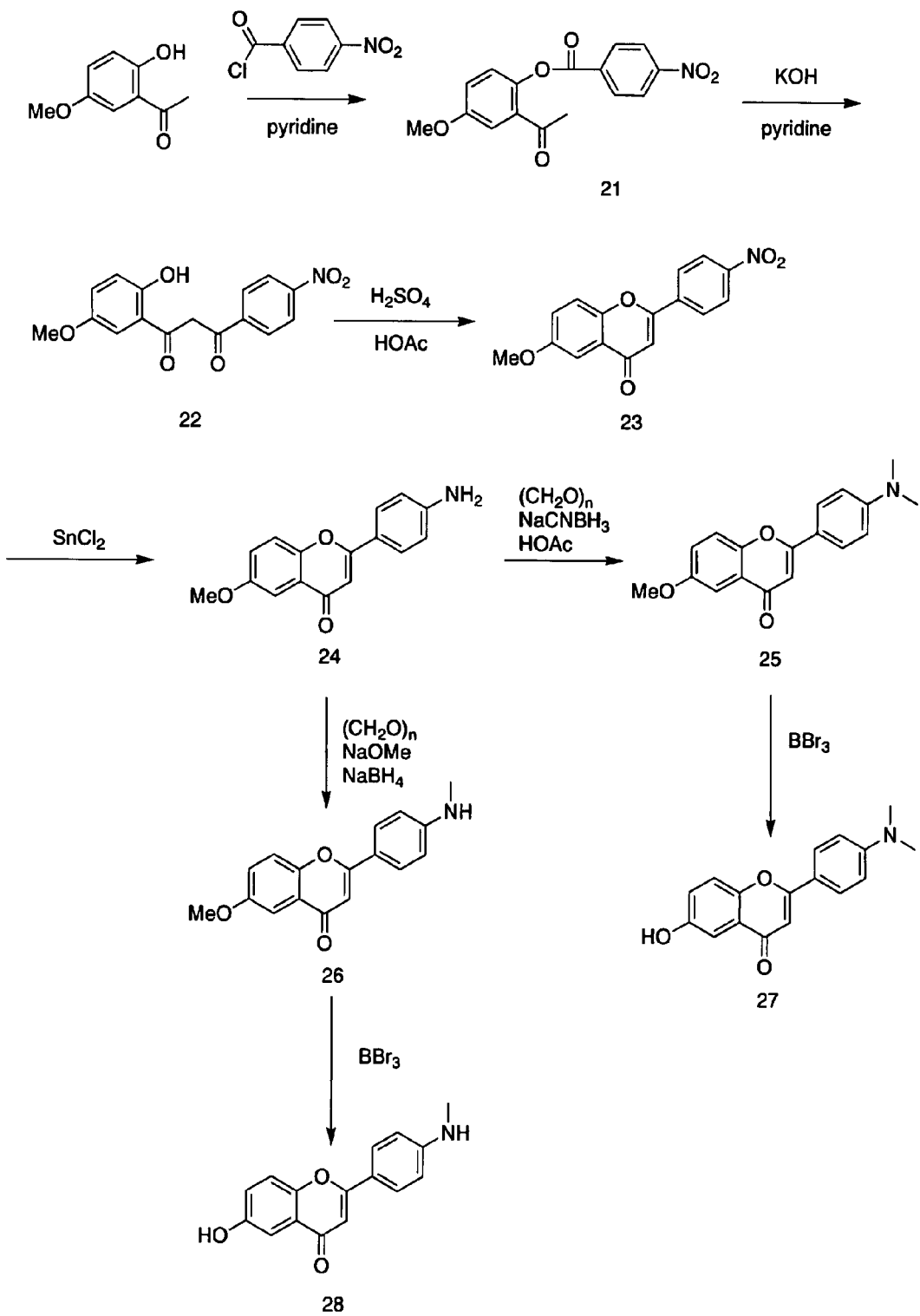
FIG. 3 is a view showing synthetic method (3) of a flavone derivative (the numbers as shown in the figure indicate compound numbers).
Figure 4:
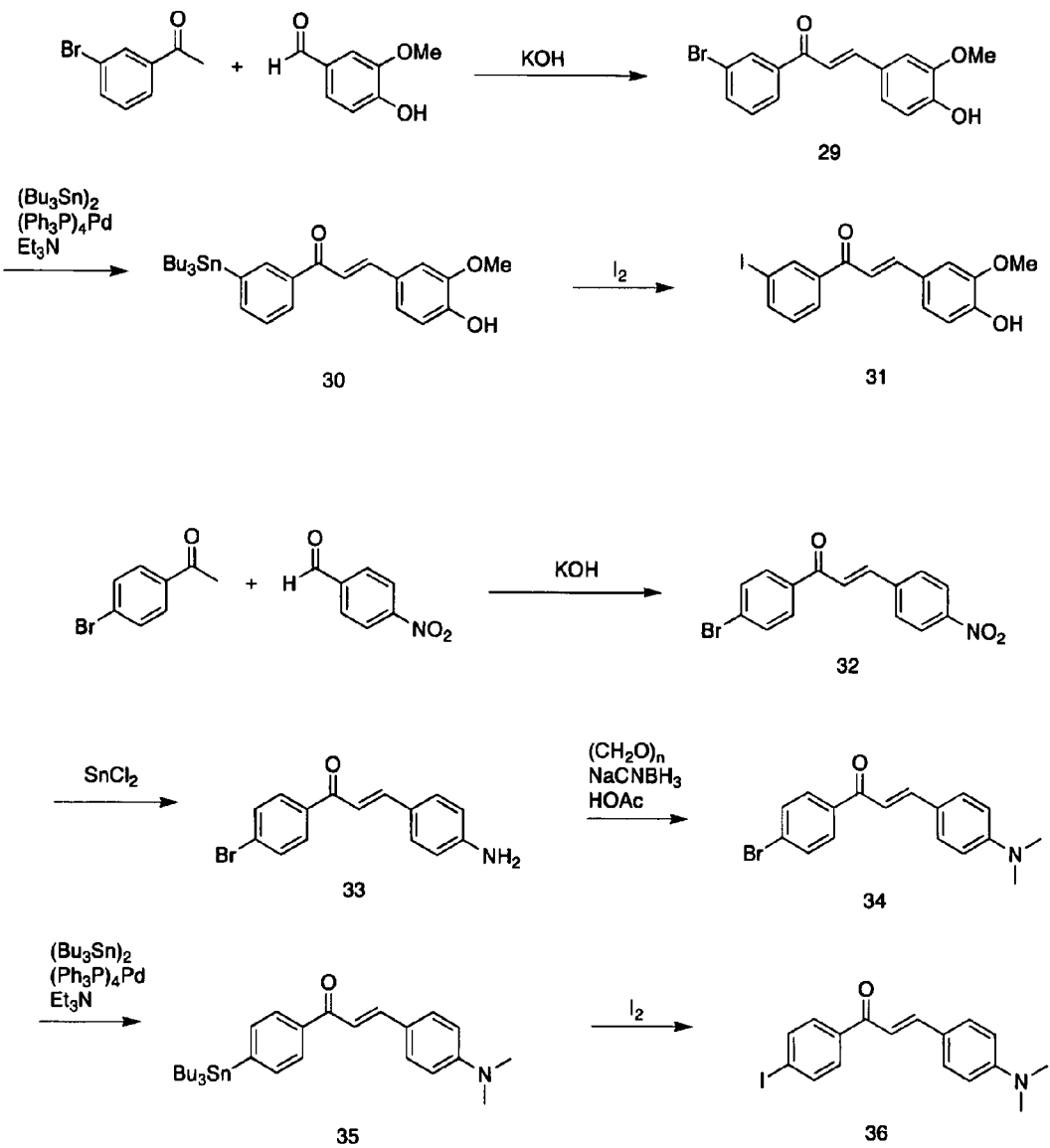
FIG. 4 is a view showing a synthetic method of a chalcone derivative (the numbers as shown in the figure indicate compound numbers).
Figure 5:
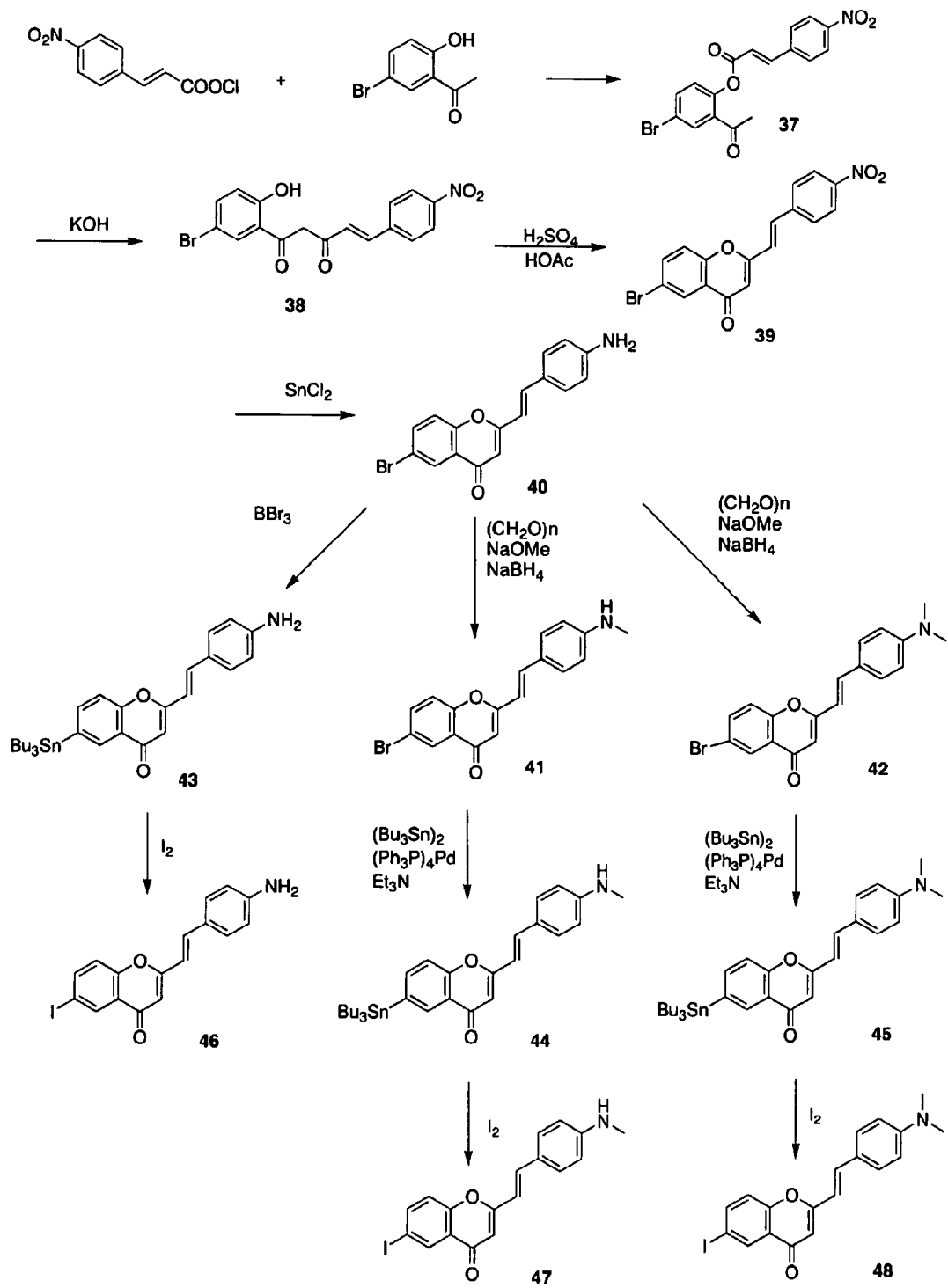
FIG. 5 is a view showing synthetic method (1) of a styryl-chromone derivative (the numbers as shown in the figure indicate compound numbers).
Figure 6:
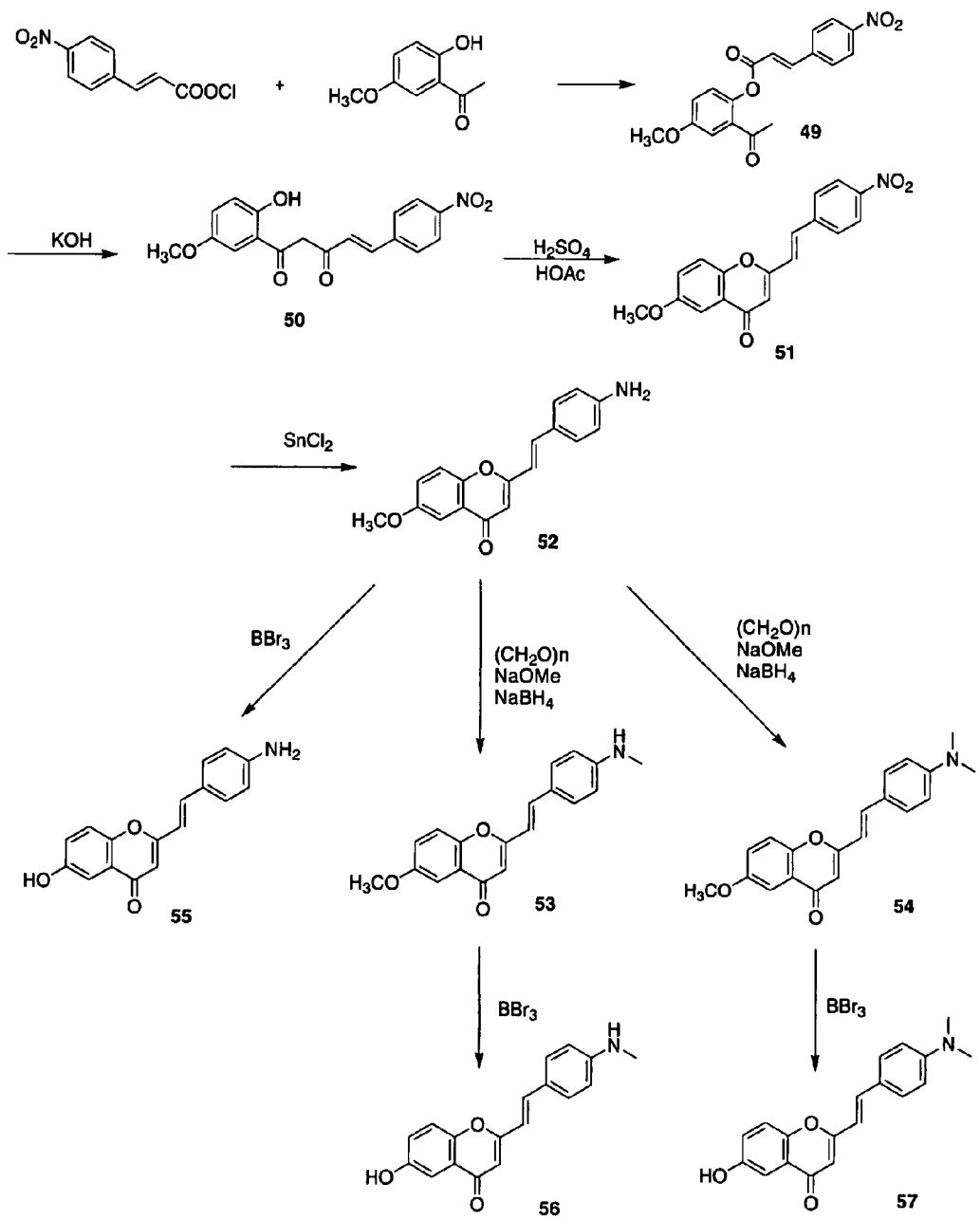
FIG. 6 is a view showing synthetic method (2) of a styryl-chromone derivative (the numbers as shown in the figure indicate compound numbers).
Figure 7:
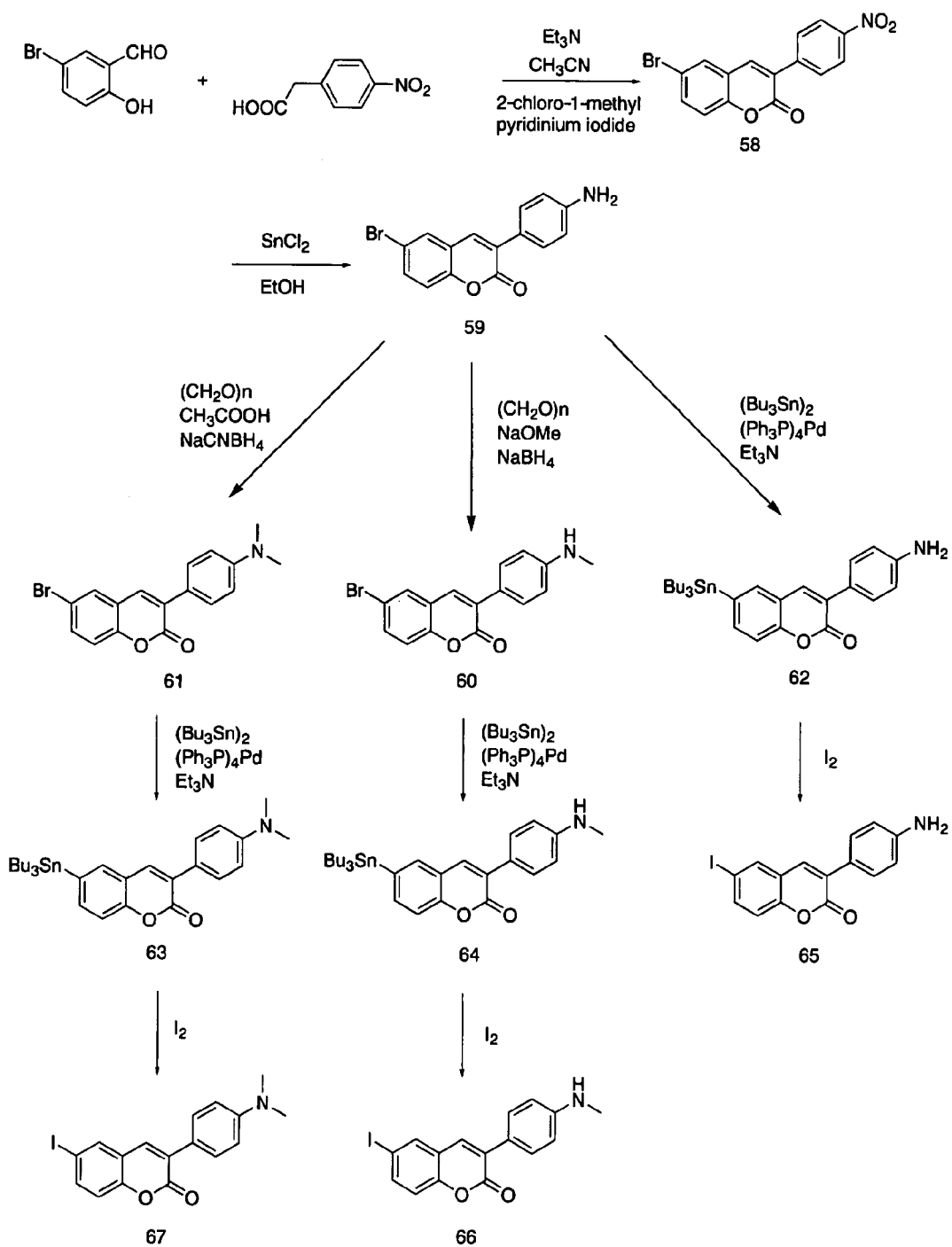
FIG. 7 is a view showing a synthetic method of a coumarin derivative (the numbers as shown in the figure indicate compound numbers).

FIGS. 1, 2, and 3 show synthetic pathways of flavone derivatives. The flavone skeleton was formed by the Baker-Venkataraman reaction. In such a synthetic process, hydroxyacetophenone was converted to benzoyl esters (compounds 2, 13, and 21). These compounds were further subjected to an alkali treatment, so as to convert them to 1,3-diketones (compounds 3, 14, and 22). These diketone bodies were treated with acid, so as to obtain flavone derivatives of interest (compounds 4, 15, and 23). Reduction of the nitro groups of compounds 4 and 23 was carried out using tin(II) chloride as a reducing agent. Dimethylation and monomethylation of the generated amino groups were carried out according to common methods. In addition, the methoxy groups of flavone derivatives (compounds 15, 19, 25, and 26) as shown in FIGS. 2 and 3 were subjected to a demethylation reaction using boron tribromide. Each bromo compound was allowed to react with bis(tributyltin) using palladium as a catalyst, so that the above compound could be converted to a tributyltin body. These tributyltin bodies were easily converted to compounds as a result of a reaction with iodine. FIG. 4 shows a synthetic pathway of a chalcone derivative. With regard to such a chalcone derivative, the basic skeleton of chalcone was formed as a result of the condensation reaction of an acetophenone body with an aldehyde body in the presence of potassium. The subsequent reduction, methylation, conversion to tributyltin, and an exchange reaction of tributyltin-iodine were carried out by the same above method as that used for synthesizing a flavone derivative. FIGS. 5 and 6 show synthetic pathways of styrylchromone derivatives. Such a styrylchromone derivative was synthesized by the same above method as that used for synthesizing a flavone derivative, using nitrocinnamate chloride and bromohydroxybenzophenone as starting materials. FIG. 7 shows a synthetic pathway of a coumarin derivative. Such a coumarin derivative was synthesized using bromohydroxybenzaldehyde and nitrobenzo acetate as starting materials. Reduction, methylation, conversion to tributyltin, and iodination of nitro groups were carried out by the same above method as that used for synthesizing a flavone derivative.

(2) Iodine Labeling Experiment

Figure 8:
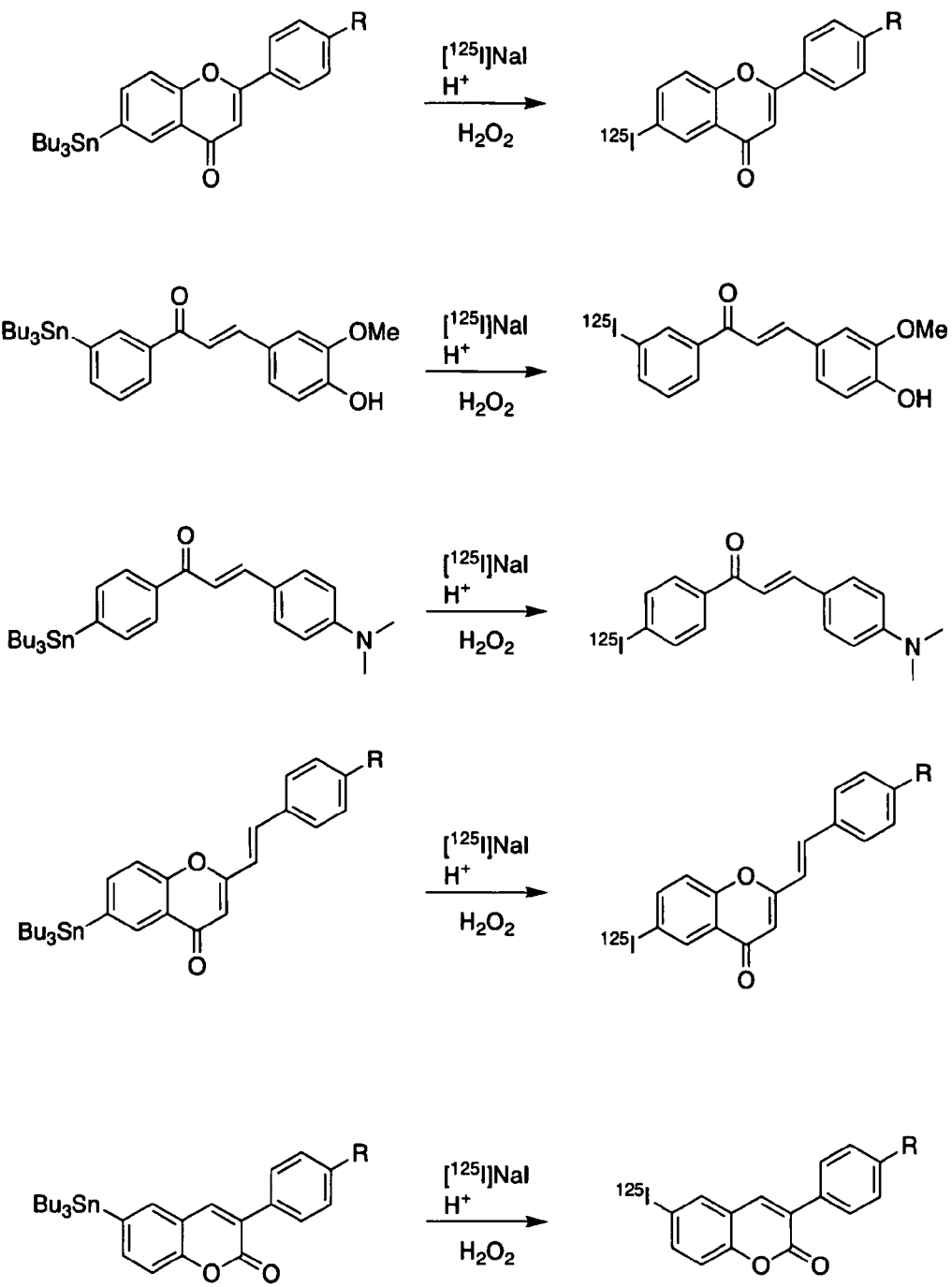
FIG. 8 is a view showing a method labeling a flavone derivative, a chalcone derivative, a styrylchromone derivative, and a coumarin derivative, with radioiodine.

As shown in FIG. 8, labeling with radioiodine was carried out by a tin-iodine exchange reaction using hydrogen peroxide as an oxidizer, so as to obtain a radioiodine-125 labeled form of interest at a radiochemical yield of 50% to 80%. After completion of the labeling reaction, separation and purification were carried out by reversed-phase HPLC, so as to obtain a carrier-free labeled compound at a radiochemical yield of 98% or more.

(3) In Vitro Binding Experiment Using Aβ(1-40) Aggregates and Aβ(1-42) Aggregates

Figure 9:
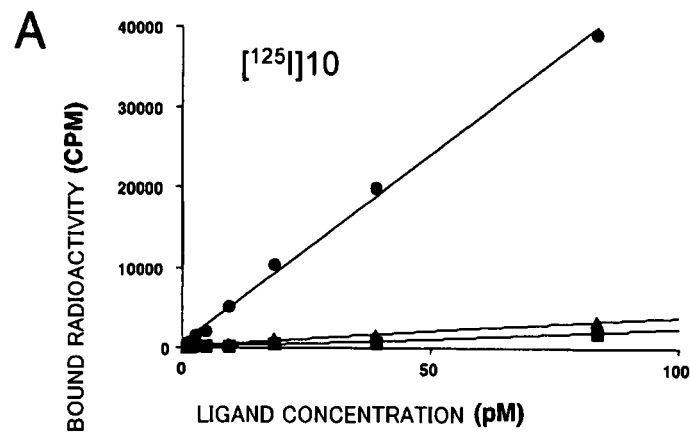
FIG. 9 is a view showing the bindability of compound 10(A), compound 11(B), and compound 19(C), to Aβ aggregates (●: in the presence of Aβ aggregates; ■: in the absence of Aβ aggregates; and ▲: non-specific bond).
Figure 9:
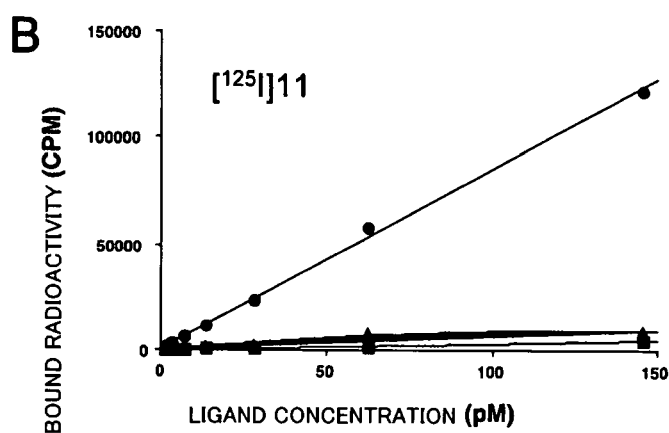
Figure 9:
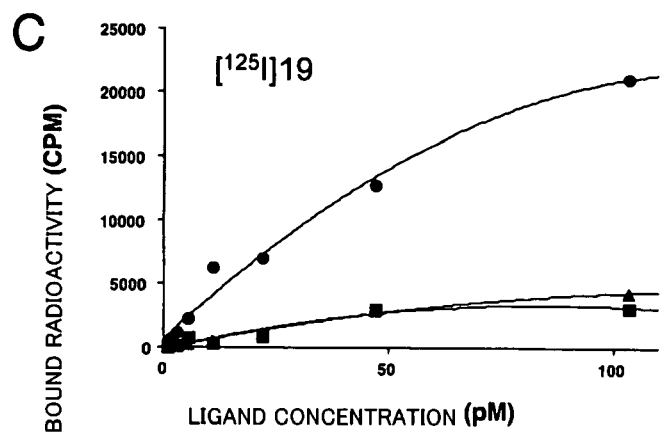
Figure 10:
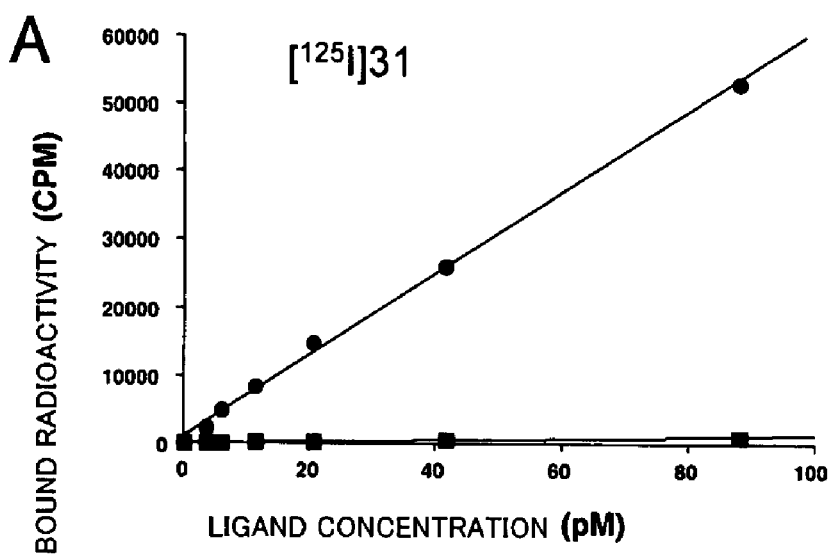
FIG. 10 is a view showing the bindability of compound 31(A) and compound 36(B) to Aβ aggregates (●: in the presence of Aβ aggregates; and ■: in the absence of Aβ aggregates).
Figure 10:
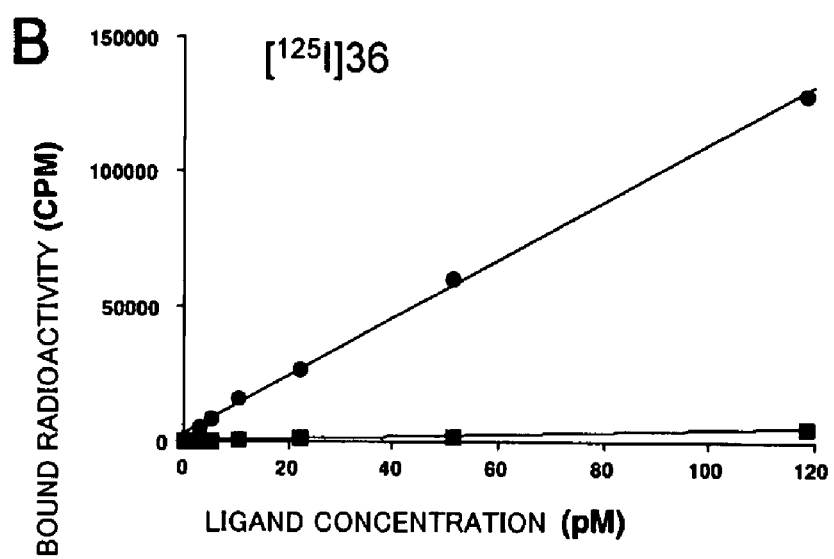
Figure 11:
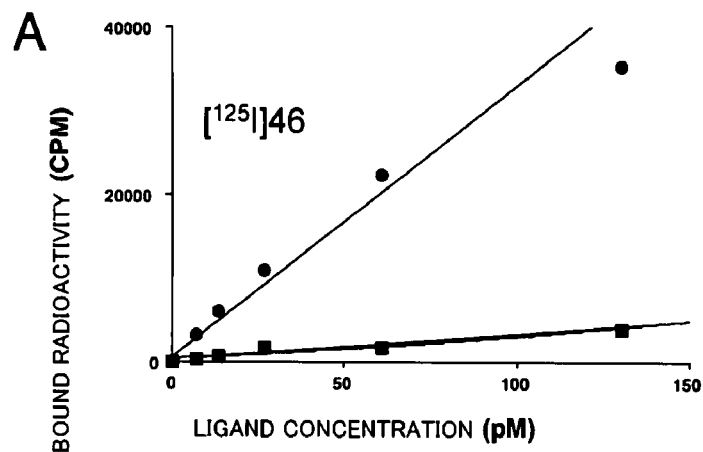
FIG. 11 is a view showing the bindability of compound 46(A), compound 47(B), and compound 48(C), to AD aggregates (●: in the presence of Aβ aggregates; and ■: in the absence of Aβ aggregates).
Figure 11:
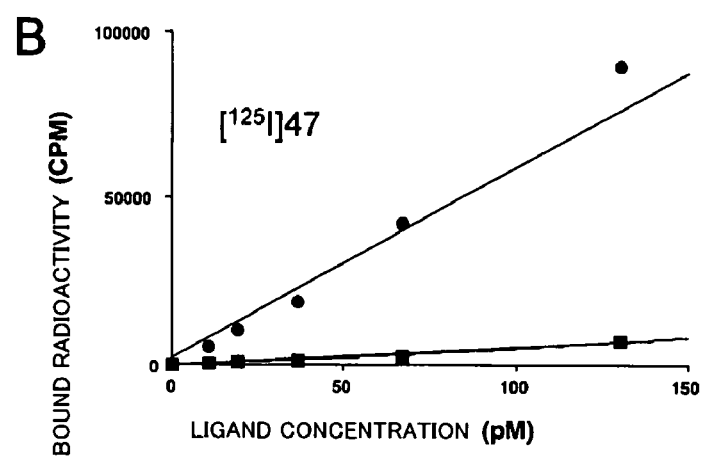
Figure 11:
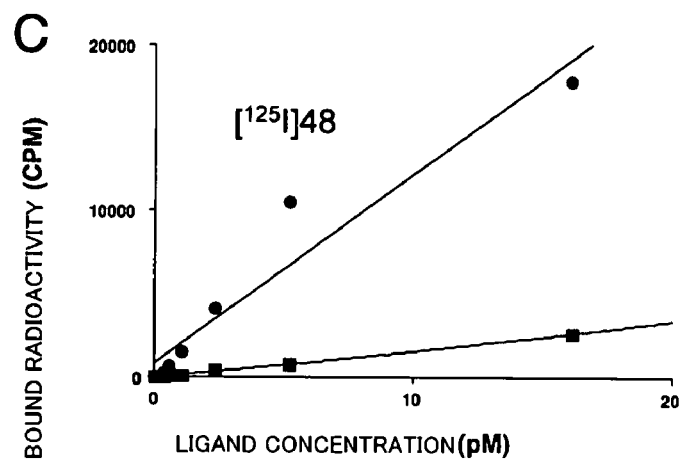
Figure 12:
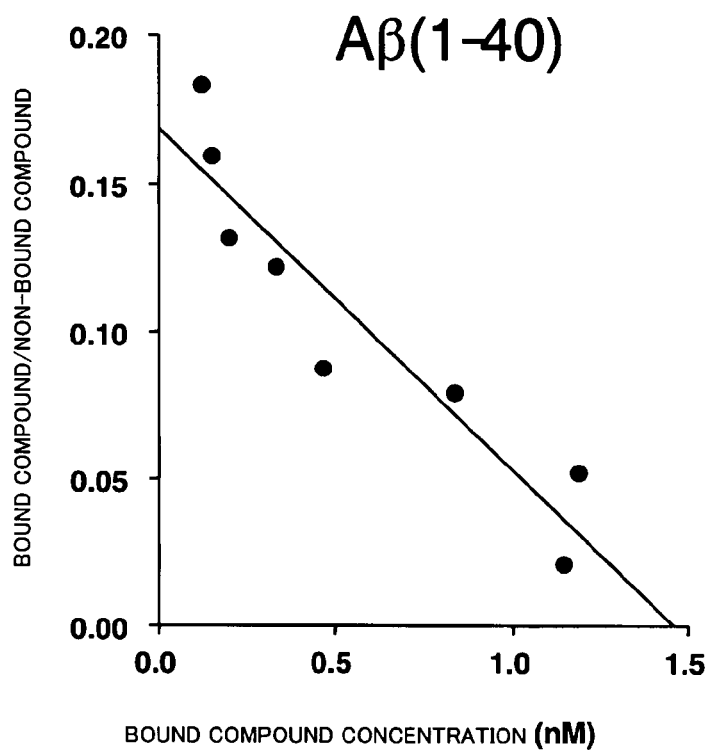
FIG. 12 is a view showing a Scatchard plot obtained as a result of a saturation experiment of compound 11 with Aβ aggregates.
Figure 12:
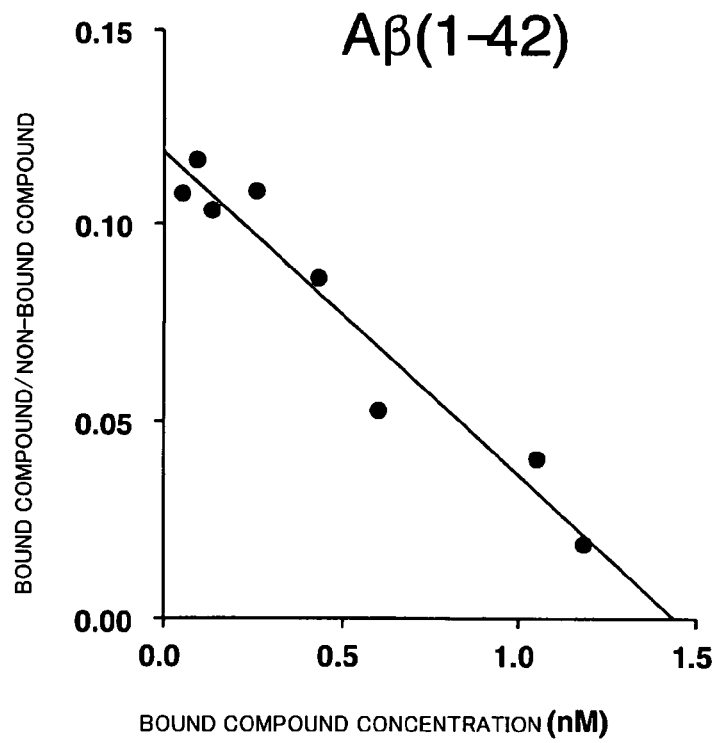

[$^{125}$I] compound 10, [$^{125}$I] compound 11, and [$^{125}$I] compound 19, which had various concentrations, were reacted in the presence of Aβ aggregates, in the absence of Aβ aggregates, or in the presence of an excessive amount of nonradioactive compound 11. Thereafter, the reaction product was filtrated with a cell harvester, and radioactivity remaining on the filter was then measured. FIG. 9 shows the results obtained by the above operations. Both in the absence of the Aβ aggregates and in the presence of an excessive amount of nonradioactive compound, the value of the radioactivity remaining on the filter was low. In contrast, when the reaction was carried out in the presence of the Aβ aggregates, [$^{125}$I] compound 10, [$^{125}$I] compound 11, and [$^{125}$I] compound 19 exhibited significantly high values. From these results, it was revealed that flavone derivatives, namely, all of [$^{125}$I] compound 10, [$^{125}$I] compound 11, and [$^{125}$I] compound 19 exhibit high bindability to the Aβ aggregates. Such bindability increased in the order of [$^{125}$I] compound 11>[$^{125}$I] compound 10>[$^{125}$I] compound 19. Moreover, the same experiment was carried out also on [125I] compound 31, [$^{125}$I] compound 36, [$^{125}$I] compound 46, [$^{125}$I] compound 47, and [$^{125}$I] compound 48. As a result, as in the case of flavone derivatives, chalcone derivatives (compounds 31 and 36) and styrylchromone derivatives (compounds 46, 47, and 48) exhibited high binding affinity to amyloid aggregates (FIGS. 10 and 11). Furthermore, with regard to [$^{125}$I] compound 11, the values obtained from a saturation experiment using the Aβ(1-40) aggregates and the Aβ(1-42) aggregates were analyzed according to the Scatchard analysis (FIG. 12). As a result, the obtained values exhibited linearity, and thus it was revealed that a flavone compound and an amyloid aggregate have a single binging site. Further, the dissociation equilibrium constant (Kd value) was 12.3±2.3 nM with respect to the Aβ(1-40) aggregates, and it was 17.6±5.7 nM with respect to the Aβ(1-42) aggregates. Thus, it was shown that such a flavone compound has a high binding affinity to an amyloid aggregate. Still further, with regard to compounds 10, 11, 19, and 20, an inhibition experiment was carried out using [$^{125}$I] compound 11 as a radioactive ligand (Table 29). As a result, it was found that all of the compounds exhibited high bindability to the Aβ(1-40) aggregates and the Aβ(1-42) aggregates.

The above compounds had high bindability in order of [$^{125}$I] compound 11>[$^{125}$I] compound 10>[$^{125}$I] compound 19>[$^{125}$I] compound 20. A great difference was not confirmed between bindability to the Aβ(1-40) aggregates (FIG. 12A) and bindability to the Aβ(1-42) aggregates (FIG. 12B).

TABLE 29

| Compound | Inhibition constant (Ki, nM) | |
| --- | --- | --- |
|  | Aβ(1-40) | Aβ(1-42) |
| 10 | 22.6 ± 3.4 | 30.0 ± 3.4 |
| 11 | 13.2 ± 0.2 | 15.6 ± 2.4 |

TABLE 29-continued

| Compound | Inhibition constant (Ki, nM) | |
| --- | --- | --- |
|  | Aβ(1-40) | Aβ(1-42) |
| 19 | 29.0 ± 3.2 | 38.3 ± 8.1 |
| 20 | 72.5 ± 8.2 | 77.2 ± 9.2 |

(4) Experiment Regarding Radioactivity Distribution in Mouse Body

Tables 30, 31, and 32 show the results regarding radioactivity distribution in normal mice, which was observed after administration of a flavone derivative, a chalcone derivative, and a styrylchromone derivative, respectively, to the normal mice.

TABLE 30

Distribution of radioactivity in mouse body after intravenous administration of [$^{125}$I] compound 10, [$^{125}$I] compound 11, [$^{125}$I] compound 19, and [$^{125}$I] compound 20[a]

| Tissue | Time elapsed after administration (min) | | | |
| --- | --- | --- | --- | --- |
|  | 2 | 10 | 30 | 60 |
| [$^{125}$I]Compound 11 | | | | |
| Blood | 1.87 (0.18) | 1.07 (0.08) | 1.20 (0.15) | 1.15 (0.16) |
| Liver | 15.41 (0.98) | 21.85 (2.14) | 15.71 (0.96) | 12.40 (2.38) |
| Kidney | 8.33 (1.47) | 4.31 (0.28) | 3.40 (0.31) | 2.32 (0.45) |
| Intestine | 2.24 (0.24) | 6.56 (0.83) | 12.97 (1.15) | 18.64 (2.05) |
| Spleen | 2.72 (0.20) | 1.92 (0.33) | 1.58 (0.31) | 1.18 (0.17) |
| Heart | 5.63 (0.80) | 2.47 (0.14) | 1.69 (0.06) | 1.07 (0.17) |
| Brain | 3.22 (0.15) | 3.61 (0.60) | 1.89 (0.21) | 0.99 (0.10) |
| [$^{125}$I]Compound 10 | | | | |
| Blood | 1.89 (0.28) | 1.39 (0.10) | 1.34 (0.07) | 1.50 (0.09) |
| Liver | 16.28 (0.90) | 25.28 (0.31) | 18.61 (1.81) | 15.14 (0.89) |
| Kidney | 8.13 (1.28) | 5.21 (0.44) | 3.85 (0.33) | 3.05 (0.25) |
| Intestine | 3.10 (0.61) | 7.91 (1.05) | 12.84 (1.18) | 21.48 (3.17) |
| Spleen | 2.57 (1.54) | 2.31 (0.01) | 1.76 (0.23) | 1.52 (0.29) |
| Heart | 4.87 (0.66) | 2.66 (0.12) | 1.67 (0.14) | 1.28 (0.12) |
| Brain | 4.12 (0.15) | 3.68 (0.18) | 1.84 (0.12) | 1.19 (0.04) |
| [$^{125}$I]Compound 19 | | | | |
| Blood | 1.87 (0.21) | 1.19 (0.17) | 0.40 (0.01) | 0.23 (0.09) |
| Liver | 8.96 (1.48) | 9.01 (0.97) | 3.75 (0.47) | 1.88 (0.61) |
| Kidney | 7.99 (1.08) | 6.30 (1.02) | 4.51 (1.59) | 1.46 (1.12) |
| Intestine | 3.52 (0.29) | 14.39 (0.80) | 22.51 (1.11) | 30.05 (3.61) |
| Spleen | 2.70 (0.08) | 1.38 (0.37) | 0.55 (0.30) | 3.67 (5.89) |
| Heart | 4.98 (0.41) | 2.25 (0.40) | 0.84 (0.14) | 0.47 (0.22) |
| Brain | 4.00 (0.18) | 2.36 (0.33) | 0.51 (0.07) | 0.17 (0.05) |
| [$^{125}$I]Compound 20 | | | | |
| Blood | 2.77 (0.43) | 1.58 (0.18) | 0.66 (0.03) | 0.20 (0.02) |
| Liver | 9.77 (1.89) | 8.24 (0.50) | 6.80 (0.86) | 4.78 (1.09) |
| Kidney | 14.79 (2.59) | 15.11 (2.00) | 6.45 (0.84) | 1.66 (0.62) |
| Intestine | 3.12 (0.37) | 11.26 (0.63) | 22.01 (1.34) | 27.28 (0.48) |
| Spleen | 3.92 (1.18) | 1.55 (0.15) | 0.56 (0.13) | 0.17 (0.06) |
| Heart | 5.51 (0.71) | 1.60 (0.18) | 0.53 (0.04) | 0.12 (0.02) |
| Brain | 3.31 (0.32) | 1.90 (0.07) | 0.52 (0.03) | 0.08 (0.02) |

TABLE 31

Distribution of radioactivity in mouse body after intravenous administration of [$^{125}$I] compound 31$^a$

| Tissue | Time elapsed after administration (min) | | | |
|---|---|---|---|---|
| | 2 | 10 | 30 | 60 |
| [$^{125}$I]Compound 31 | | | | |
| Blood | 4.90 (0.52) | 3.80 (0.91) | 1.84 (0.31) | 1.15 (0.44) |
| Liver | 15.71 (1.27) | 18.55 (2.68) | 7.67 (1.68) | 4.05 (0.61) |
| Kidney | 11.99 (3.60) | 9.16 (2.76) | 5.00 (2.27) | 4.31 (0.81) |
| Intestine | 2.50 (0.31) | 10.52 (1.82) | 20.60 (6.13) | 29.31 (3.26) |
| Spleen | 2.57 (0.42) | 1.80 (0.30) | 1.03 (0.04) | 0.88 (0.15) |
| Heart | 5.58 (0.99) | 2.88 (1.02) | 1.44 (0.34) | 1.38 (0.34) |
| Brain | 2.52 (0.20) | 1.28 (0.17) | 0.40 (0.11) | 0.35 (0.05) |

TABLE 32

Distribution of radioactivity in mouse body after intravenous administration of [$^{125}$I] compound 46, [$^{125}$I] compound 47, and [$^{125}$I] compound 48$^a$

| Tissue | Time elapsed after administration (min) | | | |
|---|---|---|---|---|
| | 2 | 10 | 30 | 60 |
| [$^{125}$I]Compound 46 | | | | |
| Blood | 2.34 (0.16) | 2.44 (0.19) | 2.56 (0.64) | 2.27 (0.47) |
| Liver | 13.23 (1.65) | 14.49 (1.10) | 10.27 (1.84) | 8.16 (1.33) |
| Kidney | 11.94 (1.49) | 6.99 (0.91) | 4.91 (1.07) | 3.76 (0.91) |
| Intestine | 2.84 (0.18) | 5.51 (0.55) | 11.71 (1.27) | 16.08 (2.44) |
| Spleen | 4.23 (0.62) | 3.64 (0.38) | 2.92 (0.73) | 2.16 (0.85) |
| Heart | 8.40 (0.47) | 3.78 (0.35) | 2.43 (0.70) | 1.64 (0.29) |
| Brain | 4.88 (0.47) | 4.40 (0.44) | 2.78 (0.72) | 1.62 (0.40) |
| [$^{125}$I]Compound 47 | | | | |
| Blood | 3.21 (0.38) | 2.44 (0.082) | 2.19 (0.29) | 1.79 (0.23) |
| Liver | 14.55 (2.64) | 14.41 (2.52) | 11.13 (1.63) | 7.82 (0.94) |
| Kidney | 10.41 (1.33) | 7.05 (0.56) | 5.48 (0.97) | 3.52 (1.36) |
| Intestine | 2.59 (0.38) | 8.55 (1.21) | 16.72 (2.58) | 19.16 (2.63) |
| Spleen | 3.88 (0.74) | 4.42 (1.05) | 2.66 (0.47) | 1.51 (0.19) |
| Heart | 6.92 (1.41) | 3.31 (0.69) | 2.09 (0.39) | 1.47 (0.27) |
| Brain | 2.84 (0.35) | 2.96 (0.25) | 1.86 (0.30) | 0.99 (0.09) |
| [$^{125}$I]Compound 48 | | | | |
| Blood | 14.54 (3.37) | 3.50 (1.13) | 1.5 (0.22) | 0.80 (0.21) |
| Liver | 20.56 (3.98) | 15.09 (2.63) | 12.82 (1.96) | 8.79 (1.80) |
| Kidney | 9.04 (1.72) | 5.58 (1.07) | 5.16 (1.06) | 3.94 (1.25) |
| Intestine | 1.52 (0.09) | 4.8 (0.74) | 11.98 (1.26) | 14.91 (4.18) |
| Spleen | 5.09 (0.75) | 4.06 (0.66) | 3.15 (0.70) | 2.82 (0.36) |
| Heart | 8.89 (1.94) | 4.00 (0.93) | 2.36 (0.51) | 1.42 (0.38) |
| Brain | 0.70 (0.10) | 0.72 (0.14) | 1.02 (0.23) | 0.77 (0.25) |

$^a$Radioactivity distribution is indicated with the percentage of dosage per gram. Each value represents a mean value of 3 to 5 mice. The value in the parentheses represents a standard deviation.

As shown in Table 30, all the flavone derivatives exhibited rapid clearance from the blood. At the same time, such flavone derivatives exhibited ability to transfer to the brain (approximately 4% ID/g) that was high enough to conduct intracerebral amyloid imaging, from the initial stage of administration. Three types of flavone derivatives had different radioactive dynamics to the brain. However, with regard to all three types of flavone derivatives, rapid washing out of the brain was observed. As for the rate of disappearance, [$^{125}$I] compound 19 was fastest, and [$^{125}$I] compound 20 was second fastest. The disappearance rate of [$^{125}$I] compound 10 was almost the same as that of [$^{125}$I] compound 11. As for such internal radioactive dynamics, it was shown that all the compounds mainly have an excretion pathway from liver to bile duct and then to intestinal canal. In addition, it was confirmed that after administration of a chalcone derivative ([$^{125}$I] compound 31), it transfers to the brain, and that it was then washed out rapidly (Table 31). The radioactivity distribution of styrylchromone derivatives to mouse bodies is shown in Table 32. Regarding compound 48, high radioactivity retention ability in the blood was observed, and the value indicating ability to transfer to the brain was low. In contrast, compounds 46 and 47 exhibited high ability to transfer from the blood to the brain (4.9% ID/g in the case of compound 46, and 3.0% ID/g in the case of compound 47). Further, compounds 46 and 47 exhibited rapid disappearance of radioactivity after it had transferred to the brain.

(5) Binding Experiment Using Brain Tissues of Patient with Alzheimer's Disease

Figure 13:
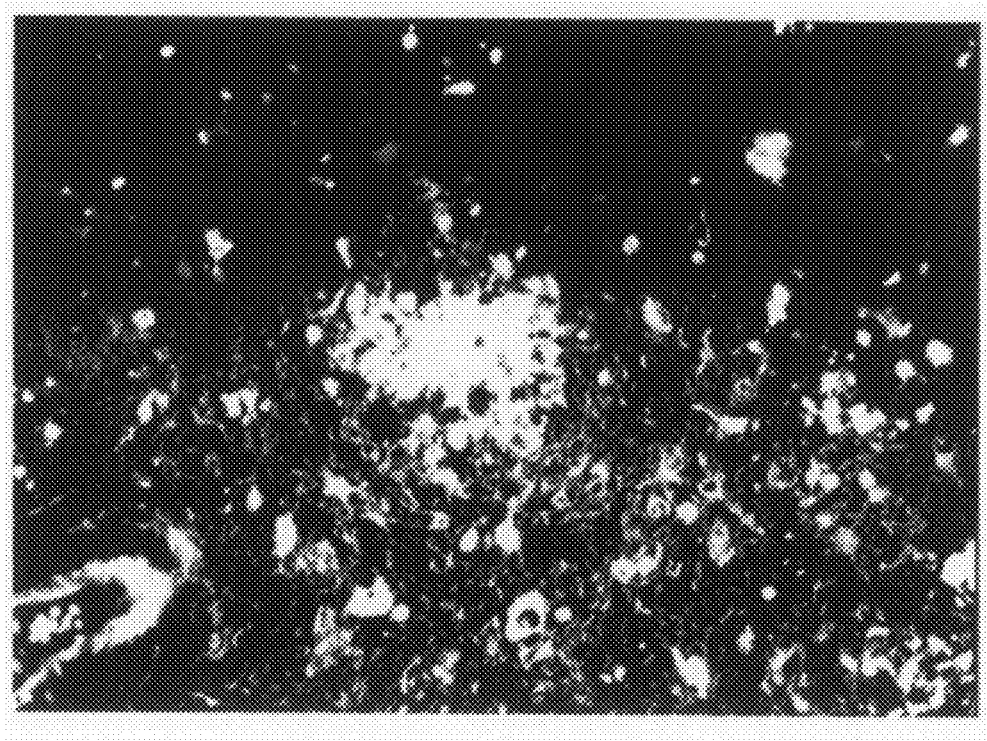
FIG. 13 is a photograph showing the state of compound 11 that binds to senile plaque amyloid in brain tissues affected with Alzheimer's disease (×40 objective lens used, and G filter used). Compound 11 (white portion) binds to senile plaque amyloid (central portion) and cerebrovascular amyloid (lower left portion).
Figure 14:
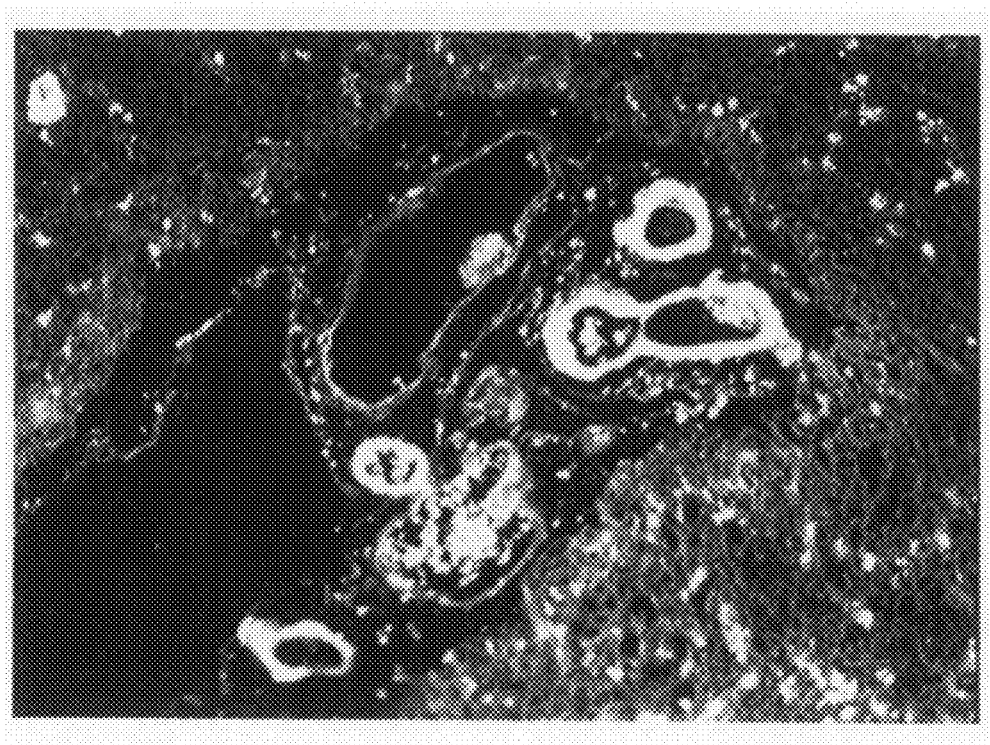
FIG. 14 is a photograph showing the state of compound 11 that binds to senile plaque amyloid in brain tissues affected with Alzheimer's disease (×20 objective lens used, and G filter used). Compound 11 (white portion) binds to cerebrovascular amyloid (4 portions close to the center and 1 portion on the upper left side).
Figure 15:
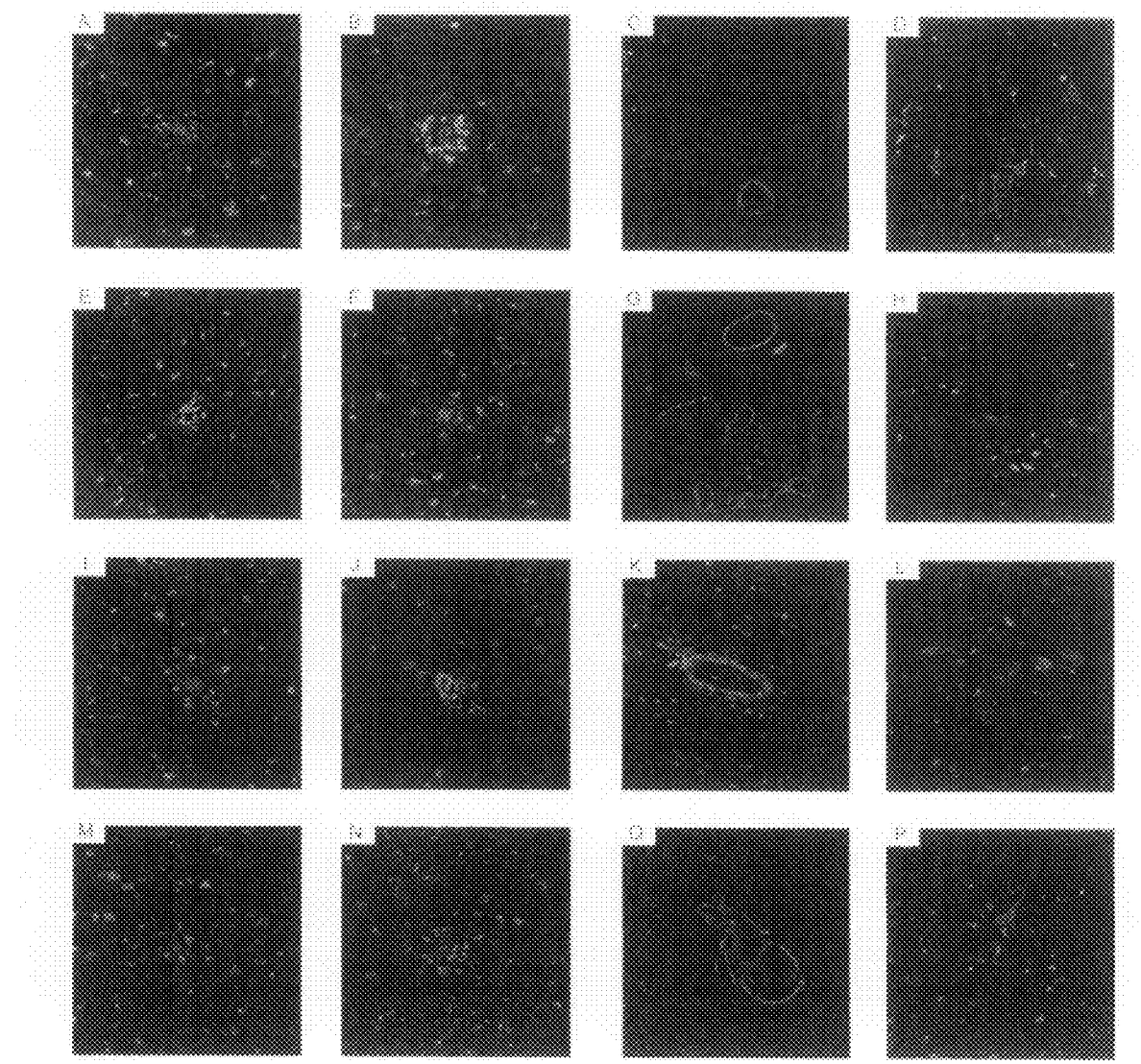
FIG. 15 is a series of photographs showing the state of compounds 10(A-D), 11(E-H), 19(1-L), and 20(M-P) to pathological degeneration in brain tissues affected with Alzheimer's disease (×40 objective lens used, and G filter used). Amyloid plaques (A, E, I, and M), senile plaques having neurodegenerative projections (B, F, J, and N), cerebrovascular amyloids (C, G, K, and O), and neurofibrillary degeneration (D, H, L, and P) are shown in the center of each photograph.

For a definite diagnosis of Alzheimer's disease, it is necessary to confirm the presence of two major lesions, such as deposition of senile plaque and neurofibrillary degeneration, in the temporal lobe site of the brain of a patient. In the binding experiment using the brain tissues of a patient with Alzheimer's disease, it was shown that compound 11 specifically binds to senile plaque (FIG. 13). In addition, as with senile plaque, cerebrovascular angiopathy is a lesion observed in Alzheimer's disease. It has been known that the same amyloid protein is abnormally deposited as for this disease. As shown in FIG. 14, compound 11 specifically binds to cerebrovascular amyloid as well, and thus it was shown that the above compound specifically recognizes an amyloid-deposited lesion existing in the brain tissues of a patient with Alzheimer's disease, and binds thereto. Moreover, as shown in FIGS. 15B and 15H, it was confirmed that compound 11 has bindability also to senile plaque having a neurodegenerative projection and to neurofibrillary degeneration. Furthermore, a binding experiment was also carried out using compounds 10, 19 and 20, which have other substituents, and also using the brain tissues of a patient with Alzheimer's disease. As a result, it was confirmed that as with compound 11, all of these compounds recognize amyloid plaque, senile plaque having a neurodegenerative projection, cerebrovascular amyloid and neurofibrillary degeneration, and bind thereto (FIG. 15). Accordingly, it was shown that all of compounds 10, 11, 19, and 20, which are flavone derivatives, have a property useful for agents used for amyloid imaging.

This specification includes part or all of the contents as disclosed in the specification and/or drawings of Japanese Patent Application No. 2004-341370, which is a priority document of the present application. In addition, all publications, patents and patent applications cited herein are incorporated herein by reference in their entirety.

The invention claimed is:

1. A composition for diagnosing amyloid-related diseases, which comprises a compound represented by the following general formula (Ia) or a pharmaceutically acceptable salt thereof:

[Chemical formula 1]

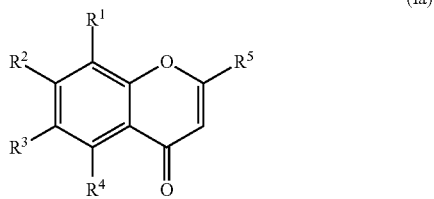

(Ia)

wherein each of $R^1$, $R^2$, $R^3$, and $R^4$ independently represents a hydrogen atom, a halogen atom, a hydroxyl group, a carboxyl group, a sulfone group, a dimethylamino group, a methylamino group, an amino group, a nitro group, an alkyl group containing 1 to 4 carbon atoms, an alkoxy group containing 1 to 4 carbon atoms, a 2-fluoroethoxy group, a 3-fluoropropoxy group, a 4-fluorobutoxy group, or a 5-fluoropentoxy group; $R^5$ represents an aryl group that is optionally substituted with one or two or more substituents selected from the following substituent group A, an aromatic heterocyclic group that is optionally substituted with one or two or more substituents selected from the following substituent group A, or a group represented by the formula: —CH=CH—$R^6$ (wherein $R^6$ represents an aryl group that is optionally substituted with one or two or more substituents selected from the following substituent group A, or an aromatic heterocyclic group that is optionally substituted with one or two or more substituents selected from the following substituent group A); and the substituent group A is a group consisting of a halogen atom, a hydroxyl group, a carboxyl group, a sulfone group, a dimethylamino group, a methylamino group, an amino group, a nitro group, an alkyl group containing 1 to 4 carbon atoms, and an alkoxy group containing 1 to 4 carbon atoms;
wherein the compound represented by general formula (Ia) is labeled with a radionuclide.

2. The composition for diagnosing amyloid-related diseases according to claim 1, wherein any one of $R^1$, $R^2$, $R^3$, and $R^4$ in general formula (Ia) is a halogen atom.

3. The composition for diagnosing amyloid-related diseases according to claim 1, wherein any one of $R^1$, $R^2$, $R^3$, and $R^4$ in general formula (Ia) is an iodine atom.

4. The composition for diagnosing amyloid-related diseases according to claim 1, wherein $R^5$ in general formula (Ia) is a phenyl group that may be substituted with one or two or more substituents selected from the substituent group A.

5. The composition for diagnosing amyloid-related diseases according to claim 1, wherein $R^5$ in general formula (Ia) is a 4-dimethylaminophenyl group, a 4-methylaminophenyl group, a 4-methoxyphenyl group, or a 4-hydroxyphenyl group.

6. The composition for diagnosing amyloid-related diseases according to claim 1, wherein $R^5$ in general formula (Ia) is a group represented by the formula: —CH=CH—$R^6$ (wherein $R^6$ represents a phenyl group that may be substituted with one or two or more substituents selected from the substituent group A).

7. The composition for diagnosing amyloid-related diseases according to claim 1, wherein $R^5$ in general formula (Ia) is a 4-aminostyryl group, a 4-methylaminostyryl group, or a 4-dimethylaminostyryl group.

8. The composition for diagnosing amyloid-related diseases according to claim 1, wherein the radionuclide is a positron-emitting radionuclide.

9. The composition for diagnosing amyloid-related diseases according to claim 1, wherein the radionuclide is a γ-ray-emitting radionuclide.

10. The composition for diagnosing amyloid-related diseases according to claim 1, wherein the amyloid-related disease is Alzheimer's disease.

* * * * *